(12) United States Patent
Park et al.

(10) Patent No.: US 11,133,471 B2
(45) Date of Patent: Sep. 28, 2021

(54) COMPOUND FOR ORGANIC ELECTRONIC ELEMENT, ORGANIC ELECTRONIC ELEMENT USING SAME AND ELECTRONIC DEVICE THEREFOR

(71) Applicant: DUK SAN NEOLUX CO., LTD, Cheonan-si (KR)

(72) Inventors: Hyoung Keun Park, Chuncheon-si (KR); Yun Suk Lee, Seongnam-si (KR); Ki Ho So, Cheonan-si (KR); Jong Gwang Park, Cheonan-si (KR); Yeon Seok Jeong, Hoengseong-gun (KR); Jung Hwan Park, Hwaseong-si (KR); Sun Hee Lee, Hwaseong-si (KR); Hak Young Lee, Cheonan-si (KR)

(73) Assignee: Duk San Neolux Co., Ltd

( * ) Notice: Subject to any disclaimer, the term of this patent is extended or adjusted under 35 U.S.C. 154(b) by 230 days.

(21) Appl. No.: 16/334,801

(22) PCT Filed: Sep. 18, 2017

(86) PCT No.: PCT/KR2017/010192
§ 371 (c)(1),
(2) Date: Mar. 20, 2019

(87) PCT Pub. No.: WO2018/056658
PCT Pub. Date: Mar. 29, 2018

(65) Prior Publication Data
US 2020/0020863 A1    Jan. 16, 2020

(30) Foreign Application Priority Data
Sep. 22, 2016 (KR) .................. 10-2016-0121408

(51) Int. Cl.
*H01L 51/50* (2006.01)
*H01L 51/00* (2006.01)
(Continued)

(52) U.S. Cl.
CPC ........ *H01L 51/0061* (2013.01); *C07D 333/76* (2013.01); *C07D 409/14* (2013.01);
(Continued)

(58) Field of Classification Search
None
See application file for complete search history.

(56) References Cited

U.S. PATENT DOCUMENTS 8,507,904 B2    8/2013    Kim et al.
9,017,828 B2    4/2015    Kim et al.
(Continued)

FOREIGN PATENT DOCUMENTS

KR    10-2013-0096334 A    8/2013
KR    10-2014-0001568 A    1/2014
(Continued)

OTHER PUBLICATIONS

International Search Report (in English and Korean) and Written Opinion (in Korean) issued in PCT/KR2017/010192, dated Dec. 13, 2017; ISA/KR.

*Primary Examiner* — Gregory D Clark
(74) *Attorney, Agent, or Firm* — Harness, Dickey & Pierce, P.L.C.

(57) ABSTRACT

Disclosed is a compound represented by chemical formula (1). In addition, disclosed is an organic electronic element comprising: a first electrode; a second electrode; and an organic layer between the first electrode and the second electrode, wherein the organic layer contains the compound represented by chemical formula (1). Light-emitting efficiency, stability and lifespan may be enhanced when the (Continued)

compound represented by chemical formula (1) is contained in the organic layer.

11 Claims, 1 Drawing Sheet

(51) Int. Cl.
*C07D 333/76* (2006.01)
*C07D 409/14* (2006.01)
*C09K 11/06* (2006.01)
*H01L 51/05* (2006.01)
*H01L 51/42* (2006.01)

(52) U.S. Cl.
CPC ...... *C09K 11/06* (2013.01); *C09K 2211/1018* (2013.01); *H01L 51/0003* (2013.01); *H01L 51/0004* (2013.01); *H01L 51/0005* (2013.01); *H01L 51/0072* (2013.01); *H01L 51/0073* (2013.01); *H01L 51/0074* (2013.01); *H01L 51/0504* (2013.01); *H01L 51/42* (2013.01); *H01L 51/504* (2013.01)

(56) References Cited

U.S. PATENT DOCUMENTS

| | | | |
|---|---|---|---|
| 9,691,990 | B2 | 6/2017 | Mun et al. |
| 2012/0305906 | A1 | 12/2012 | Kim et al. |
| 2013/0001540 | A1 | 1/2013 | Kim et al. |
| 2013/0069049 | A1 | 3/2013 | Park et al. |
| 2014/0027747 | A1 | 1/2014 | Mun et al. |
| 2016/0005981 | A1 | 1/2016 | Kim et al. |
| 2017/0141311 | A1 | 5/2017 | Lee et al. |
| 2017/0170407 | A1 | 6/2017 | Park et al. |
| 2017/0200903 | A1 | 7/2017 | Park et al. |
| 2017/0256719 | A1 | 9/2017 | Jang et al. |
| 2018/0083204 | A1 | 3/2018 | Kim et al. |
| 2019/0047992 | A1 | 2/2019 | Park et al. |

FOREIGN PATENT DOCUMENTS

| | | | | |
|---|---|---|---|---|
| KR | 10-2015-0004099 A | | 1/2015 | |
| KR | 10-1614738 | * | 4/2016 | ............. H01L 51/50 |
| KR | 10-1614738 B1 | | 4/2016 | |
| KR | 10-2016-0054855 A | | 5/2016 | |

* cited by examiner

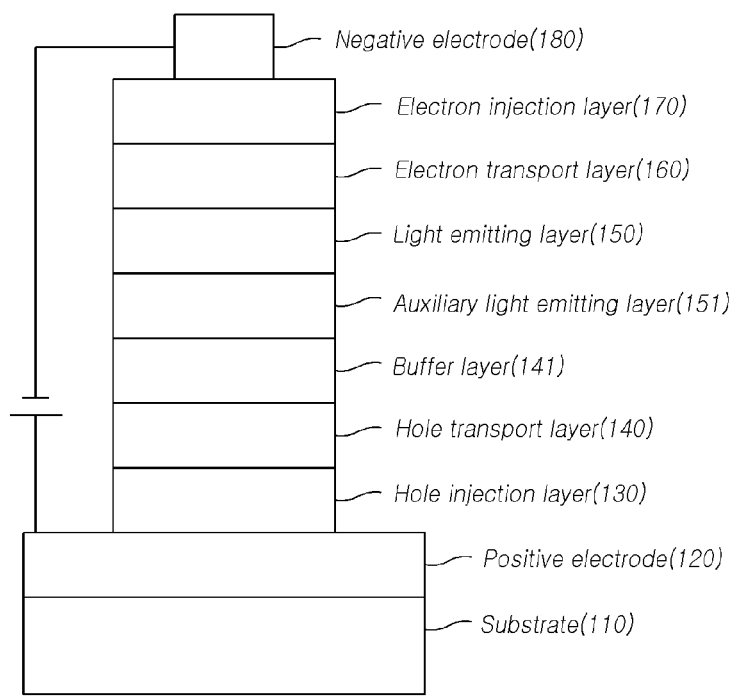

COMPOUND FOR ORGANIC ELECTRONIC ELEMENT, ORGANIC ELECTRONIC ELEMENT USING SAME AND ELECTRONIC DEVICE THEREFOR

CROSS-REFERENCE TO RELATED APPLICATIONS

This application is a U.S. National Phase Application under 35 U.S.C. 371 of International Application No. PCT/KR2017/010192, filed on Sep. 18, 2017, which claims the benefit of Korean Patent Application No. 10-2016-0121408, filed on Sep. 22, 2016. The disclosures of the above applications are incorporated herein by reference. Furthermore, this patent application claims priorities in countries other than U.S., with the same reason based on the Korean Patent Application, the entire contents of which are incorporated herein by reference.

TECHNICAL FIELD

The present disclosure relates to a compound for an organic electric element, an organic electric element using the same, and an electronic device comprising the same.

BACKGROUND ART

In general, organic light emission refers to a phenomenon in which electric energy is converted into light energy by using an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve efficiency and stability of an organic electric element, and for example, may include a hole injection layer, a hole transport layer, a light emitting layer, an electron transport layer, an electron injection layer, and the like.

A material used for an organic material layer in an organic electric element may be classified into a light emitting material and a charge transport material, for example, a hole injection material, a hole transport material, an electron transport material, an electron injection material, and the like, according to its function.

Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and further divided into yellow and orange light emitting materials required for better natural color reproduction according to its light emitting color.

When only one material is used as a light emitting material, a maximum light emission wavelength is shifted to a longer wavelength due to intermolecular interactions, causing the deterioration in color purity, or efficiency of elements is lowered due to a luminous attenuation effect. Therefore, a host/dopant system may be used as the light emitting material in order to improve color purity and increase luminous efficiency through energy transfer. This is based on the principle that if a small amount of dopant having a smaller energy band gap than a host forming a light emitting layer is mixed in the light emitting layer, excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the market for portable displays is on the way to large-area displays, and thus the sizes of displays are increasing. As a result, the larger power consumption than is required in existing portable displays is required. Therefore, the power consumption is a very important factor in portable displays with a limited power source, such as a battery, and efficiency and lifespan issue also are solved.

Efficiency, lifespan, driving voltages, and the like are correlated with each other. If the efficiency is increased, the driving voltage is relatively lowered, and as the driving voltage is lowered, the crystallization of an organic material due to Joule heating generated during operation is reduced, and as a result, the lifespan shows a tendency to increase. However, the efficiency cannot be maximized only by simply improving the organic material layer. The reason that both long lifespan and high efficiency can be achieved when there is an optimal combination of energy levels and T1 values, inherent material properties (mobility, interfacial properties, etc.), and the like among the respective layers included in the organic material layer. Accordingly, there is a need for the development of light emitting materials that can retain high thermal stability and an efficient charge balance in a light emitting layer.

Further, in order to solve the light emission problem with a hole transport layer in a recent organic electric element, an auxiliary light emitting layer is essentially present between the hole transport layer and a light emitting layer, and it is time to develop different auxiliary light emitting layers according to respective light emitting layers (R, G, B).

In general, an electron transferred from an electron transport layer to a light emitting layer and a hole transferred from a hole transport layer to the light emitting layer are recombined to form an exciton. However, a material used in a hole transport layer should have a low HOMO value, and thus it mainly has a low T1 value. Due to this, excitons generated from a light emitting layer are transported to the hole transport layer, resulting in a charge unbalance in the light emitting layer, thereby emitting light in an interface of the hole transport layer.

When light emission occurs in the interface of the hole transport layer, the organic electric element suffers from disadvantage of the deteriorations in color purity and efficiency and a reduction in lifespan. Therefore, there is an urgent need to develop an auxiliary light emitting layer, which has a high T1 value and a HOMO level between the HOMO energy level of a hole transport layer and the HOMO energy level of a light emitting layer.

That is, in order to allow the organic electric element to sufficiently exhibit excellent characteristics, most of all, materials constituting an organic material layer in the element, for examples, a hole injection material, a hole transport material, a light emitting material, an electron transport material, an electron injection material, and the like need to be supported by stable and efficient materials. However, the development of stable and efficient materials for the organic material layer for an organic electric element is not sufficiently achieved. Therefore, the development of new materials is continuously required, and especially, the development of a host material of the light emitting layer and a material of the auxiliary light emitting layer is urgently required.

DETAILED DESCRIPTION OF THE INVENTION

Technical Problem

In order to solve the above-mentioned problems occurring in the prior art, an object of the present disclosure is to provide a compound capable of achieving high luminous efficiency, low driving voltages, high heat resistance, and improved color purity and lifespan of an element, an organic electric element using the same, and an electronic device including the same.

Technical Solution

In accordance with an aspect of the present disclosure, there is provided a compound represented by the formula below.

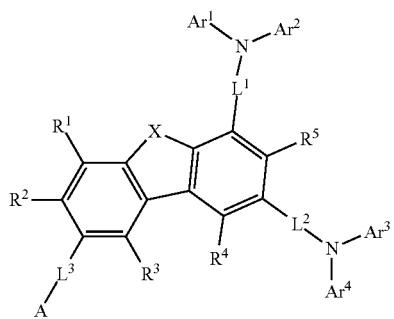

Formula (1)

In another aspect of the present disclosure, there are provided an organic electric element using the compound represented by the above formula, and an electronic device including the same.

Advantageous Effects

By using the compound according to the present disclosure, high luminous efficiency, low driving voltages, and high heat resistance of an element can be achieved, and color purity and lifespan of the element can be improved.

BRIEF DESCRIPTION OF THE DRAWINGS

FIG. 1 is a cross-sectional view of an organic light emitting diode according to an embodiment of the present disclosure.

MODE FOR CARRYING OUT THE INVENTION

Hereinafter, embodiments of the present disclosure will be described in detail with reference to the accompanying drawings.

In designation of reference numerals to components in respective drawings, it should be noted that the same elements would be designated by the same reference numerals although they are shown in different drawings. Further, in the following description of the present disclosure, a detailed description of known functions and configurations incorporated herein will be omitted when it may make the subject matter of the present disclosure rather unclear.

Terms, such as first, second, A, B, (a), (b), or the like may be used herein when describing components of the present disclosure. Each of these terminologies is not used to define an essence, order, or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component. In addition, it should be noted that when an element such as a layer, a film, a region, a plate, or the like is "above" or "on" other element, and the like, this may include not only the case "directly above" other element but also the case where there is other element in the middle. On the contrary, it should be noted that that when an element is "directly above" other element, it means that there is no other element in the middle.

As used in the specification and the accompanying claims, unless otherwise stated, the meanings of the terms are as follows.

Unless otherwise stated, the term "halo" or "halogen" as used herein includes fluorine (F), bromine (Br), chlorine (Cl), and iodine (I).

Unless otherwise stated, the term "alkyl" or "alkyl group" as used herein means a radical of a saturated aliphatic functional group having 1 to 60 carbon atoms with single bond(s), including a linear alkyl group, a branched-chain alkyl group, a cycloalkyl (alicyclic) group, an alkyl-substituted cycloalkyl group, and a cycloalkyl-substituted alkyl group.

Unless otherwise stated, the term "haloalkyl group" or "halogen alkyl group" as used herein means an alkyl group substituted with halogen.

Unless otherwise stated, the term "alkenyl group" or "alkynyl group" as used herein means a functional group having 2 to 60 carbon atoms with a double or triple bond and includes a linear-chain or branched-chain group, but is not limited thereto.

Unless otherwise stated, the term "cycloalkyl" as used herein means alkyl forming a ring having 3 to 60 carbon atoms, but is not limited thereto.

Unless otherwise stated, the term "alkoxy group" or "alkyloxy group" as used herein means an alkyl group to which an oxygen radical is attached, the alkyl group having 1 to 60 carbon atoms, but is not limited thereto.

Unless otherwise stated, the term "aryloxy group" or "aryloxy group" as used herein means an aryl group to which an oxygen radical is attached to, the aryl group having 6 to 60 carbon atoms, but not limited thereto.

Unless otherwise stated, the term "fluorenyl group" or "fluorenylene group" as used herein means, univalent or bivalent functional group in which R, R' and R" are all hydrogen in the formula below. Also, the term "substituted fluorenyl group" or "substituted fluorenylene group" means, a functional group in which at least any one of R, R' and R" is a substituent other than hydrogen, and includes a case in which R and R' are linked to each other to form a spiro compound together with a carbon atom to which they are attached.

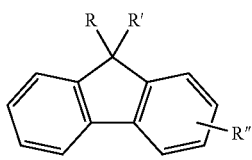

Unless otherwise stated, the terms "aryl group" and "arylene group" each as used herein mean a functional group having 6 to 60 carbon atoms, but are not limited thereto. The aryl group or arylene group herein includes monocyclic types, ring assemblies, fused polycyclic systems, spiro compounds, and the like.

Unless otherwise stated, the term "heterocyclic group" as used herein means a ring having 2 to 60 carbon atoms, including a non-aromatic ring as well as an aromatic ring, like "heteroaryl group" or "heteroarylene group", but is not limited thereto. Unless otherwise stated, the term "heteroatom" as used herein represents N, O, S, P, or Si, and the heterocyclic group includes monocyclic types, ring assemblies, fused polycyclic systems, spiro compounds, and the like, which contain a heteroatom.

Also, the term "heterocyclic group" may include a ring containing $SO_2$ instead of carbon constituting the ring. For example, "heterocyclic group" includes the compound below.

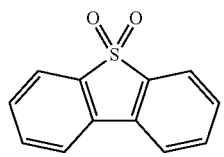 [SMILES: O=S1(=O)c2ccccc2-c2ccccc21]

The term "ring" as used herein includes monocyclic and polycyclic rings, includes not only a hydrocarbon ring but also a heterocyclic ring containing at least one heteroatom, and includes aromatic and non-aromatic rings.

The term "polycyclic" as used herein includes ring assemblies, such as biphenyl and terphenyl, fused polycyclic systems, and spiro compounds, includes aromatic and non-aromatic rings, and includes not only a hydrocarbon ring but also a heterocyclic group containing at least one heteroatom.

The term "ring assemblies" as used herein means two or more cyclic systems (monocyclic or fused cyclic systems) which are directly joined to each other via double or single bonds, wherein the number of such direct ring junctions is one less than the number of cyclic systems involved in these compounds. In the ring assemblies, same or different ring systems may be directly joined to each other via double or single bonds.

The term "fused polycyclic system" as used herein means a fused ring type which has at least two atoms as common members, and includes a type in which two or more hydrocarbon ring systems are fused, a type in which at least one heterocyclic system containing at least one heteroatom is fused, and the like. Such a fused polycyclic system may be an aromatic ring, a heteroaromatic ring, an aliphatic ring, or a combination thereof.

The term "spiro compound" as used herein means a compound having a "spiro union", which means a union of two rings by having only one atom as a common member.

The common atom of the two rings is designated as "spiro atom". The compounds are defined as "monospiro-", "dispiro-", or "trispiro-" depending on the number of spiro atoms in one compound.

Also, when prefixes are named subsequently, it means that substituents are listed in the order described first. For example, an arylalkoxy group means an alkoxy group substituted with an aryl group, an alkoxylcarbonyl group means a carbonyl group substituted with an alkoxy group, and an arylcarbonylalkenyl group also means an alkenyl group substitutes with an arylcarbonyl group, wherein the arylcarbonyl group may be a carbonyl group substituted with an aryl group.

Unless otherwise stated, the term "substituted" in the term "substituted or unsubstituted" as used herein means a substitution with at least one substituent selected from the group consisting of deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted with deuterium, a $C_8$-$C_{20}$ arylalkenyl group, a silane group, a boron group, a germanium group, and a $C_5$-$C_{20}$ heterocyclic group including at least one of a heteroatom selected from the group consisting of O, N, S, Si and P, but is not limited thereto.

Unless otherwise specified, the formulas used in the present disclosure are applied in the same manner as in the definition of substituents by the definition of an exponent in the formula below.

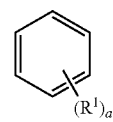

Here, when a is an integer of zero, substituent $R^1$ is absent; when a is an integer of 1, one substitutent $R^1$ is linked to any one of the carbon atoms constituting the benzene ring; and when a is an integer of 2 or 3, substituents $R^1$'s may be the same and different and may be linked to the benzene ring as follows. When a is an integer of 4 to 6, substituents $R^1$'s may be the same and different and may be linked to the benzene ring in a similar manner to that when a is an integer of 2 or 3. The indication of hydrogen atoms linked to carbon constituents of the benzene ring is omitted.

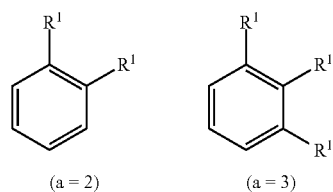

FIG. 1 is an exemplary view of an organic electric element according to an embodiment of the present disclosure.

Referring to FIG. 1, an organic electric element 100 according to an embodiment of the present disclosure includes a first electrode 120 formed on a substrate 110, a second electrode 180, and an organic material layer between the first electrode 120 and the second electrode 180, the organic material layer containing the compound of the present disclosure. Here, the first electrode 120 may be an anode (positive electrode), and the second electrode 180 may be a cathode (negative electrode). In a case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170, which are formed in sequence on the first electrode 120. Here, at least one of these layres may be omitted, or the organic material layer may further include a hole blocking layer, an electron blocking layer, an auxiliary light emitting layer 151, a buffer layer 141, or the like. The electron transport layer 160 or the like may serve as the hole blocking layer.

Although not shown, the organic electric element according to an embodiment of the present disclosure may further include a protective layer or a light efficiency improving layer (capping layer), which is formed at least one of the sides the first and second electrodes, which is a side opposite to the organic material layer.

The compound of the present disclosure employed in the organic material layer may be used as a material of the hole injection layer 130, the hole transport layer 140, the electron transport layer 160, the electron injection layer 170, the light emitting layer 150, the light efficiency improvement layer, the auxiliary light emitting layer, or the like. As an example, the compound of the present disclosure may be used as a material of the auxiliary light emitting layer 151 and/or the light emitting layer 150.

Since a band gap, electrical properties, interfacial properties, and the like may vary in spite of the same core depending on the type and position of a substituent to be attached, it is very important what the types of core and a combination of substituent attached to the core are. Specially, both long lifespan and high efficiency can be achieved when an optimal combination of energy levels, $T_1$ values, inherent material properties (mobility, interfacial properties, etc.), and the like among the respective layers included in the organic material layer is given.

As already described above, in order to solve the emission problem with a hole transport layer in a recent organic light emitting diode, an auxiliary light emitting layer is preferably formed between the hole transport layer and the light emitting layer, and it is necessary to form different auxiliary light emitting layers corresponding to respective light emitting layers (R, G, B). In other words, among a red auxiliary light emitting layer, a green auxiliary light emitting layer, and a blue auxiliary light emitting layer corresponding to a red light emitting layer, a green light emitting layer, a blue light emitting layer, the auxiliary light emitting layer includes the red auxiliary light emitting layer. Meanwhile, the correlation between the auxiliary light emitting layer and the hole transport layer and the correlation between the auxiliary light emitting layer and the light emitting layer (host) need to be understood, and if a used organic material layer varies even when similar cores are used, the characteristics of the auxiliary light emitting layer are very difficult to infer.

Accordingly, energy levels, $T_1$ values, and inherent material properties (mobility, interfacial properties, etc.), and the like among the respective layers included in the organic material layer are optimized by forming the light emitting layer and/or auxiliary light emitting layer using the compound represented by Formula (1) of the present disclosure, so that both the lifespan and efficiency of an organic electric element can be improved.

An organic electric element according to an embodiment of the present disclosure may be manufactured using various deposition methods. The organic electric element may be manufactured by a physical vapor deposition (PVD) method, a chemical vapor deposition (CVD) method, or the like. For example, The organic electric element may be manufactured by depositing a metal, a metal oxide having conductivity, or an alloy thereof, on the substrate to form the anode 120, forming the organic material layer including the hole injection layer 130, the hole transport layer 140, the light emitting layer 150, the electron transport layer 160, and the electron injection layer 170 thereon, and then depositing a material, which can be used for the cathode 180, thereon. The auxiliary light emitting layer 151 may be formed between the hole transport layer 140 and the light emitting layer 150.

Also, the organic material layer may be manufactured to have a smaller number of layers using various polymer materials by a soluble process or solvent process, for example, a spin coating process, a nozzle printing process, an inkjet printing process, a slot coating process, a dip coating process, a roll-to-roll process, a doctor blading process, a screen printing process, or a thermal transfer method. Since the organic material layer according to the present disclosure may be formed in various ways, the scope of protection of the present disclosure is not limited by a method of forming the organic material layer.

The organic electric element according to an embodiment of the present disclosure may be a top emission type, a bottom emission type, or a dual emission type, according to the used materials.

A white organic light emitting device (WOLED) facilitates the implementation of high resolution, has excellent processability, and has an advantage of being produced using conventional LCD color filter technologies. In this regard, various structures for WOLEDs, mainly used as back light units, have been suggested and patented. Representative WOLEDs are: a parallel side-by-side arrangement of red (R), green (G), and blue (B) light-emitting units on a mutual plane: a stacking arrangement of R, G, and B light emitting layers above and below; and a color conversion material (CCM) structure using electroluminescence from a blue (B) organic light emitting layer and photoluminescence from an inorganic fluorescent body by using the electroluminescence. The present disclosure is applicable to these WOLEDs.

Further, the organic electric element according to an embodiment of the present disclosure may be any one of an organic light emitting diode (OLED), an organic solar cell, an organic photo conductor (OPC), an organic transistor (organic TFT), and an element for monochromatic or white illumination.

Another embodiment of the present disclosure provides an electronic device including: a display device, which includes the above described organic electric element; and a control unit for controlling the display device. Here, the electronic device may be a wired/wireless communication terminal, which is currently used or will be used in the future, and covers all kinds of electronic devices including a mobile communication terminal, such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present disclosure will be described. A compound according to an aspect of the present disclosure is represented by Formula (1) below.

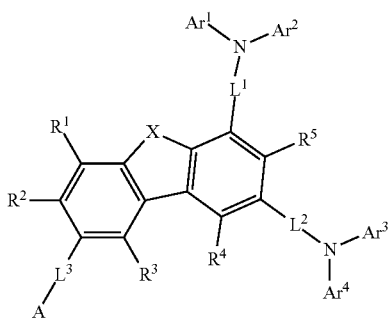

In Formula (1),
1) A may be one of

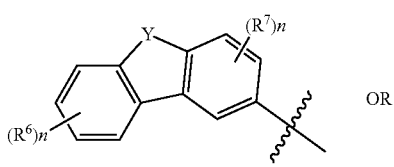

OR

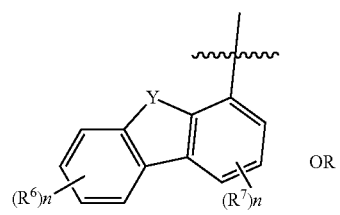

OR

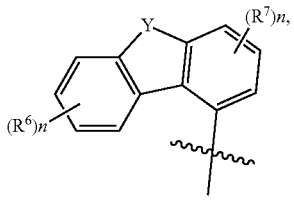

2) X may be O or S,
3) $R^1$, $R^2$, $R^3$, $R^4$, $R^5$, $R^6$, and $R^7$ each may be selected from the group consisting of hydrogen; deuterium; halogen; a $C_6$-$C_{60}$ aryl group; a fluorenyl group; a $C_2$-$C_{60}$ heterocyclic group containing at least one heteroatom of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$) ($R_b$) (wherein, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group, and wherein $R_a$ and $R_b$ each may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one heteroatom of O, N, S, Si, and P). Also, adjacent $R^1$ and $R^2$, a plurality of $R^6$'s, or a plurality of $R^7$'s may be linked to each other to form an aromatic or heteroaromatic ring.

4) $L^1$, $L^2$ and $L^3$ each may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group containing at least one heteroatom of O, N, S, Si, and P. However, at least one of $L^1$, $L^2$ and $L^3$ is the single bond when X is O.

5) $Ar^1$, $Ar^2$, $Ar^3$, $Ar^4$, $Ar^5$, and $Ar^6$ each may be independently selected from the group consisting of a $C_6$-$C_{60}$ aryl group; a fluorenyl group; a $C_2$-$C_{60}$ heterocyclic group containing at least one heteroatom of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$) ($R_b$).

Also, $L^1$, $L^2$, $L^3$, $Ar^1$, $Ar^2$, $Ar^3$, $Ar^4$, $Ar^5$, and $Ar^6$ may be linked between adjacent functional groups to form an aromatic or heteroaromatic ring. For example, $Ar^1$ and $Ar^2$, $Ar^3$ and $Ar^4$, $Ar^5$ and $Ar^6$, $Ar^1$ and $L^1$, $Ar^2$ and $L^1$, $Ar^3$ and $L^2$, $Ar^4$ 와 $L^2$, $Ar^5$ and $L^3$, or $Ar^6$ and $L^3$ may be linked to each other to form an aromatic or heteroaromatic ring.

6) Y may be selected from the group consisting of N-L'-R', O, S, and CR'R", wherein R' and R" may be hydrogen; a $C_6$-$C_{60}$ aryl group; a fluorenyl group; a $C_3$-$C_{60}$ heterocyclic group; a $C_1$-$C_{50}$ alkyl group; a $C_2$-$C_{60}$ alkenyl group, a $C_6$-$C_{60}$ aryloxy group, and R' and R" may be linked to each other to form a spiro ring. L' may be selected from the group consisting of a single bond; a $C_6$-$C_{60}$ arylene group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one heteroatom of O, N, S, Si, and P.

7) n is an integer of 0 to 4, and m is an integer of 0 to 3.

The compound represented by Formula (1) above may be represented by one of the Formulas (2) to (4) below.

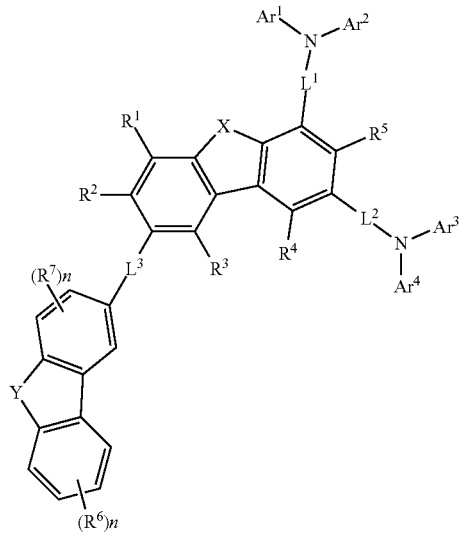

Formula (2)

-continued

Formula (3)

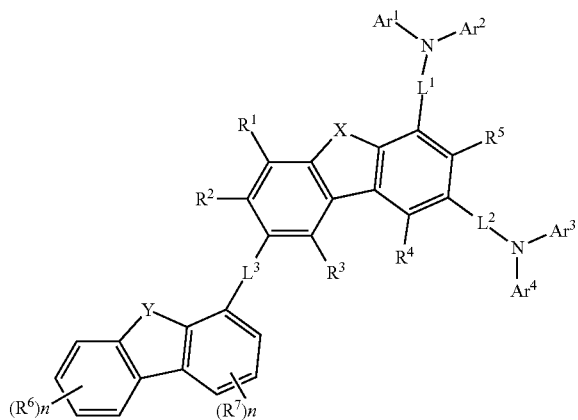

Formula (4)

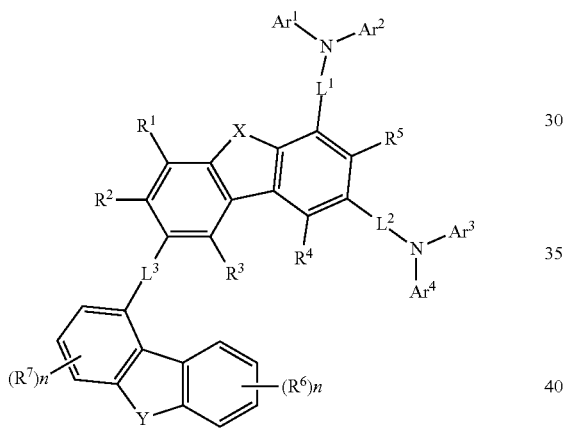

In Formulas (2) to (4),
$R^1, R^2, R^3, R^4, R^5, R^6, R^7$, m, n, $L^1, L^2, Ar^1, Ar^2, Ar^3, Ar^4$, X, and Y may be the same as $R^1, R^2, R^3, R^4, R^5, R^6, R^7$, m, n, $L^1, L^2, L^3, Ar^1, Ar^2, Ar^3, Ar^4$, X, and Y defined in Formula (1) above, respectively.

Here, the aryl group, fluorenyl group, heterocyclic group, fused ring group, alkyl group, alkenyl group, alkynyl group, alkoxy group, aryloxy group, alkylene group, arylene group, fluorenylene group, carbonyl group, arylalkyl group, alkenyloxy group, ether group, alkenylaryl group, cycloalkyl group, silane group, siloxane group, arylalkoxy group, arylalkenyl group, and alkoxycarbonyl group each may be further substituted with at least one substituent selected from the group consisting of deuterium, halogen, a silane group, a siloxane group, a boron group, a germanium group, a cyano group, a nitro group, -$L^b$-N($R^e$) ($R^f$) (here, $L^b$, $R^e$, $R^f$ may be the same as $L^a$, $R^c$ and $R^d$ defined above, respectively), a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, a $C_8$-$C_{20}$ arylalkenyl group, a carbonyl group, an ether group, a $C_2$-$C_{20}$ alkoxycarbonyl group, $C_6$-$C_{30}$ aryloxy group, —O—Si($R^g$)$_3$, and $R^hO$—Si($R^g$)$_2$— (here, $R^g$ may be the same as $R^a$ defined above, and $R^h$ may be the same as $R^b$ defined above).

Here, the aryl group may be an aryl group having 6-60 carbon atoms, preferably 6-40 carbon atoms, and more preferably 6-30 carbon atoms; the heterocyclic group may be a heterocyclic group having 2-60 carbon atoms, preferably 2-30 carbon atoms, and more preferably 2-20 carbon atoms; and the alkyl group may be an alkyl group having 1-50 carbon atoms, preferably 1-30 carbon atoms, more preferably 1-20 carbon atoms, and especially preferably 1-10 carbon atoms.

In the foregoing aryl or arylene group, the aryl or arylene group may be independently a phenyl group, a biphenyl group, a terphenyl group, a naphthyl group, or a phenanthryl group, or a phenylene group, a biphenylene group, a terphenylene group, a naphthylene group, or a phenanthrylene group.

More specifically, the compound represented by Formula (1) may be one of the compounds below, but is not limited to the compounds below.

P-1

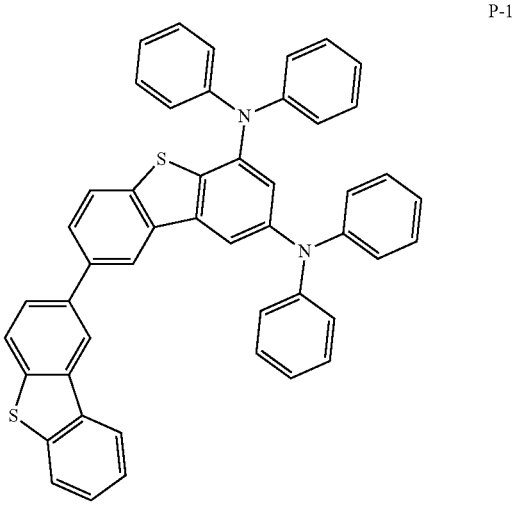

P-2

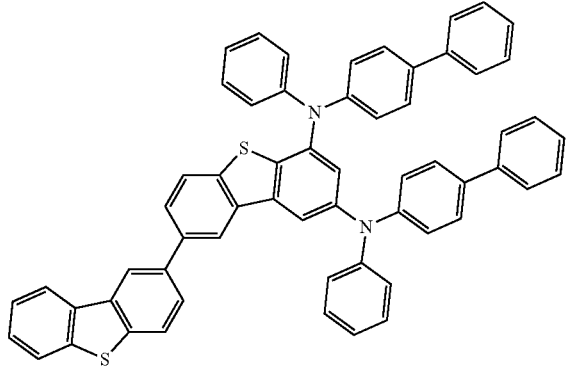

P-3
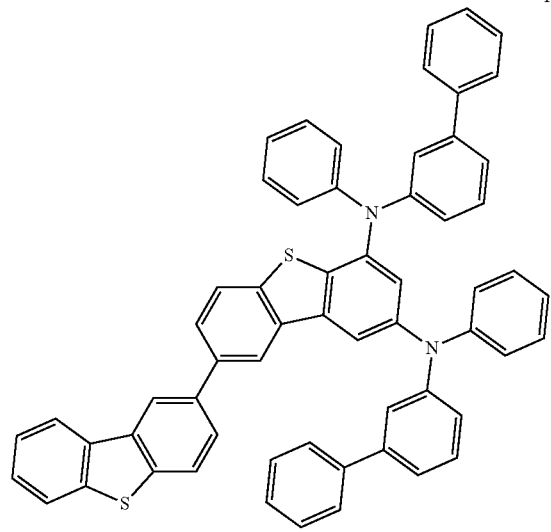
P-4
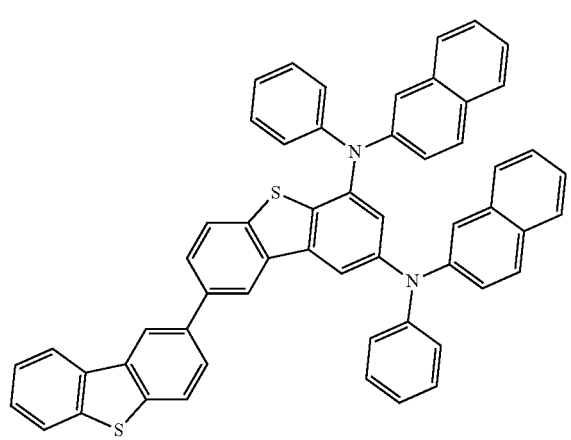
P-5
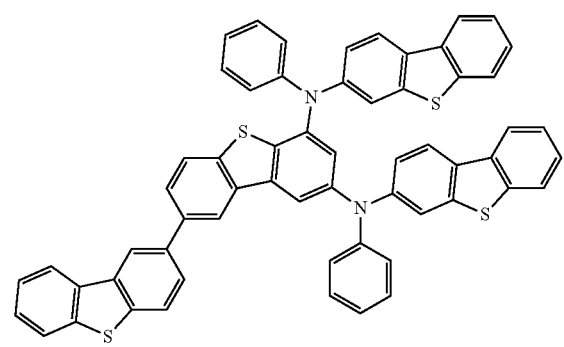
P-6
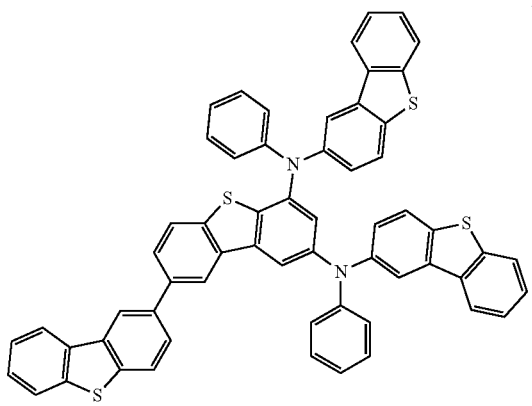
P-7
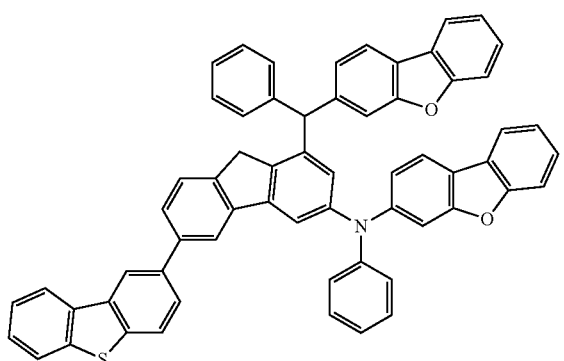
P-8
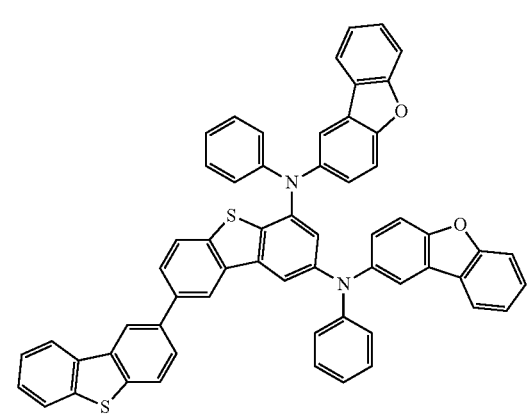
P-9
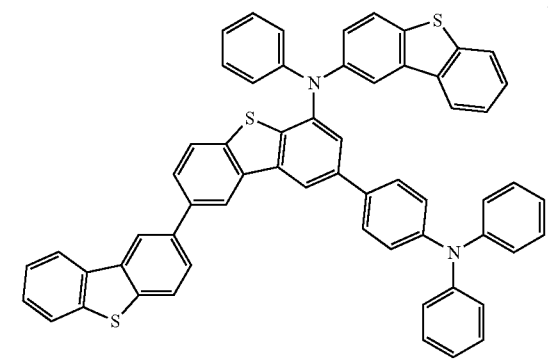

P-10
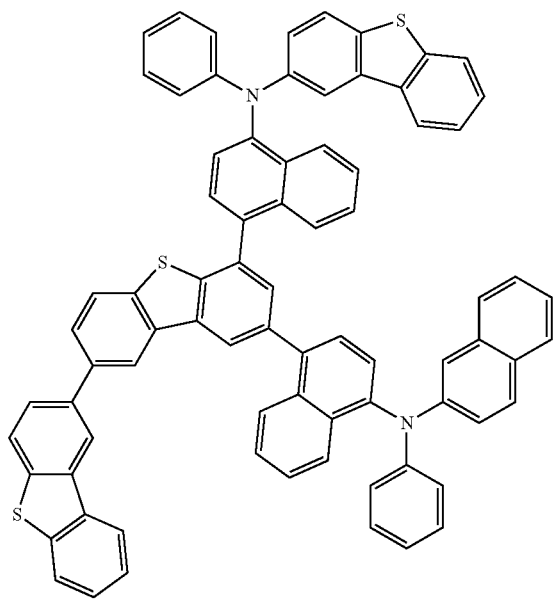
P-11
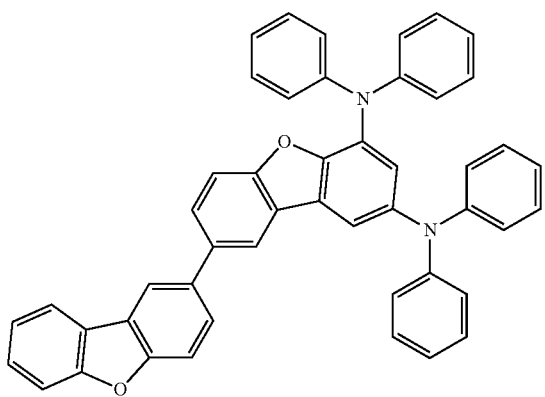
P-12
P-13
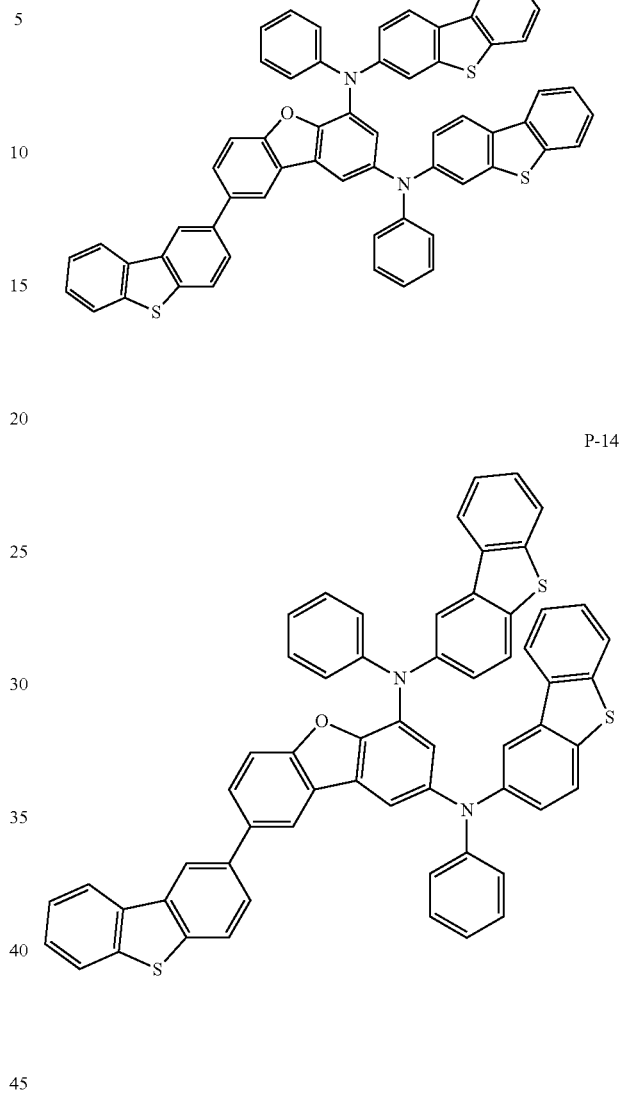
P-14
P-15
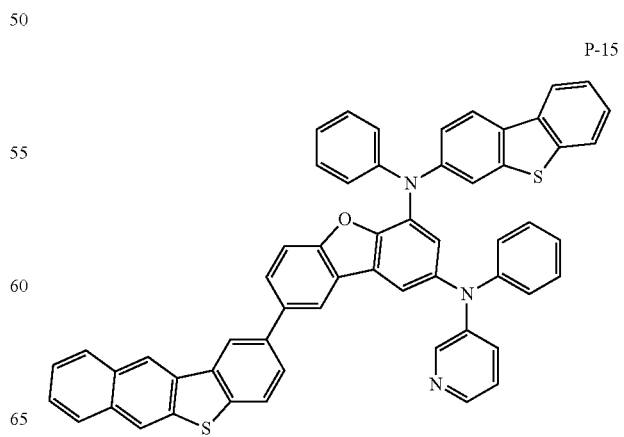

P-16
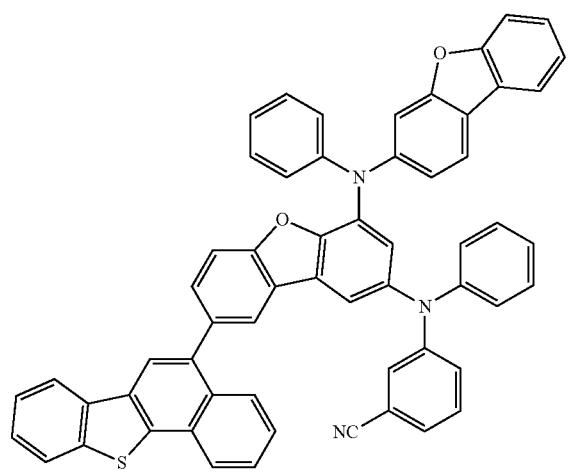
P-17
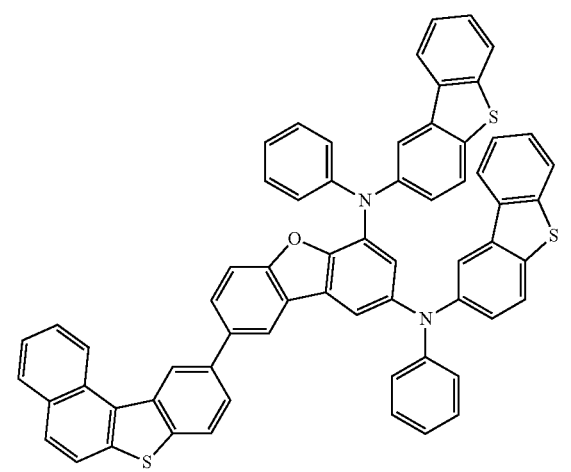
P-18
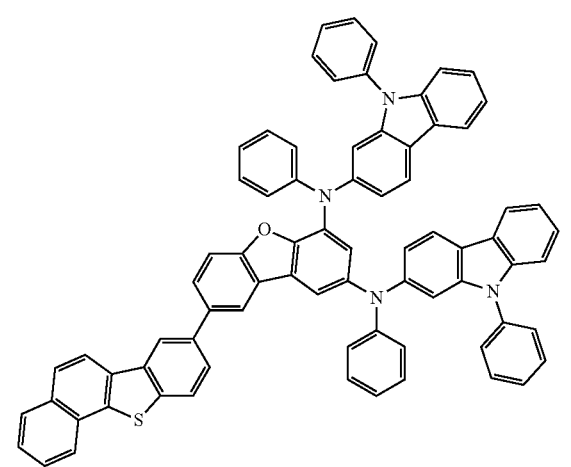
P-19
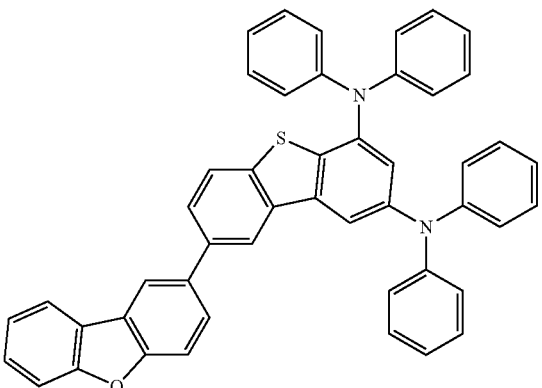
P-20
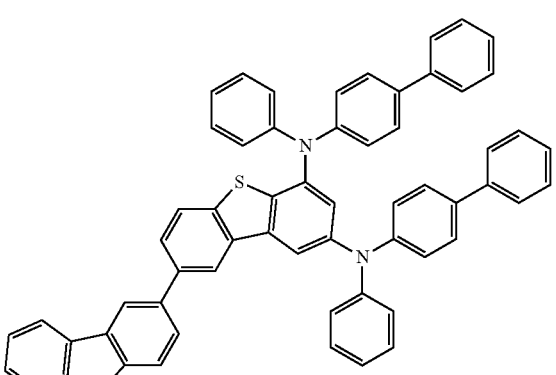
P-21
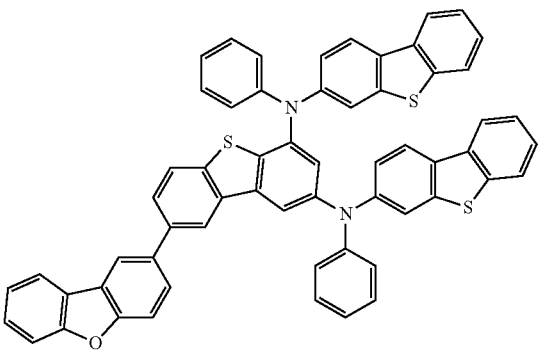
P-22
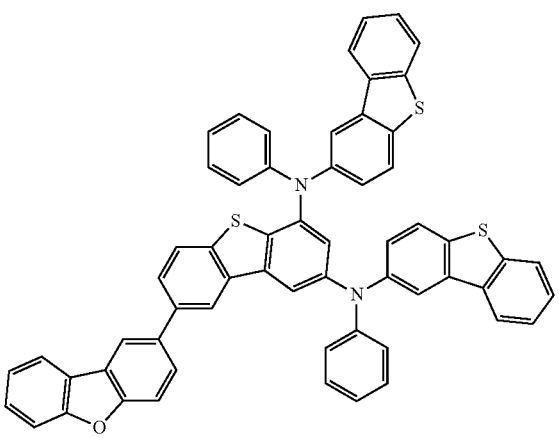

P-23
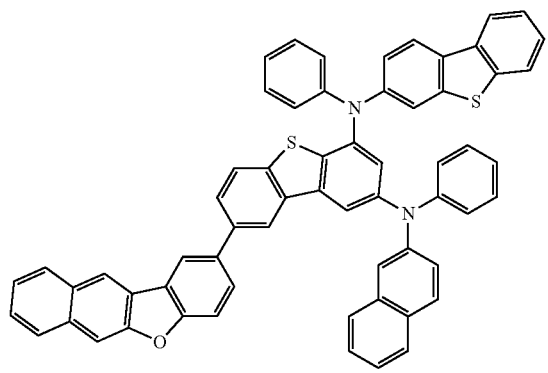
P-24
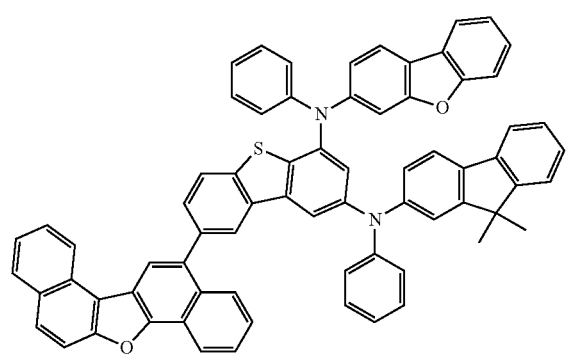
P-25
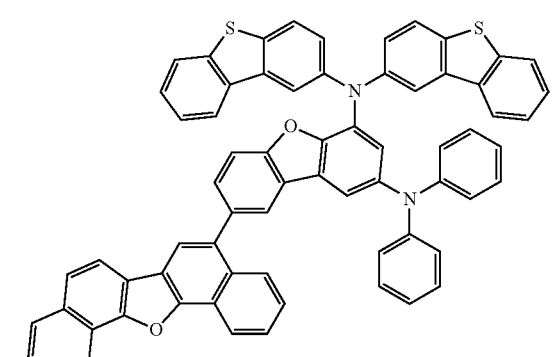
P-26
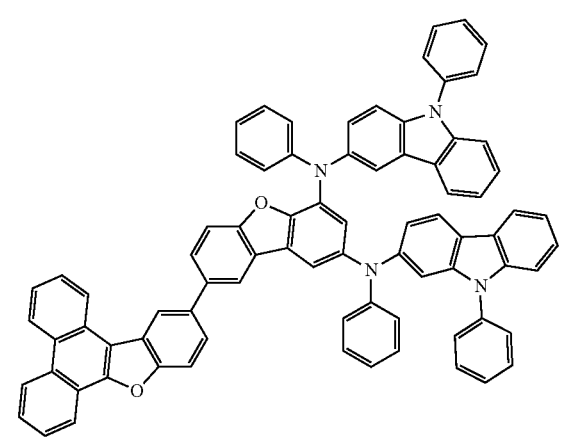
P-27
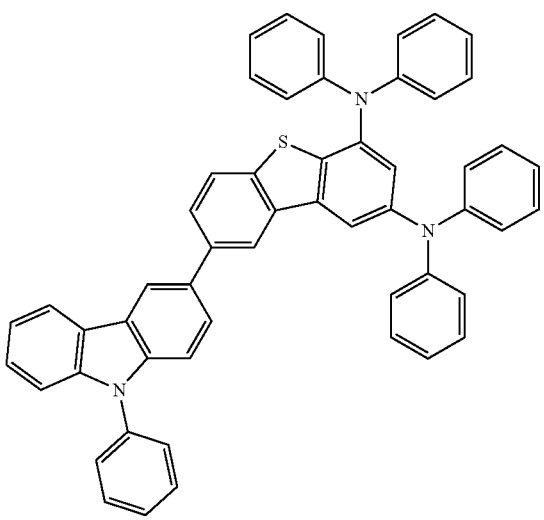
P-28
P-29
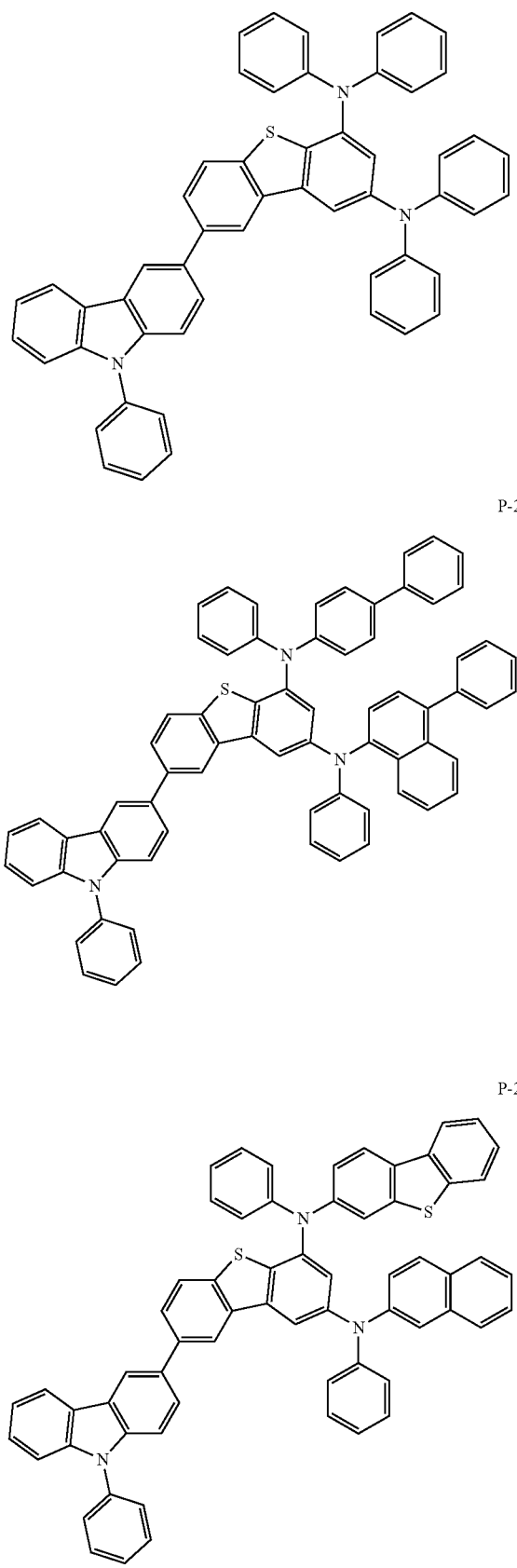

P-30
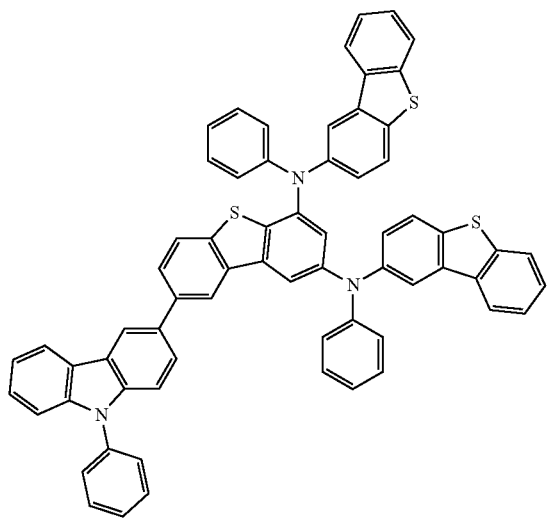
P-31
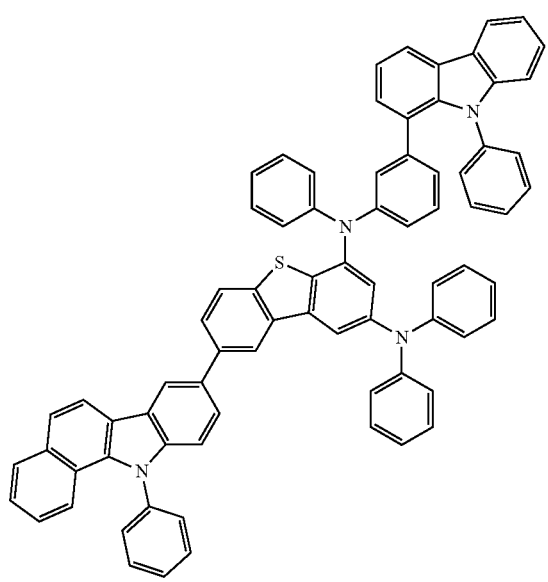
P-32
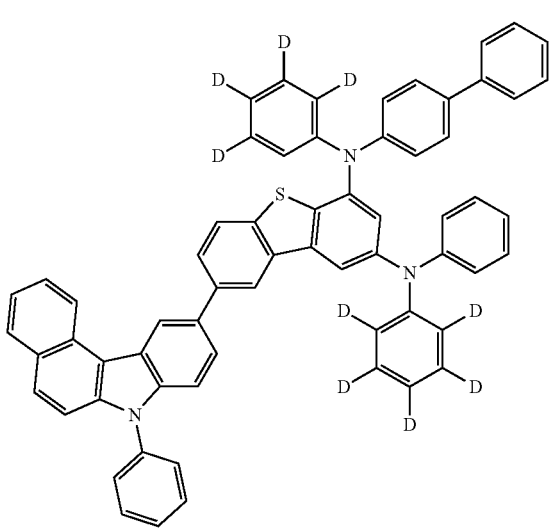
P-33
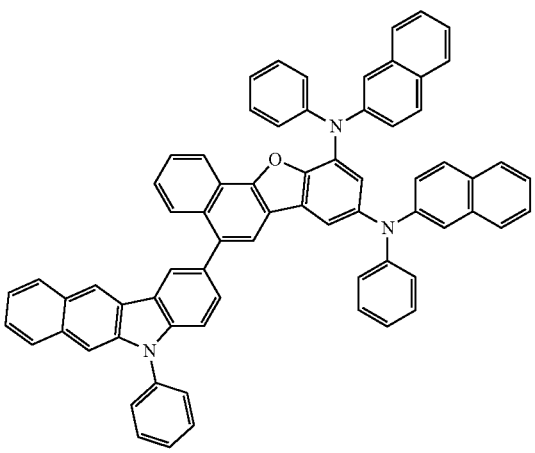
P-34
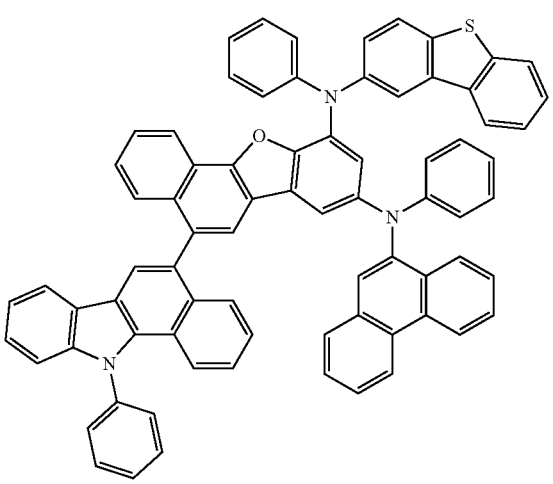
P-35
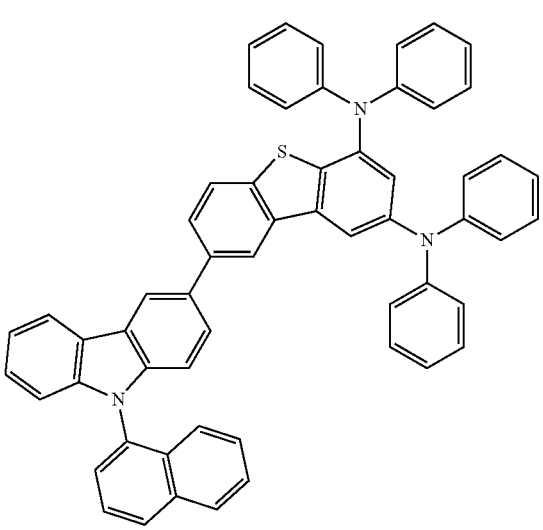

P-36
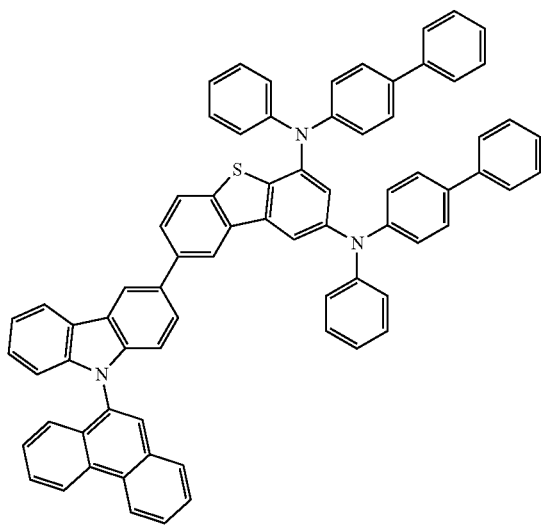
P-37
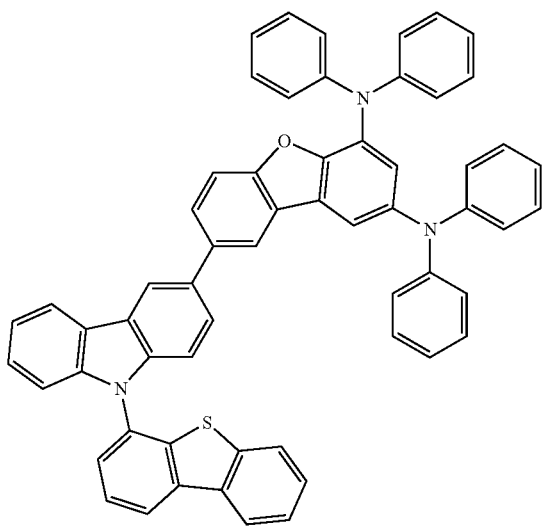
P-38
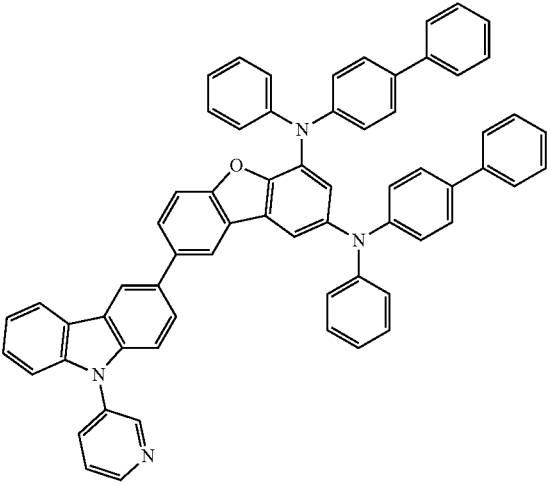
P-39
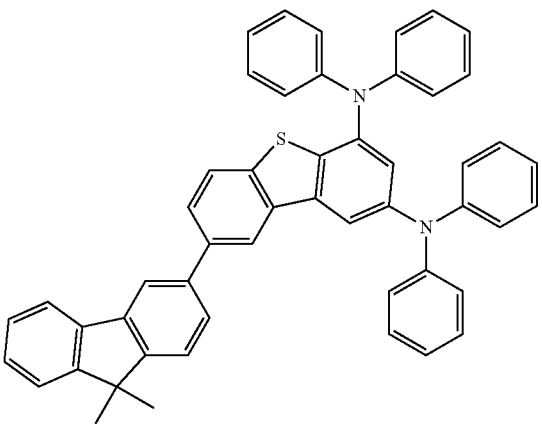
P-40
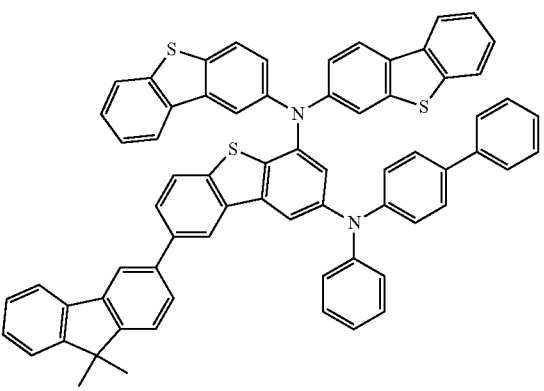
P-41
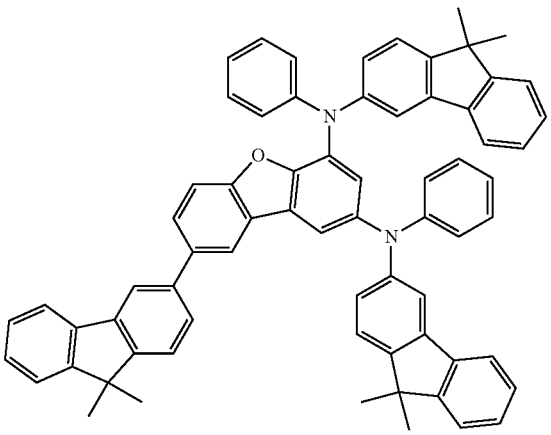

P-42
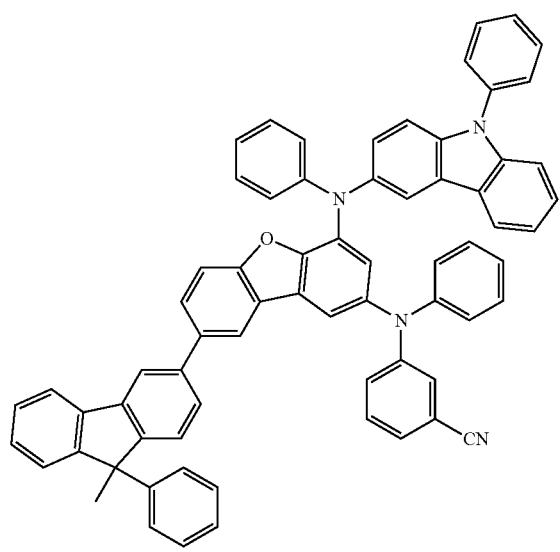
P-43
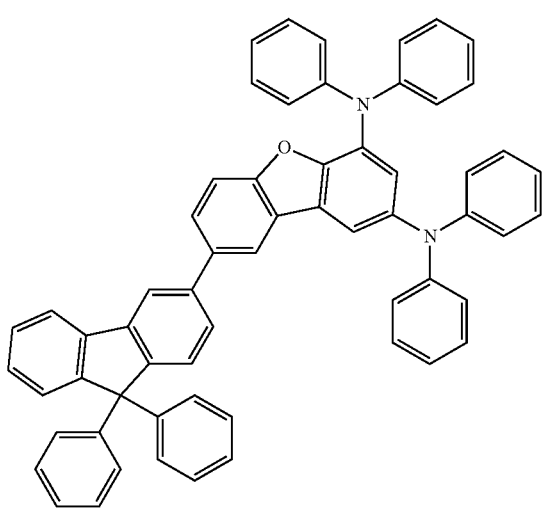
P-44
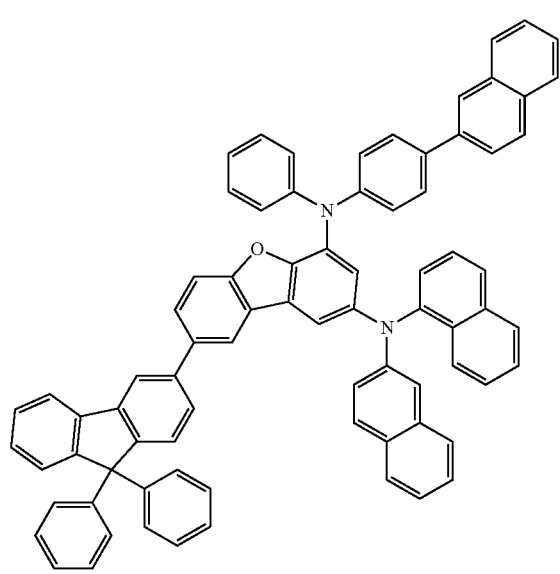
P-45
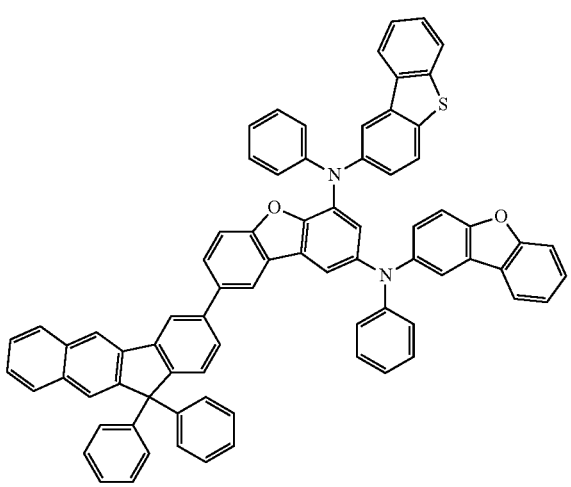
P-46
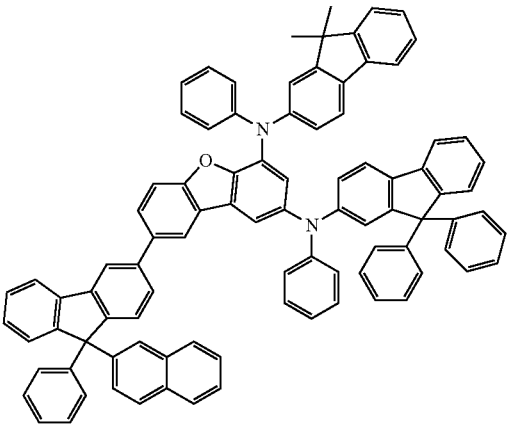
P-47
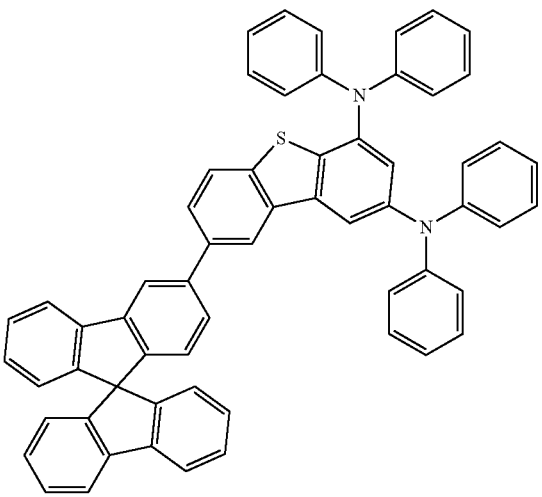

-continued
P-48
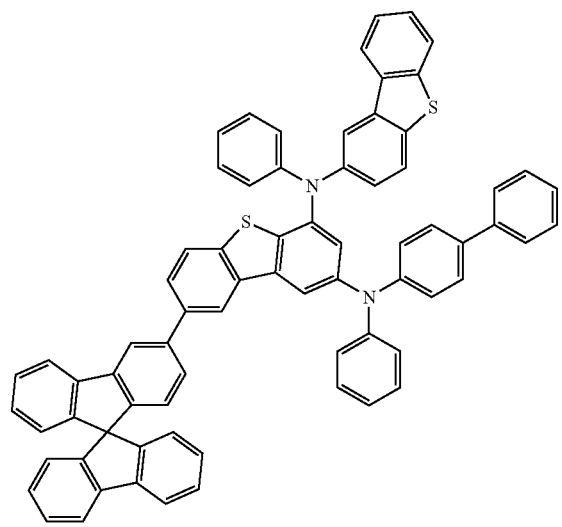
P-49
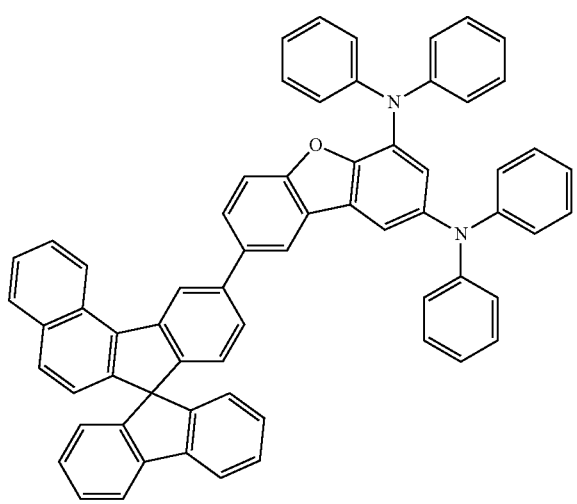
P-50
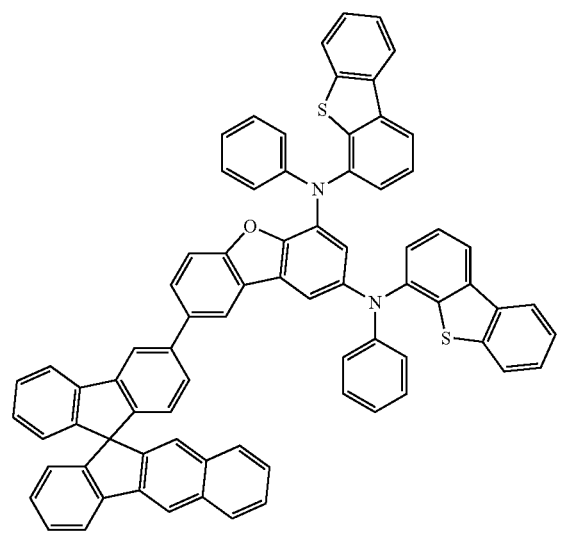
-continued
P-51
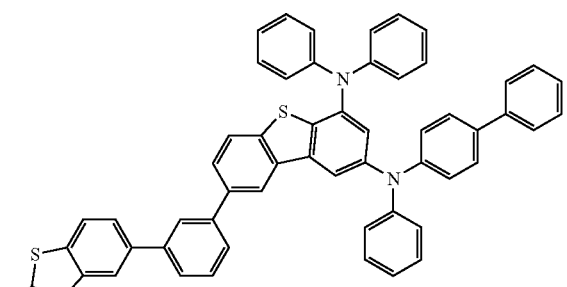
P-52
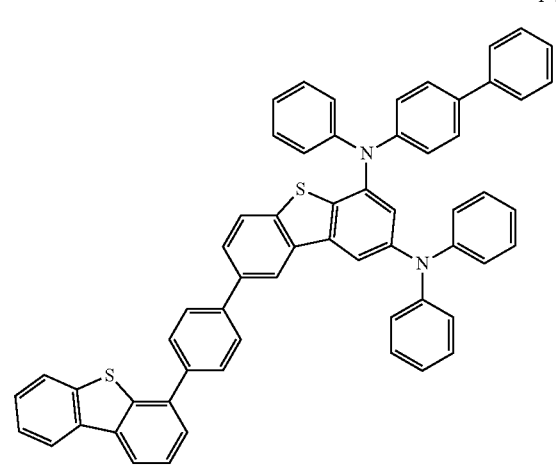
P-53
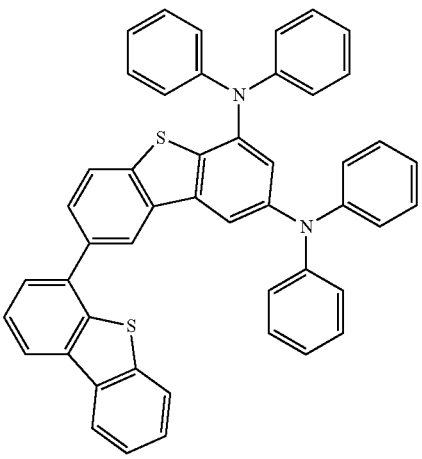

P-54
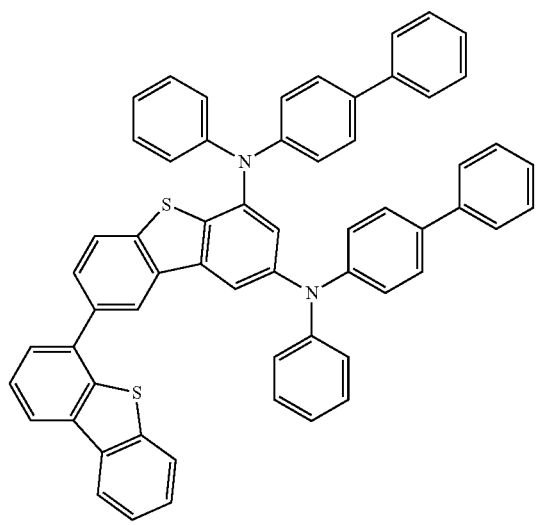
P-55
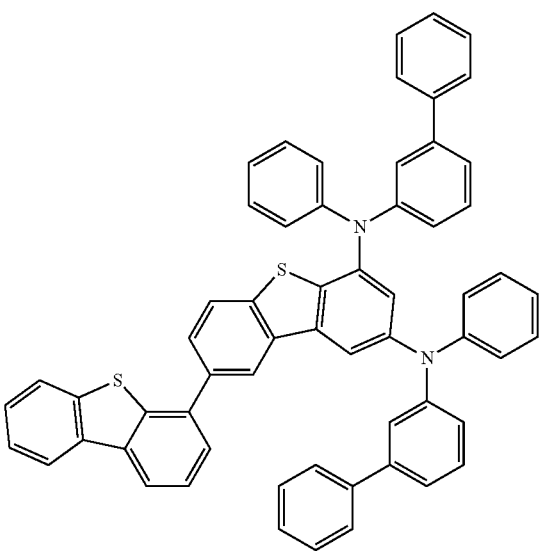
P-56
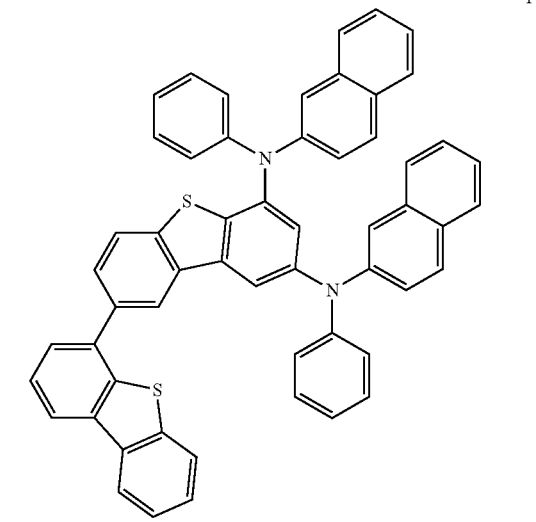
P-57
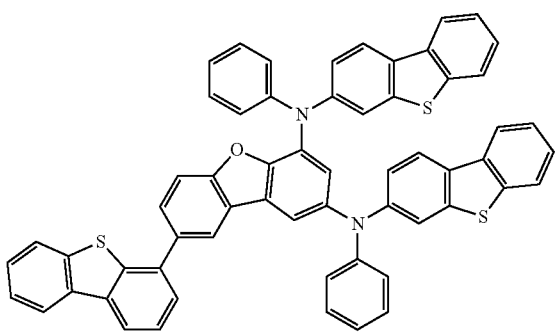
P-58
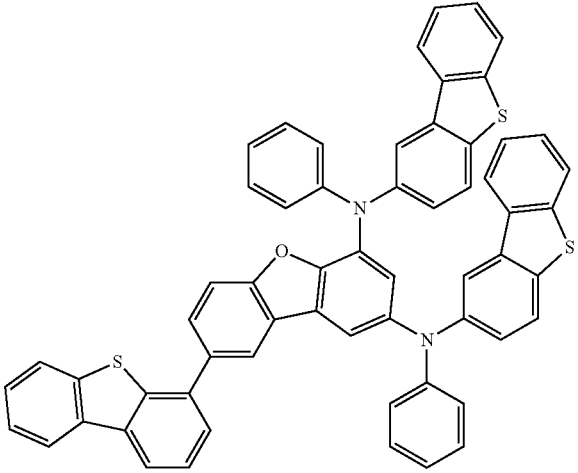
P-59
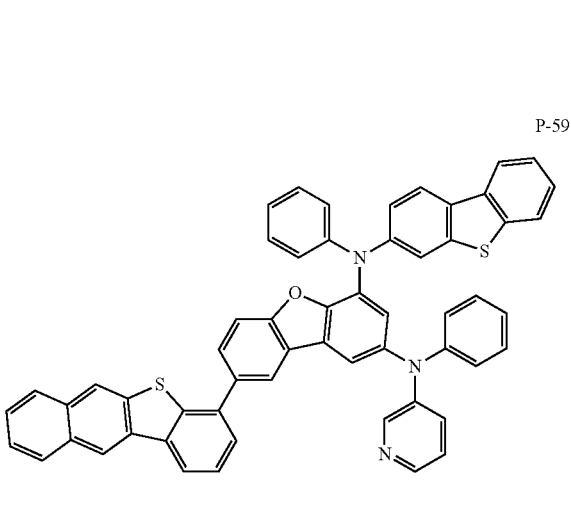

-continued
P-60
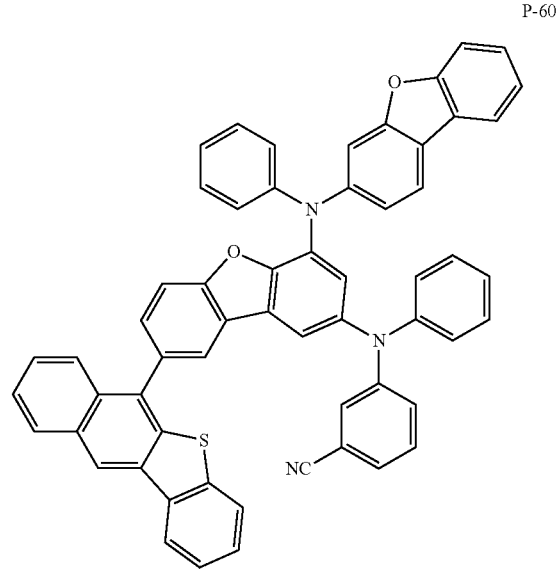
P-61
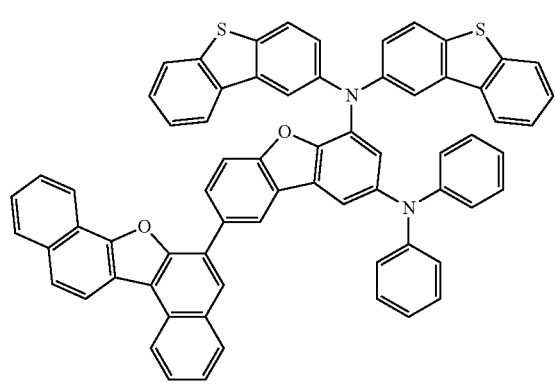
P-62
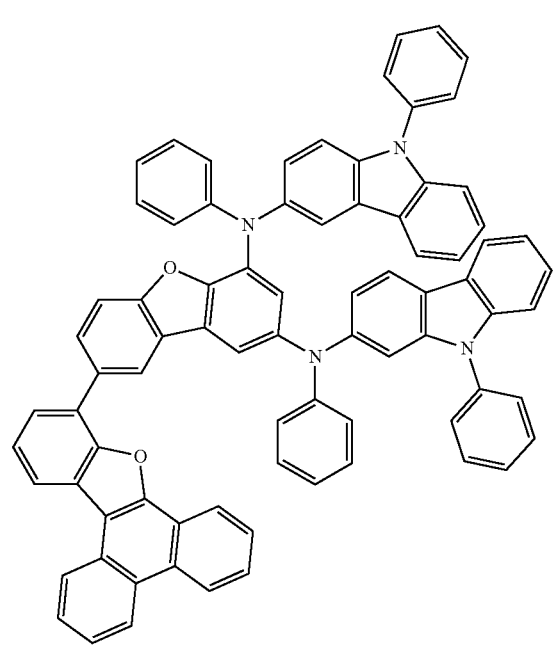
-continued
P-63
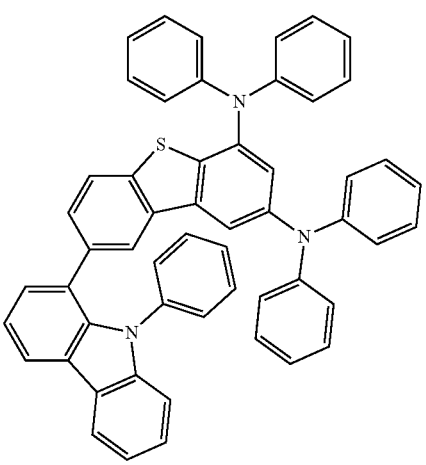
P-64
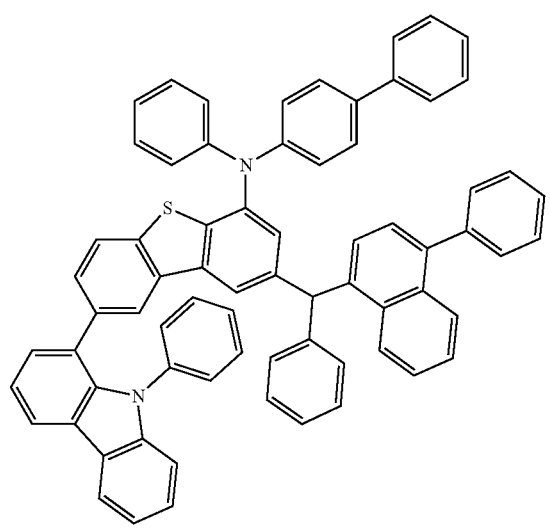
P-65
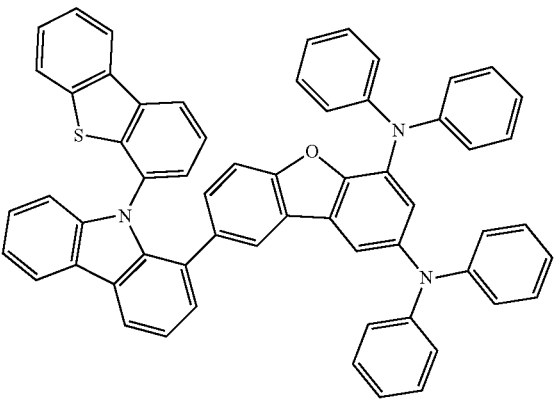

P-66
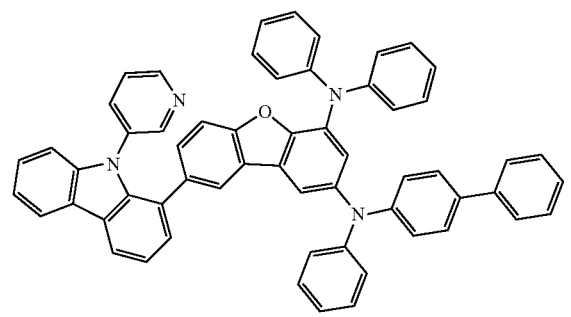
P-67
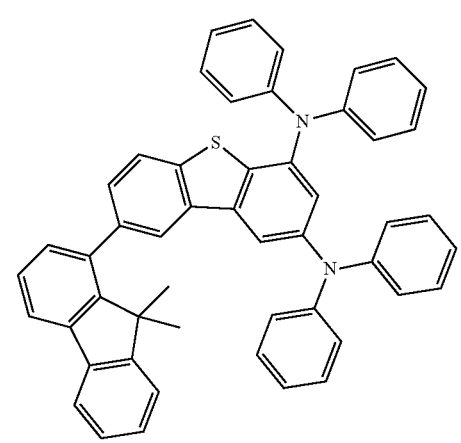
P-68
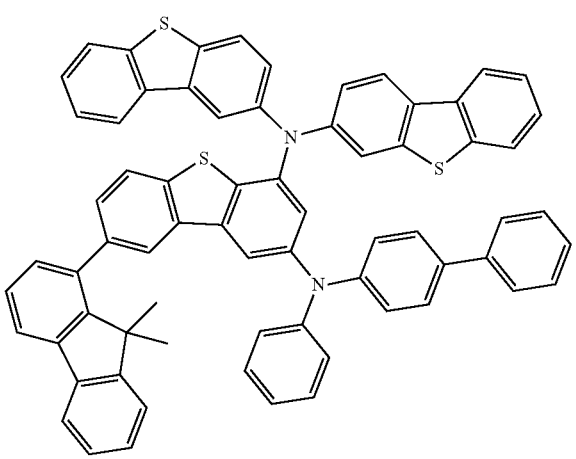
P-69
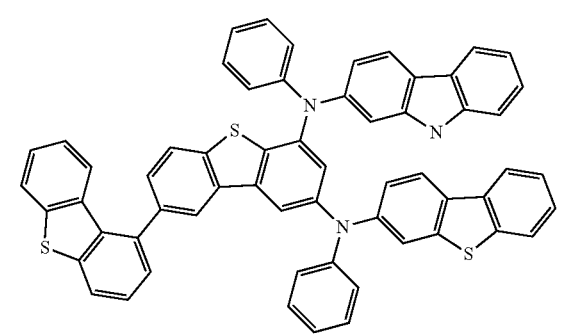
P-70
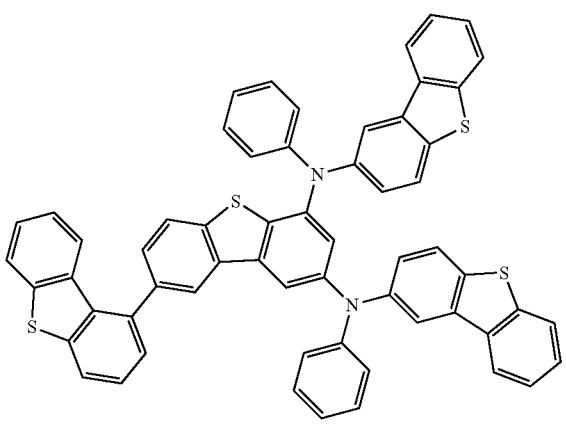
P-71
P-72

P-73
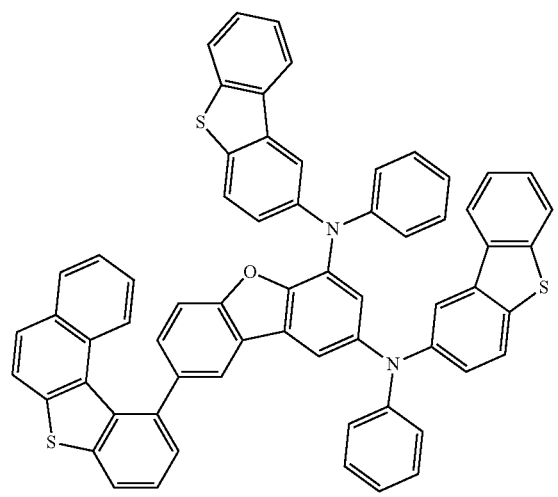
P-74
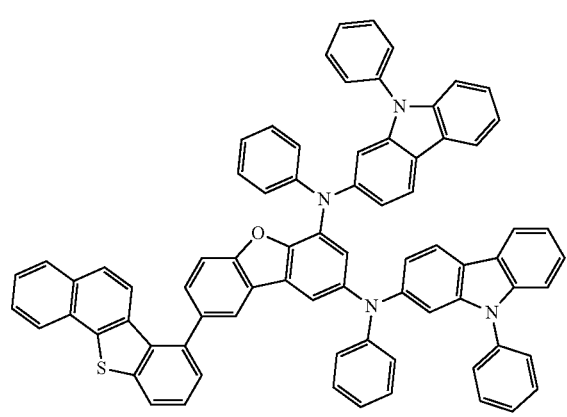
P-75
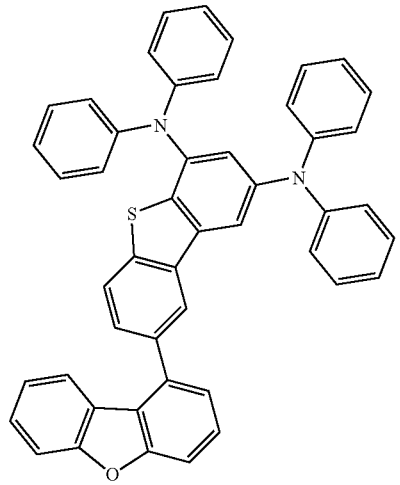
P-76
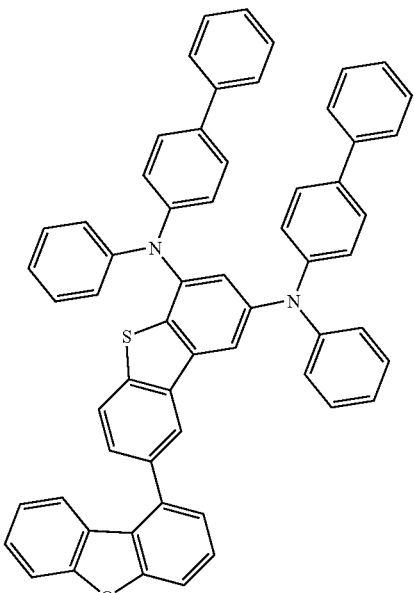
P-77
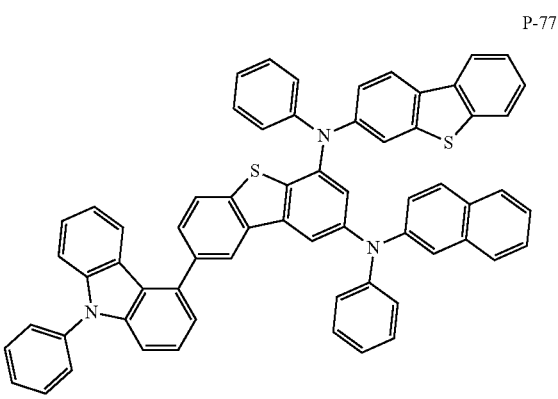
P-78
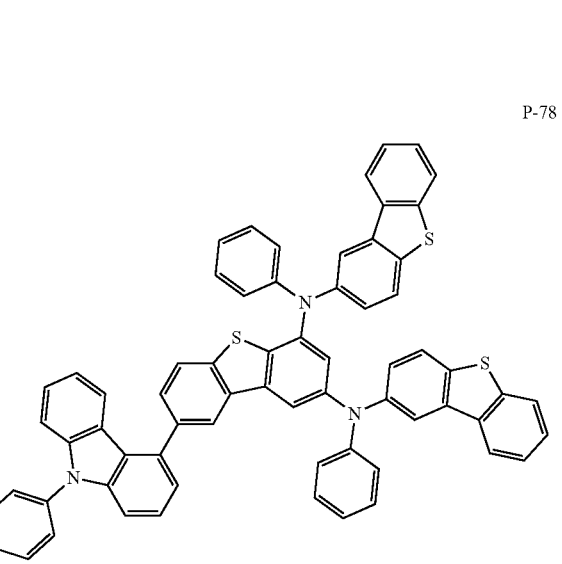

P-79
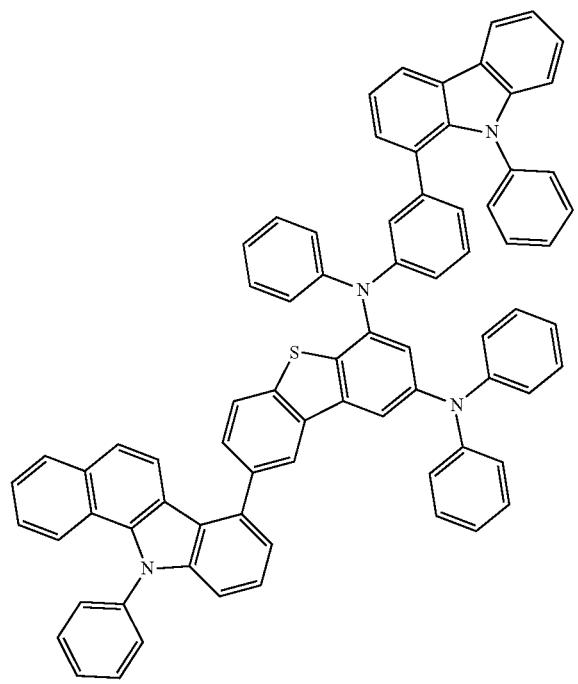
P-81
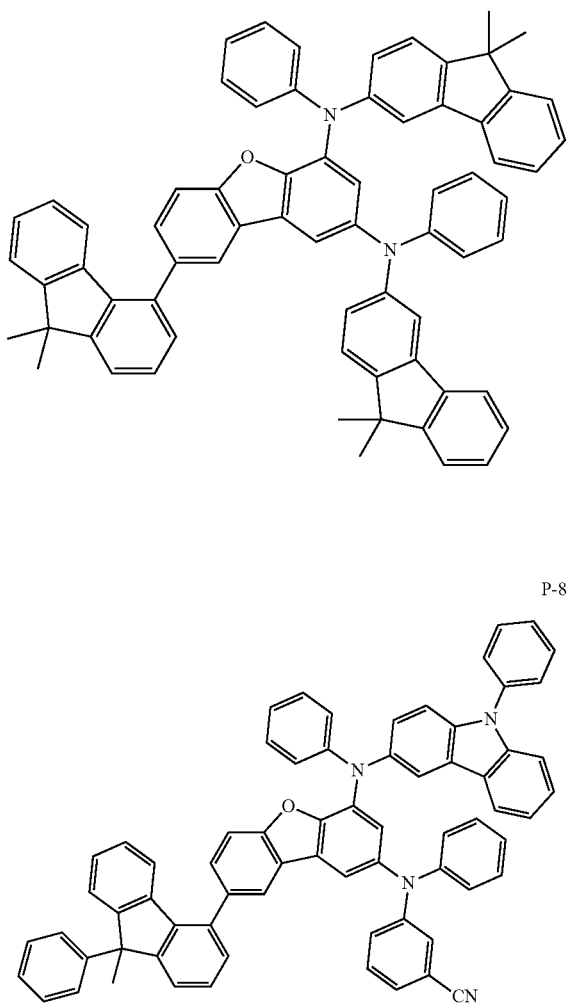
P-82
P-80
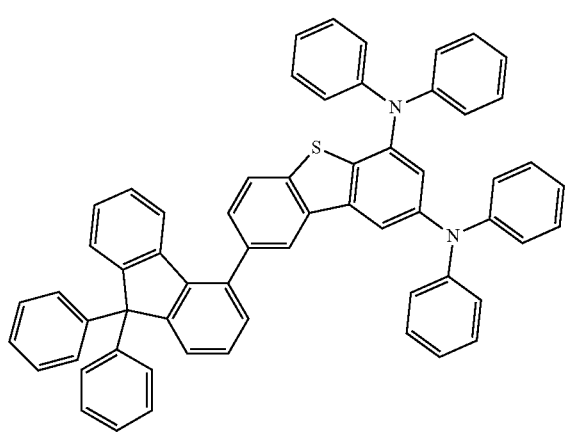
P-83

-continued

P-84

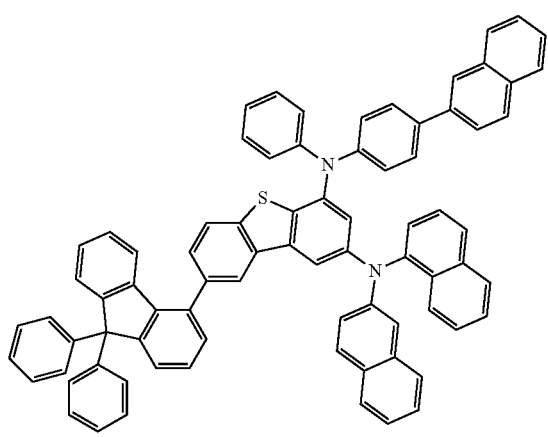

In another embodiment, the present disclosure provides a compound for an organic electric element, represented by Formula (1).

In still another embodiment, the present disclosure provides an organic electric element containing the compound represented by Formula (1).

Here, the organic electric element may include: a first electrode; a second electrode; and an organic material layer positioned between the first electrode and the second electrode, wherein the organic material layer may contain a compound represented by Formula (1), and the compound represented by Formula (1) may be contained in at least one of a hole injection layer, a hole transport layer, an auxiliary light emitting layer, a light emitting layer, an electron transport layer, and an electron injection layer, of the organic material layer. Especially, the compound represented by Formula (1) may be contained in the hole transport layer or the auxiliary light emitting layer.

That is, the compound represented by Formula (1) may be used as a material for a hole injection layer, a hole transport layer, an auxiliary light emitting layer, a light emitting layer, an electron transport layer, or an electron injection layer. Especially, the compound represented by Formula (1) may be used as a material for the hole transport layer or the auxiliary light emitting layer. The present disclosure provides, specifically, an organic electric element including an organic material layer containing one of the compounds represented by Formula (1), and more specifically, organic electric elements including organic material layers containing the compounds represented by the above individual Formulas (P-1 to P-84). Among a red auxiliary light emitting layer, a green auxiliary light emitting layer, and a blue auxiliary light emitting layer corresponding to a red light emitting layer, a green light emitting layer, and a blue light emitting layer, the compound represented by Formula (1) may be used in the red auxiliary light emitting layer.

In still another embodiment, the present disclosure provides an organic electric element, characterized in that the compound is contained alone, two or more different kinds of the compounds are contained as a combination, or the compound is contained together with other compounds as a combination of two or more in at least one of the hole injection layer, the hole transport layer, the auxiliary light emitting layer, the light emitting layer, the electron transport layer, and the electron injection layer, of the organic material layer. In other words, the compounds corresponding to Formula (1) may be contained alone, a mixture of two or more kinds of compounds of Formula (1) may be contained, or a mixture of the compound of Formula (1) and a compound not corresponding to the present disclosure may be contained in each of the layers. Here, the compounds that do not correspond to the present disclosure may be a single compound or two or more kinds of compounds. Here, when the compound is contained together with other compounds as a combination of two or more kinds of compounds, the other compounds may be a compound that is already known for each organic material layer, or a compound to be developed in the future. Here, the compounds contained in the organic material layer may be formed of only the same kind of compounds, or a mixture of two or more kinds of different compounds represented by Formula (1).

For example, the organic material layer may be prepared by mixing two compounds having different structures among the above compounds at a molar ratio of 99:1 to 1:99.

In still another embodiment of the present disclosure, the present disclosure provides an organic electric element further including a light efficiency improvement layer, which is formed on at least one between one surface of the first electrode, which is the opposite side to the organic material layer, and one surface of the second electrode, which is the opposite side to the organic material layer.

Hereinafter, synthetic examples of the compound represented by Formula (1) and manufacturing examples of the organic electric element according to the present disclosure will be described in detail by way of example. However, the following examples are only for illustrative purposes and are not intended to limit the scope of the disclosure.

Synthetic Example 1

A compound (final product 1) represented by Formula (1) according to the present disclosure is synthesized by a reaction of Sub 1 and Sub 2 as shown in Reaction Scheme 1 below.

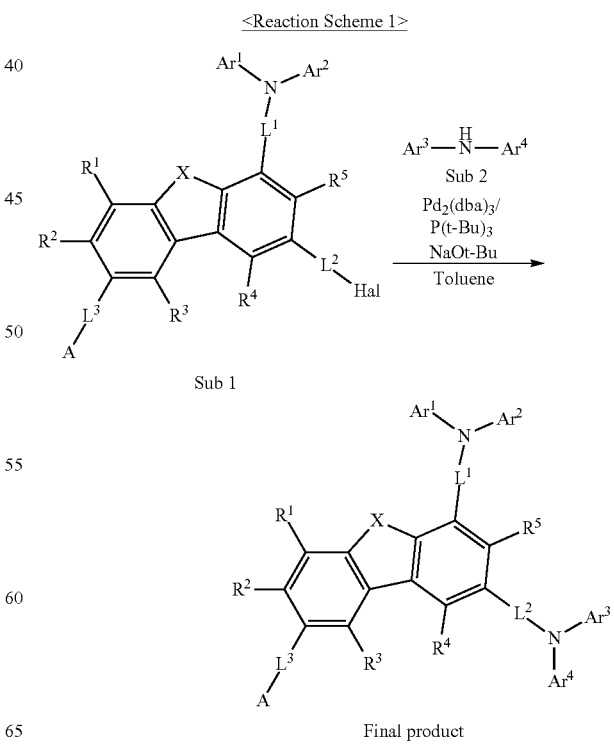

I. Synthesis of Sub 1
Sub 1 in Reaction Scheme 1 above may be synthesized by a reaction pathway of Reaction Scheme 2 below, but is not limited thereto.
A synthetic example of a specific compound included in Sub 1 is as follows.
<Reaction Scheme 2>
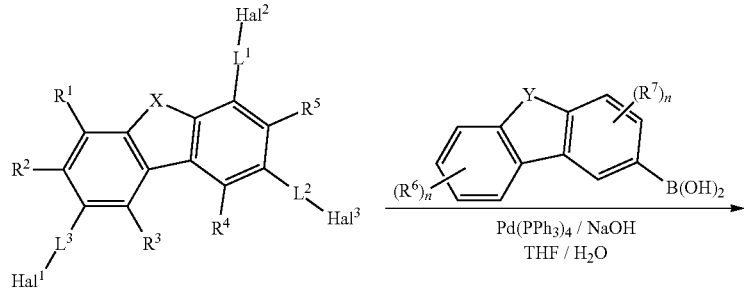
Sub 1-I-1
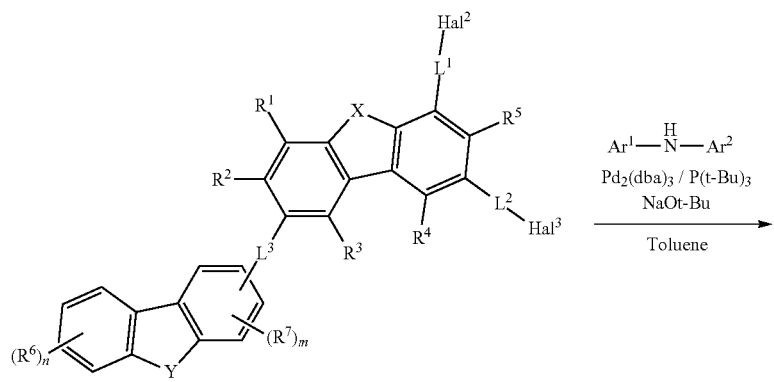
Sub 1-I-2
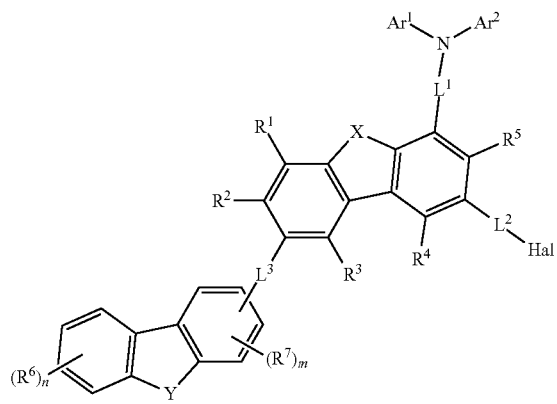
Sub 1-I

Synthetic Example of Sub 1-I

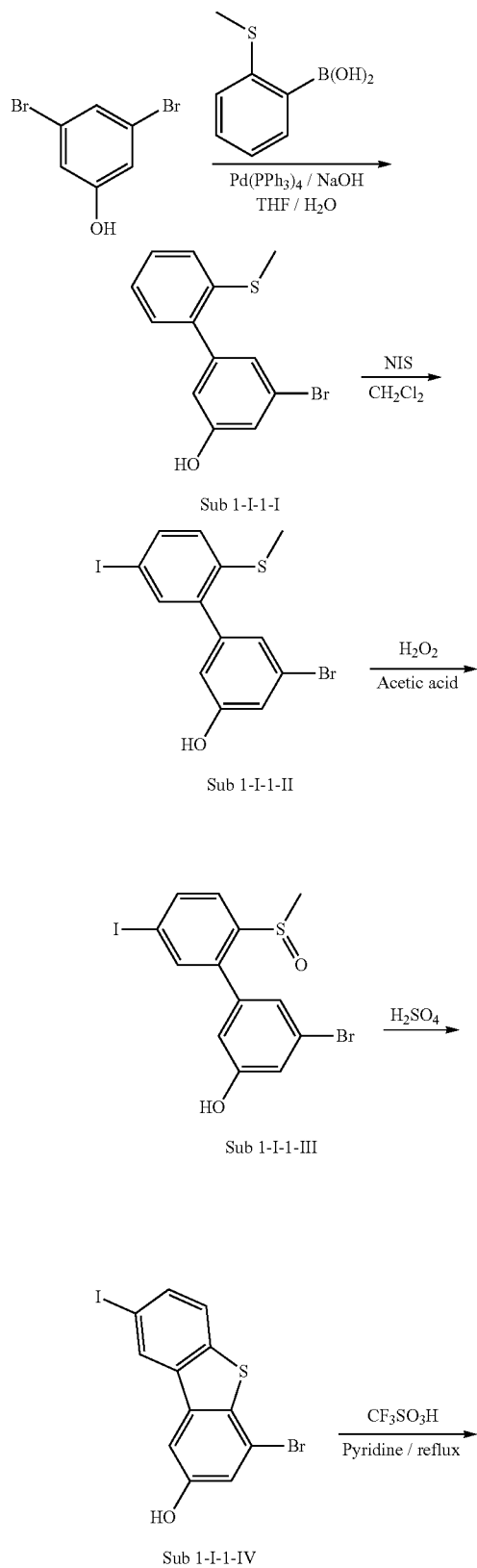

Sub 1-I-1

(1) Synthesis of Sub 1-I-1-I 3,5-Dibromophenol (53.9 g, 213.97 mmol) was dissolved in 1000 mL of THF in a round bottom flask, and then (2-(methylthio)phenyl)boronic acid (35.95 g, 213.97 mmol), Pd(PPh$_3$)$_4$ (7.42 g, 6.42 mmol), NaOH (25.67 g, 641.83 mmol), and water (330 mL) were added. Thereafter, the mixture was stirred at 80□. Upon completion of the reaction, the organic layer was extracted with CH$_2$Cl$_2$ and water, and then the organic layer was dried over MgSO$_4$ and concentrated, and then the compound thus formed was subjected to silica gel column chromatography and recrystallization to give a product (49.5 g, yield: 78.3%).

(2) Synthesis of Sub 1-I-1-II

Sub 1-I-1-I (53.1 g, 204.92 mmol) was dissolved in CH$_2$Cl$_2$ (1000 mL) in a round bottom flask, and then NIS(N-iodosuccinimide (46.1 g, 204.92 mmol) was added, followed by stirring at room temperature for 6 hours. Upon completion of the reaction, the organic layer was separated, dried over MgSO$_4$ and concentrated, and then the compound thus formed was subjected to silica gel column chromatography and recrystallization to give a product (62.2 g, yield: 72%).

(3) Synthesis of Sub 1-I-1-III

Sub 1-I-1-II (45.0 g, 106.87 mmol) was dissolved in acetic acid, and hydrogen peroxide was dropped dropwise thereinto with stirring at room temperature for 6 hours. Upon completion of the reaction, acetic acid was removed by using a decompression device, and then the compound thus formed was separated by using column chromatography to give the desired Sub 1-I-1-III (38.2 g, yield: 82%).

(4) Synthesis of Sub 1-I-1-IV

Sub 1-I-1-III (30.0 g, 68.64 mmol) was dissolved in an excess amount of H$_2$SO$_4$, followed by stirring at room temperature for 6 hours. Upon completion of the reaction, the reaction product was neutralized with NaOH, and extracted with CH$_2$Cl$_2$, followed by concentration, and then the compound thus formed was separated by using column chromatography to give the desired Sub 1-I-1-IV (21.3 g, yield: 82%).

(5) Synthesis of Sub 1-I-1

The Sub 1-I-1-IV (20.0 g, 49.38 mmol) thus obtained was added to an excess amount of trifluoromethane-sulfonic acid, followed by stirring at room temperature for 6 hours. Subsequently, water and pyridine (8:1) were slowly added, followed by reflux for 30 minutes. The temperature was lowered, extracted with CH$_2$Cl$_2$, and wiped with water. A small amount of water was removed with anhydrous MgSO$_4$. After filtration under reduced pressure, the organic solvent was concentrated and the resulting product was separated by column chromatography to give the desired Sub-1-I-1 (19.5 g, yield: 73%).

Synthetic Example of Sub 1-I

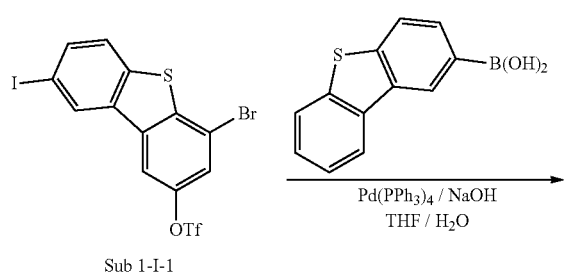

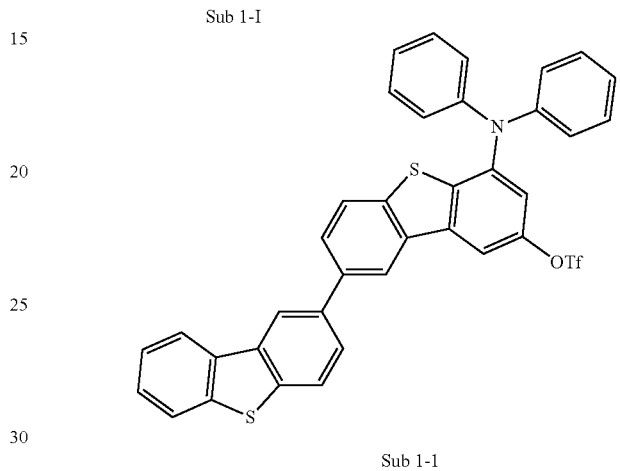

Sub 1-I-1 (42.0 g, 78.20 mmol) and dibenzo[b,d]thiophen-2-ylboronic acid (17.83 g, 78.20 mmol) were subjected to the synthesis method of Sub 1-I-1-I to give a product (39.2 g, yield: 84%).

Synthetic Example of Sub 1-1

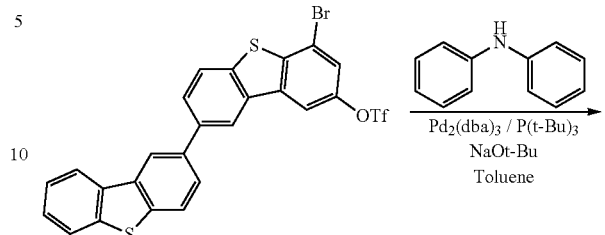

Sub 1-I (16.5 g, 27.8 mmol) was placed in a round bottom flask, and dissolved in toluene (150 mL). Then, diphenylamine (4.71 g, 27.80 mmol), $Pd_2(dba)_3$ (0.76 g, 0.83 mmol), $P(t-Bu)_3$ (0.34 g, 1.67 mmol), and NaOt-Bu (8.20 g, 83.41 mmol) were added in order. Thereafter, the mixture was stirred at 100° C. Upon completion of the reaction, the organic layer was extracted with ether and water, and then the organic layer was dried over $MgSO_4$ and concentrated. The compound thus formed was subjected to silica gel column chromatography and recrystallization to give a product (14.2 g, yield: 75%).

Synthetic Example of Sub 1-6

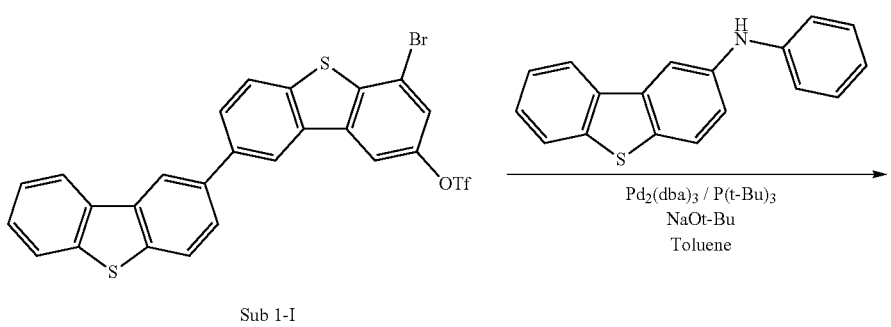

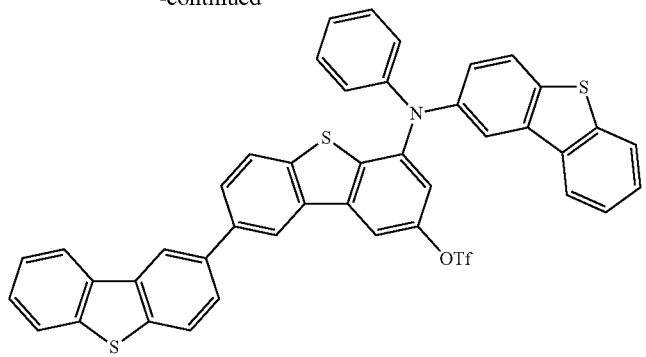
Sub 1-6
Sub 1-I (12.8 g, 21.57 mmol) and N-phenyldibenzo[b,d]thiophen-2-amine (5.94 g, 21.57 mmol) were subjected to the synthesis method of Sub 1-1 to give a product (11.9 g, yield: 71%).
Synthetic Example of Sub 1-9
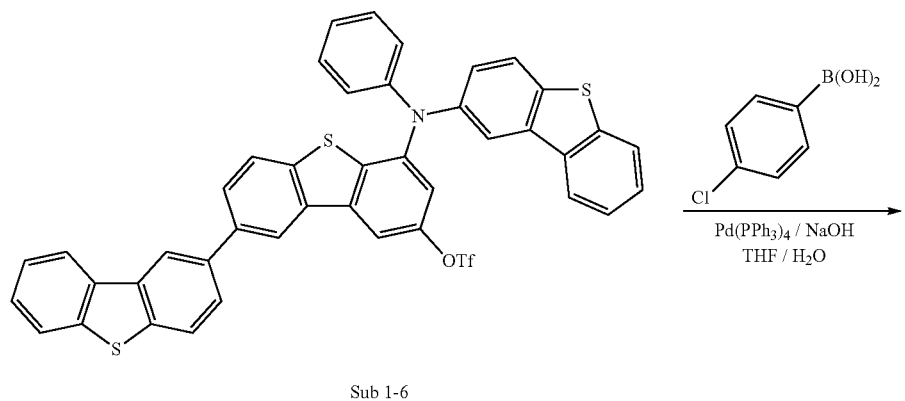
Sub 1-6
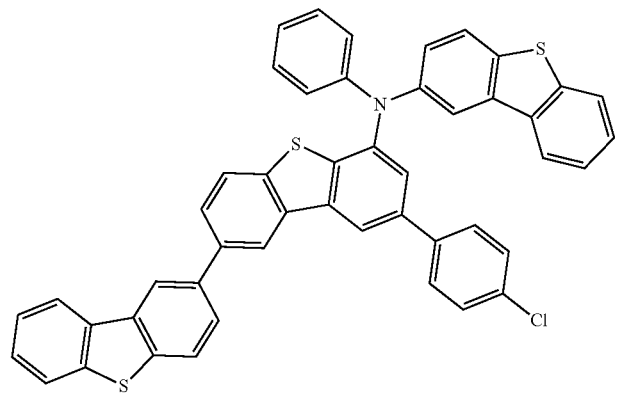
Sub 1-9
Sub 1-6 (21.0 g, 26.65 mmol) and (4-chlorophenyl)boronic acid (4.17 g, 26.65 mmol) were subjected to the synthesis method of Sub 1-I-1-I to give a product (14.8 g, yield: 74%).

Synthetic Example of Sub 1-18
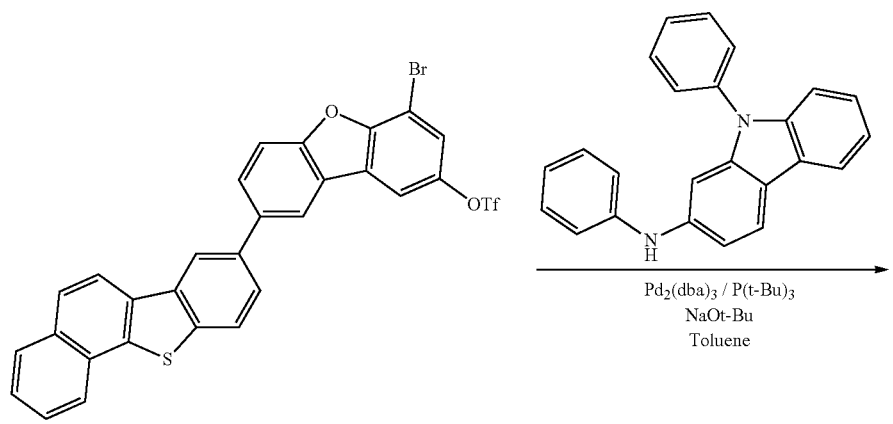
Sub 1-II
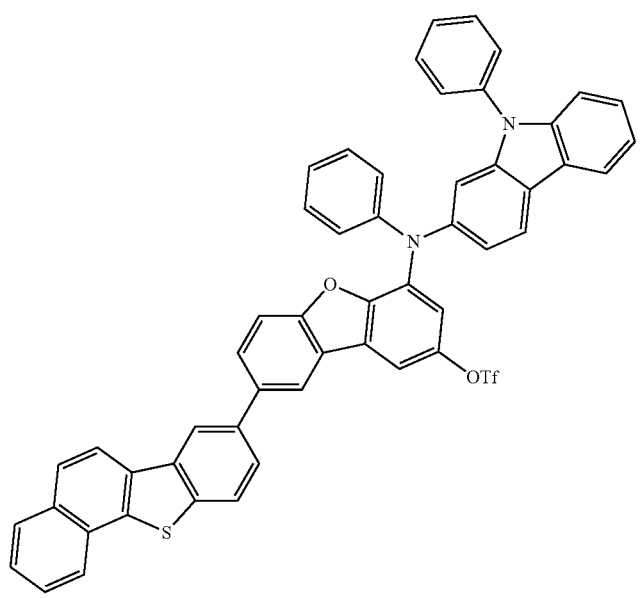
Sub 1-18
Sub 1-II (16.2 g, 25.82 mmol) and N,9-diphenyl-9H-carbazol-2-amine (8.63 g, 25.82 mmol) were subjected to the synthesis method of Sub 1-1 to give a product (16.3 g, yield: 72%).

Synthetic Example of Sub 1-34
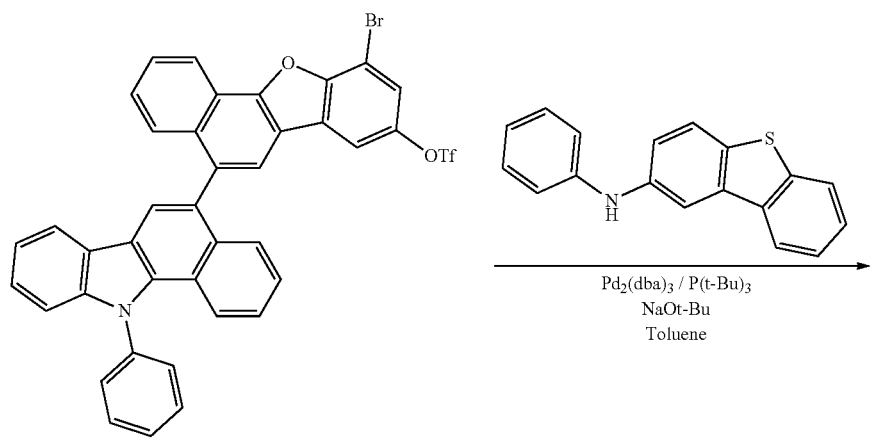
Sub 1-III
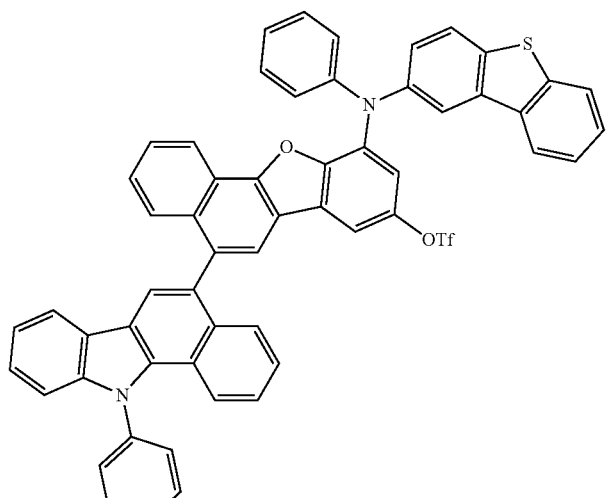
Sub 1-34
Sub 1-III (13.3 g, 18.06 mmol) and N N-phenyldibenzo[b,d]thiophen-2-amine (4.97 g, 18.06 mmol) were subjected to the synthesis method of Sub 1-1 12.5 g to give a product (12.5 g, yield: 74%).
Examples of Sub 1 are as follows, but are not limited thereto.

Sub 1-1
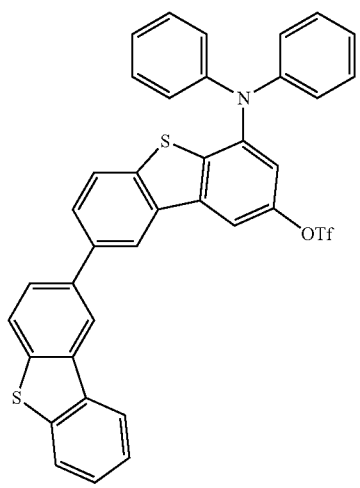
Sub 1-2
Sub 1-3
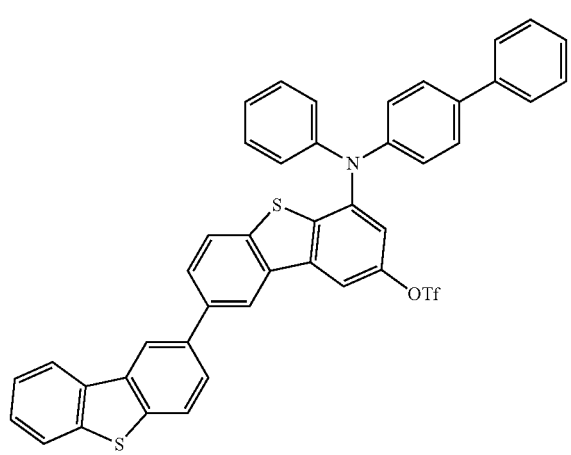
Sub 1-4
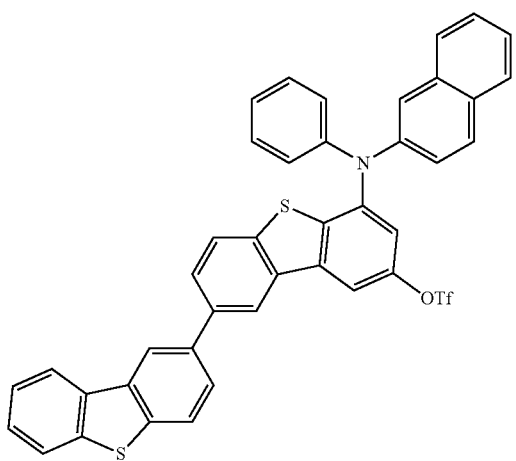
Sub 1-5
Sub 1-6
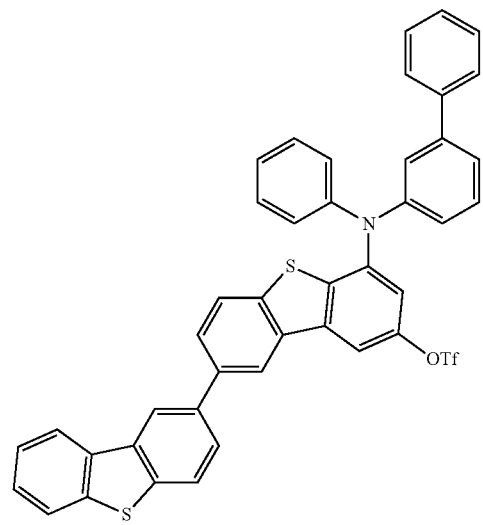

Sub 1-7
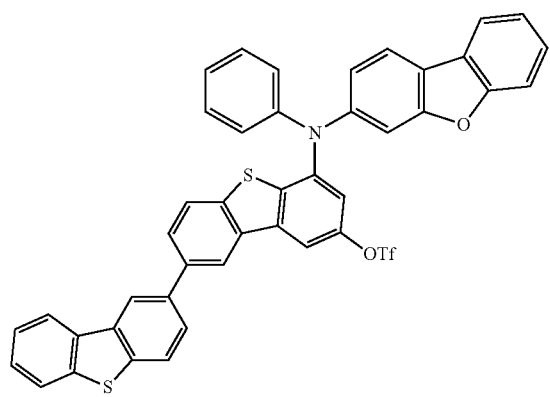
Sub 1-8
Sub 1-9
Sub 1-10
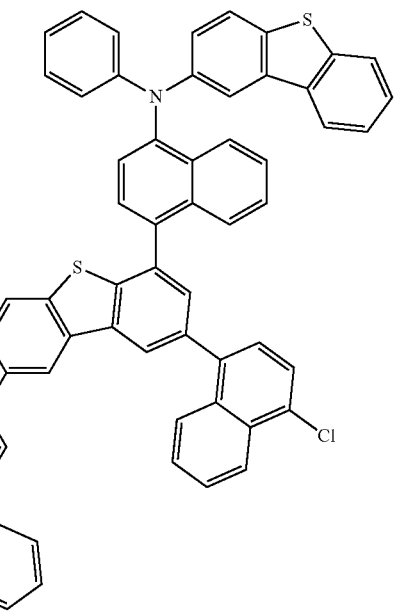
Sub 1-11
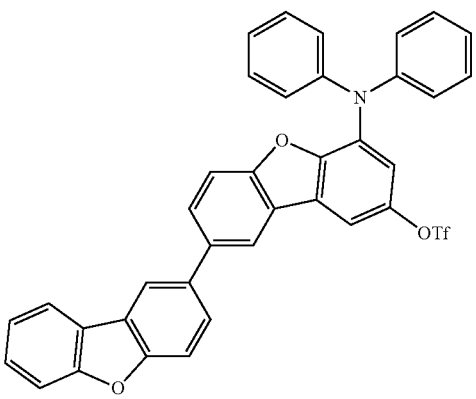
Sub 1-12
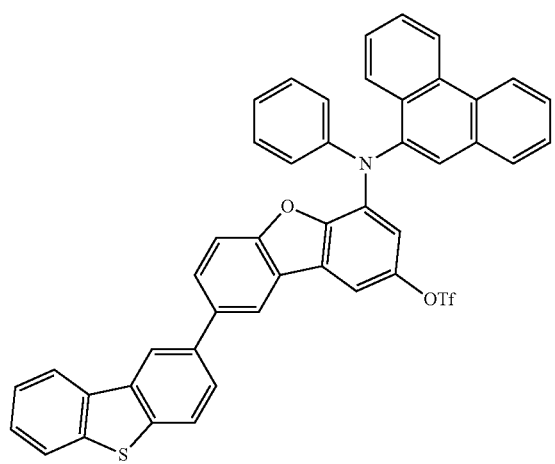

Sub 1-13
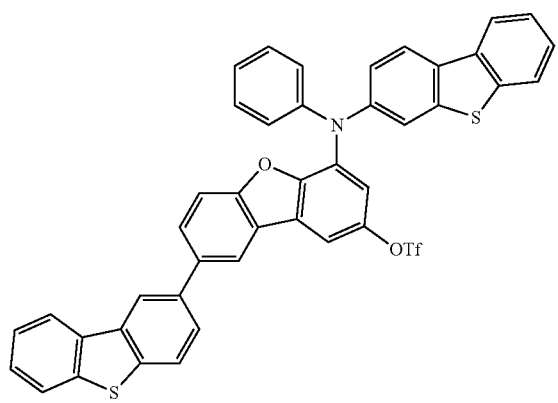
Sub 1-14
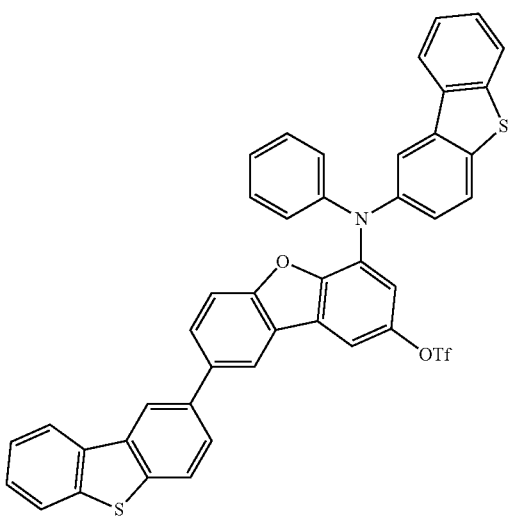
Sub 1-15
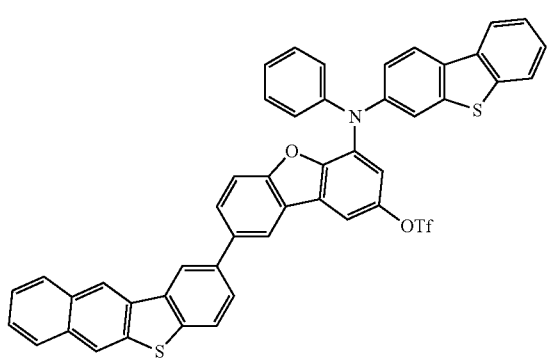
Sub 1-16
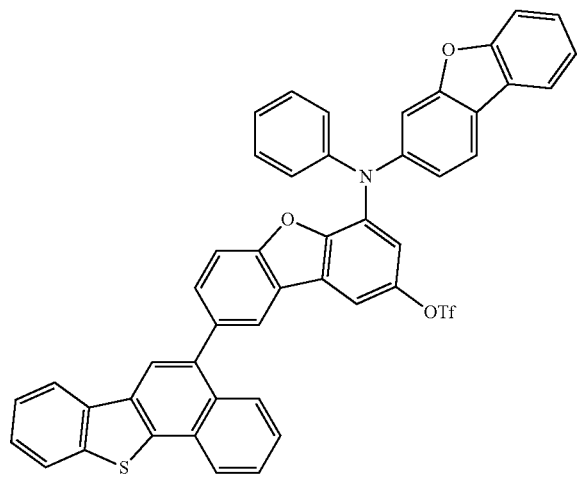
Sub 1-17
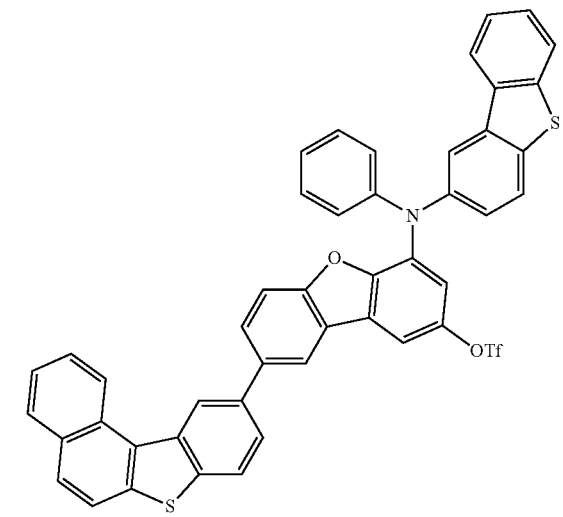
Sub 1-18
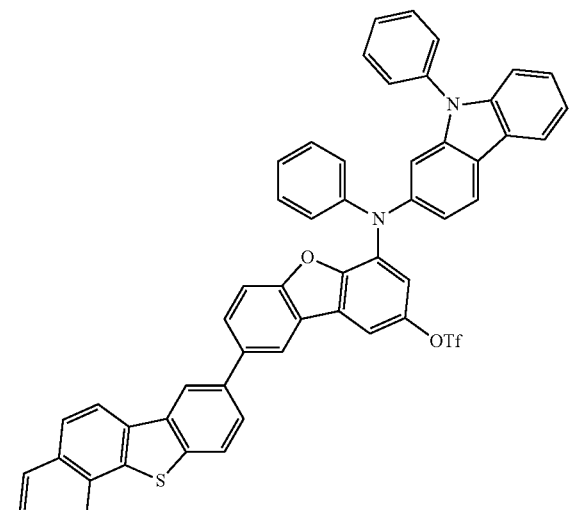

Sub 1-19
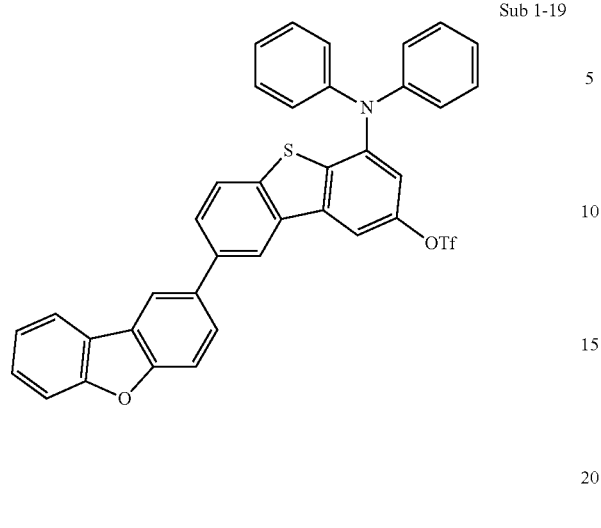
Sub 1-22
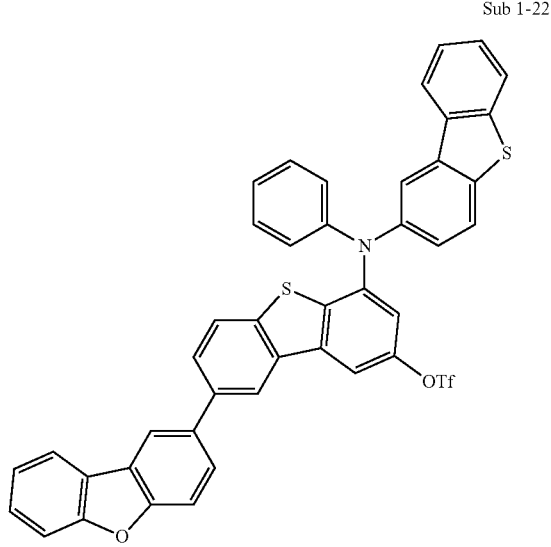
Sub 1-20
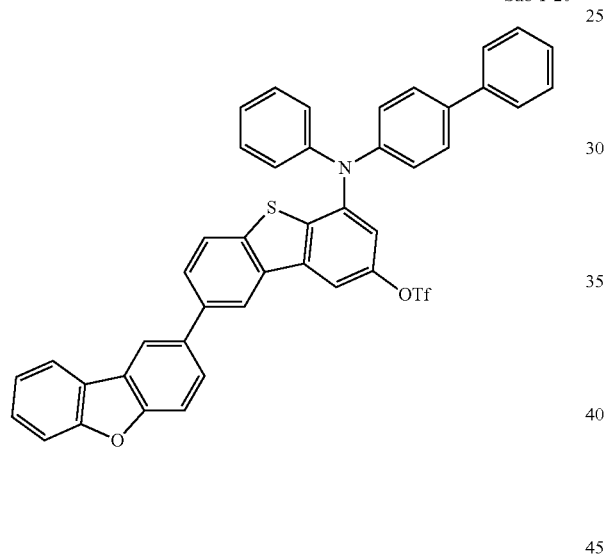
Sub 1-23
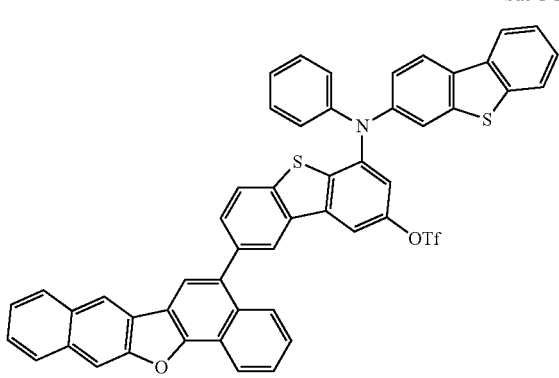
Sub 1-21
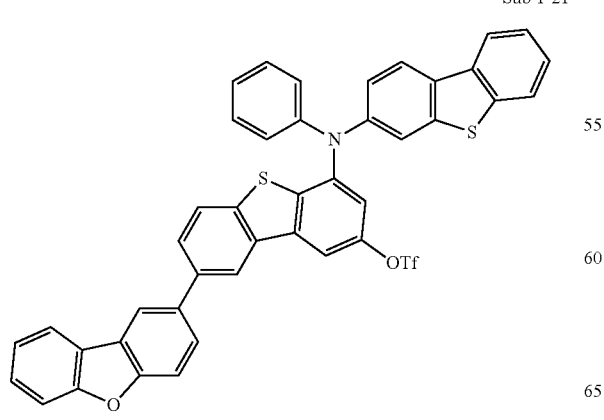
Sub 1-24
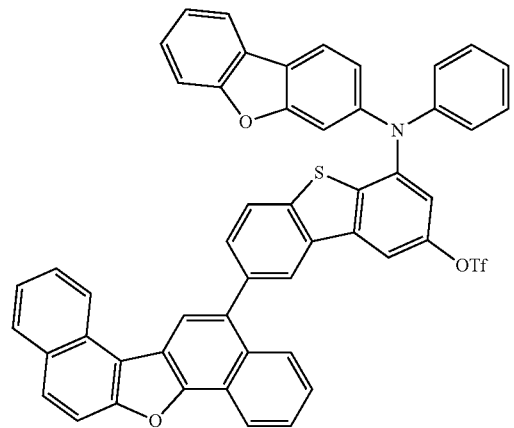

Sub 1-25
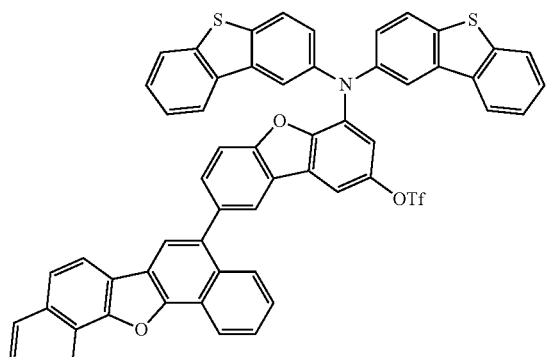
Sub 1-26
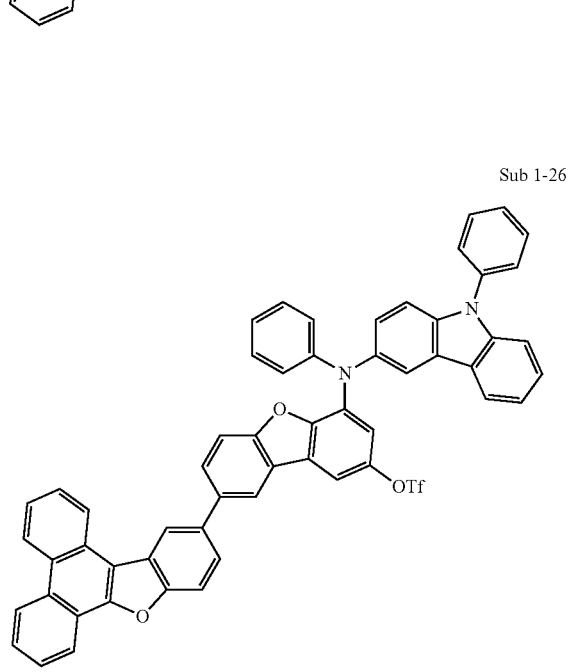
Sub 1-27
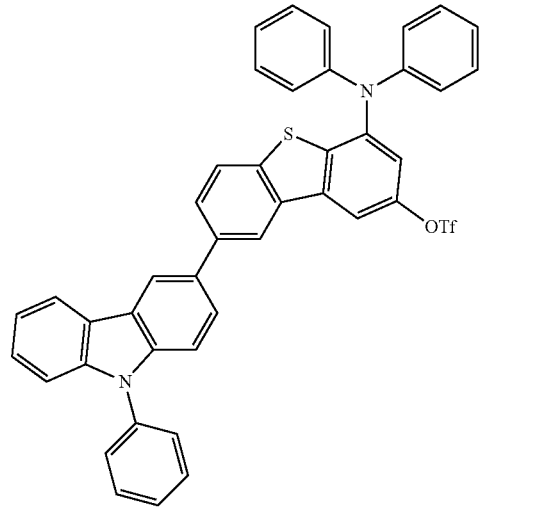
Sub 1-28
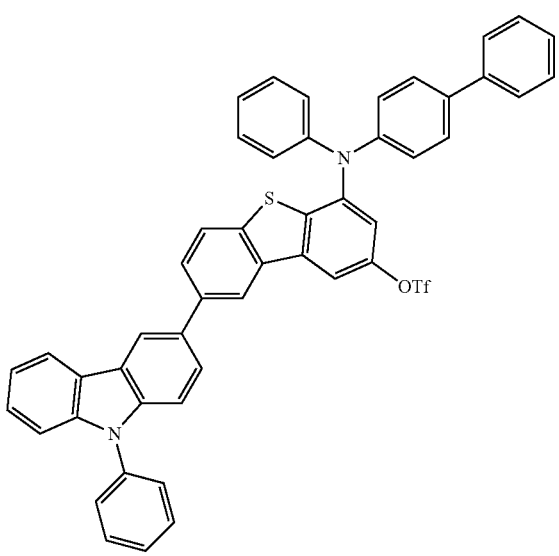
Sub 1-29
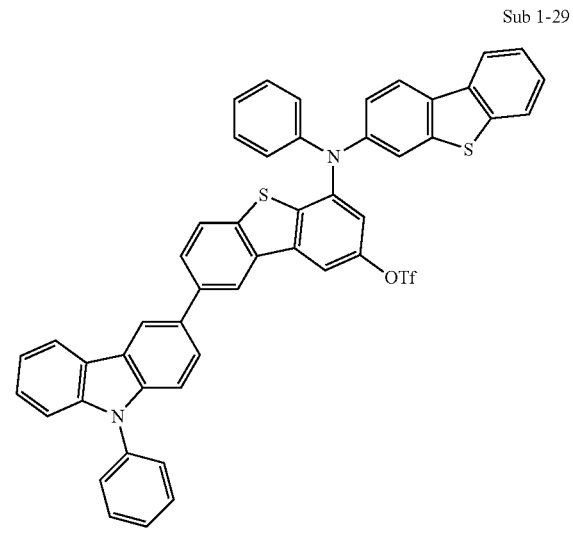

Sub 1-30
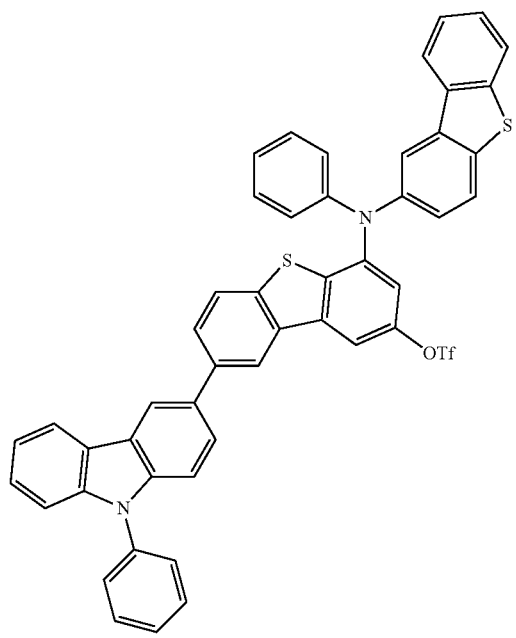
Sub 1-32
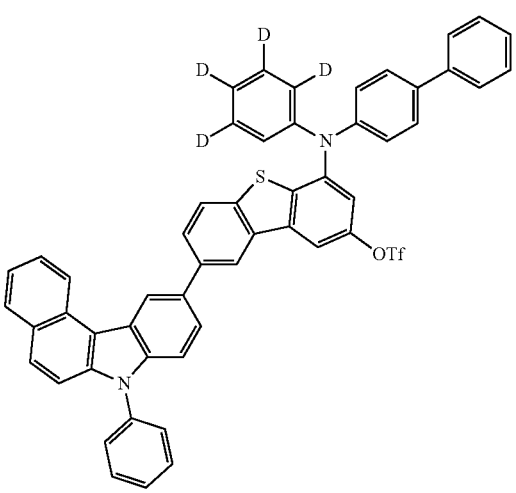
Sub 1-33
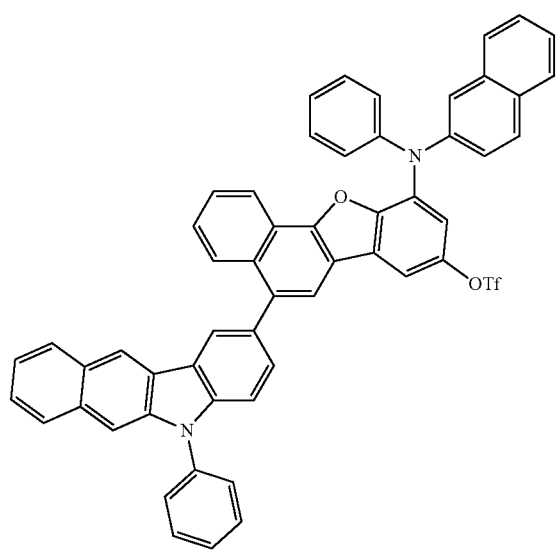
Sub 1-31
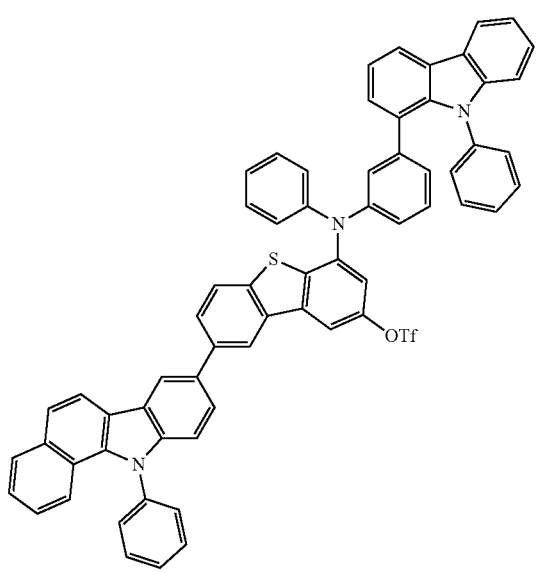
Sub 1-34
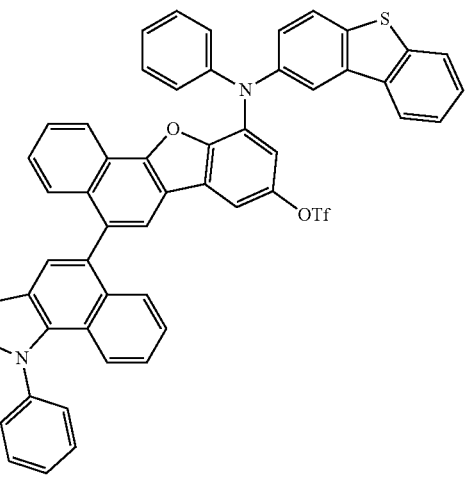

-continued
Sub 1-35
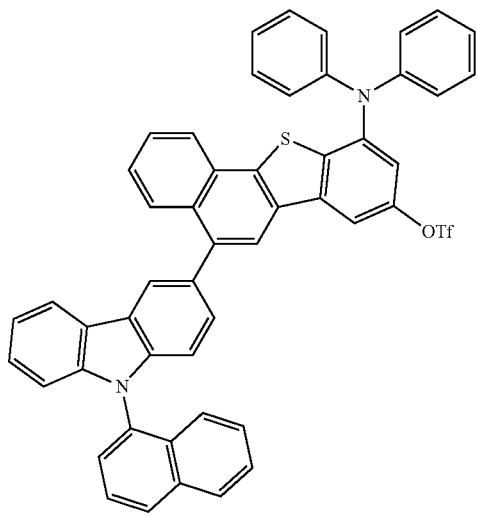
Sub 1-36
Sub 1-37
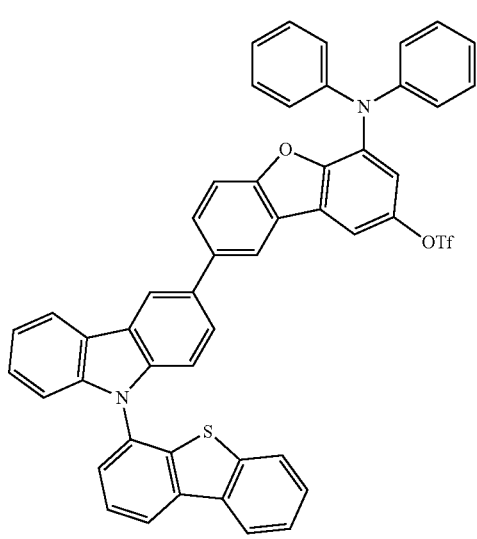
Sub 1-38
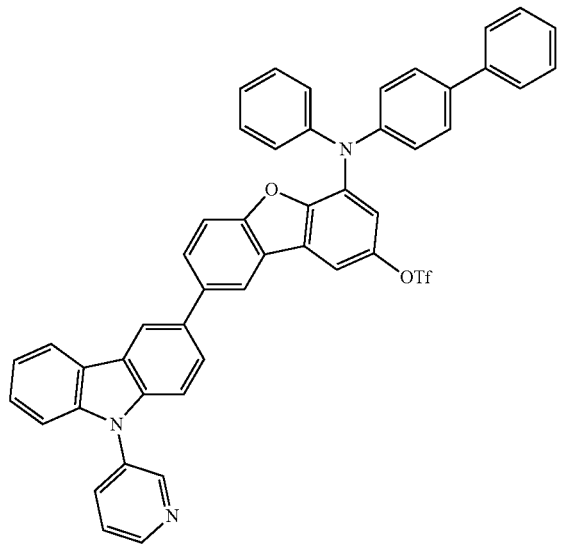
Sub 1-39
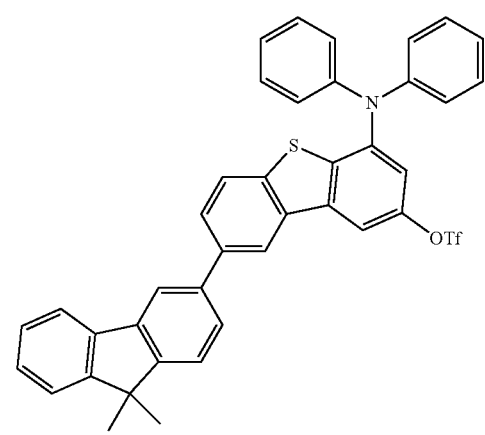
Sub 1-40

Sub 1-41
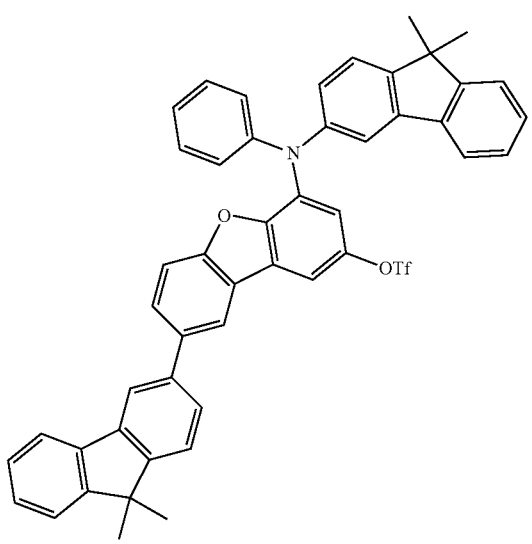
Sub 1-43
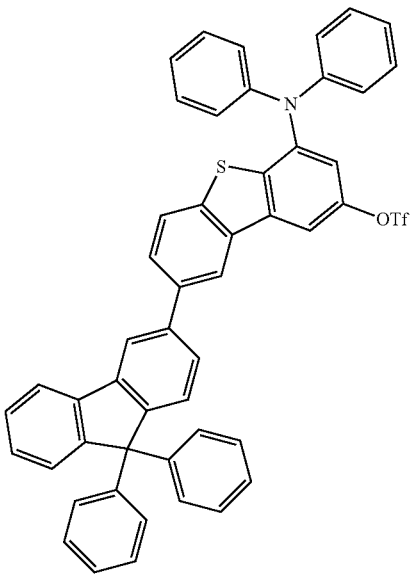
Sub 1-42
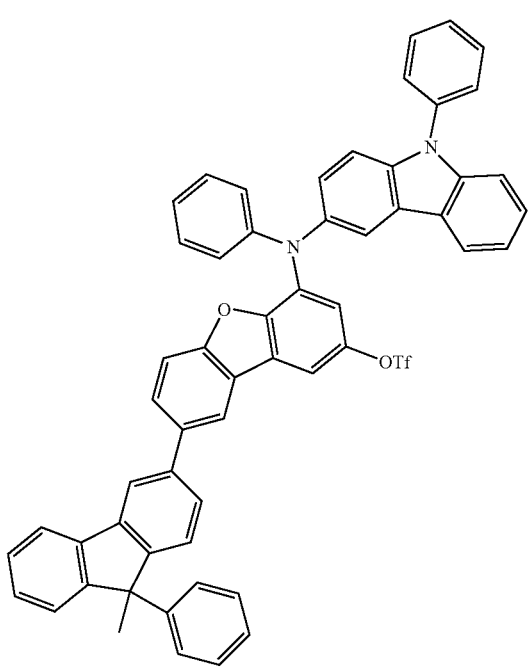
Sub 1-44
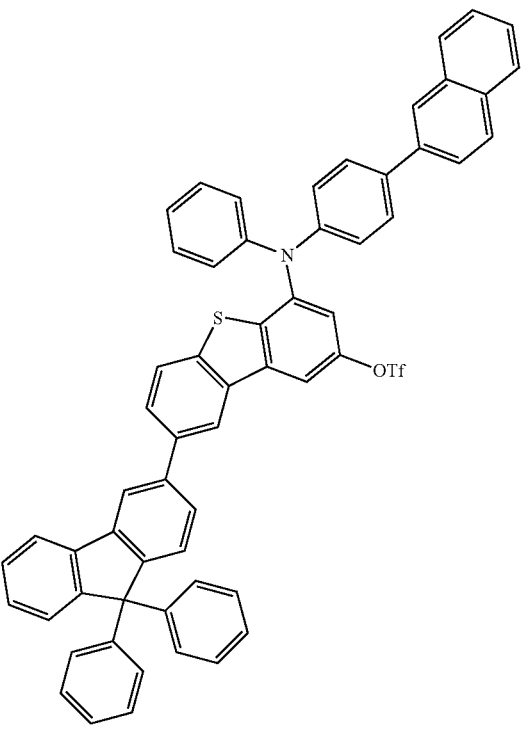

Sub 1-45
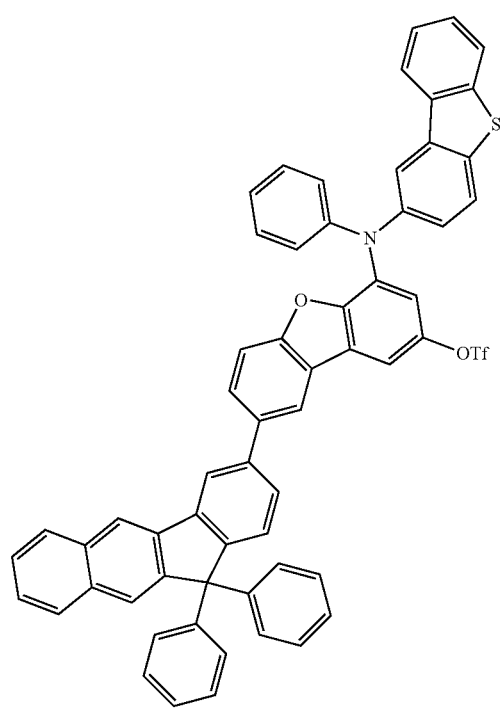
Sub 1-47
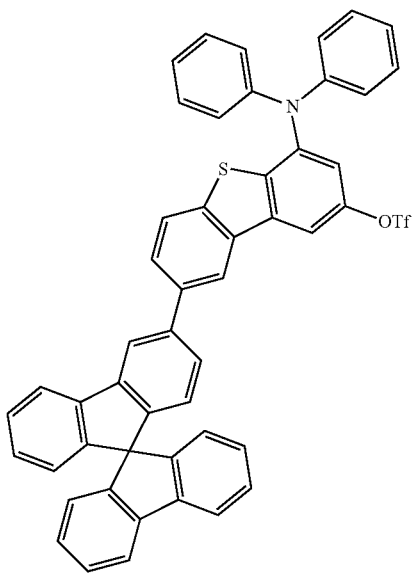
Sub 1-46
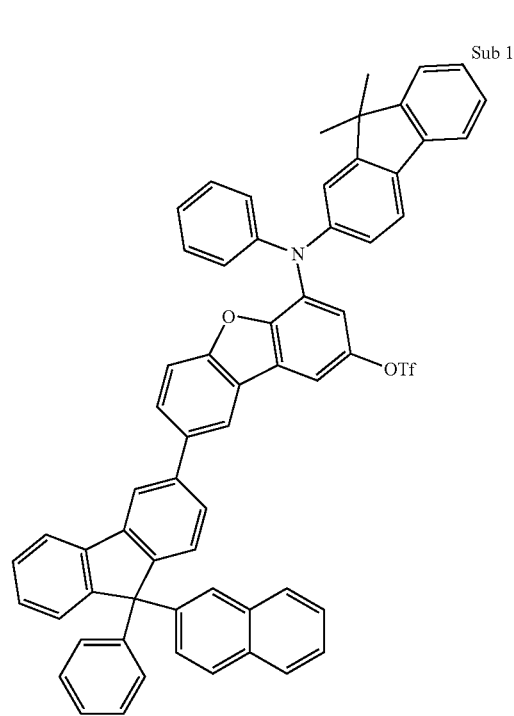
Sub 1-48
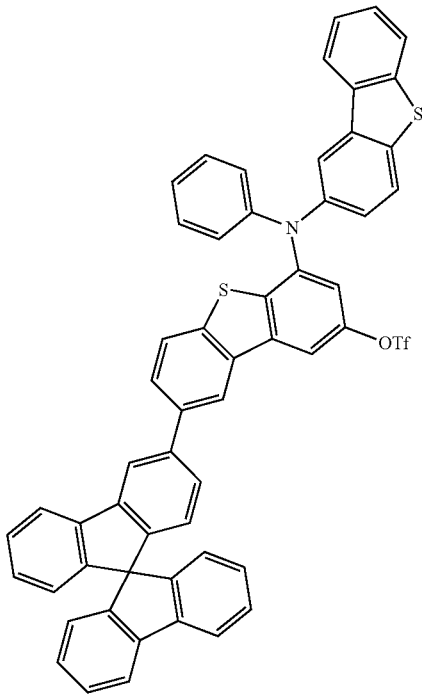

Sub 1-49
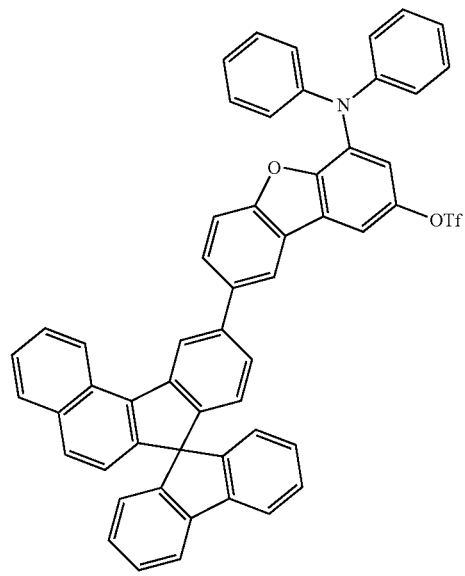
Sub 1-51
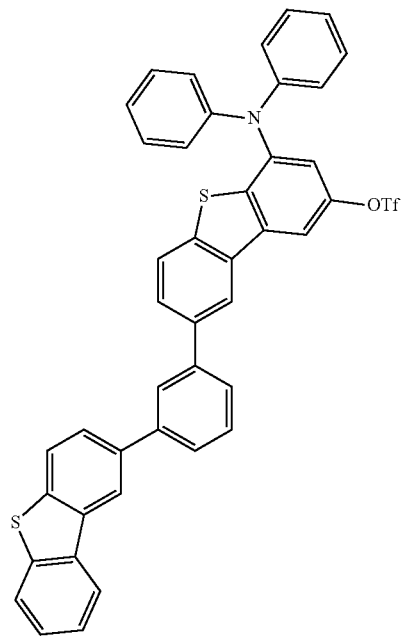
Sub 1-50
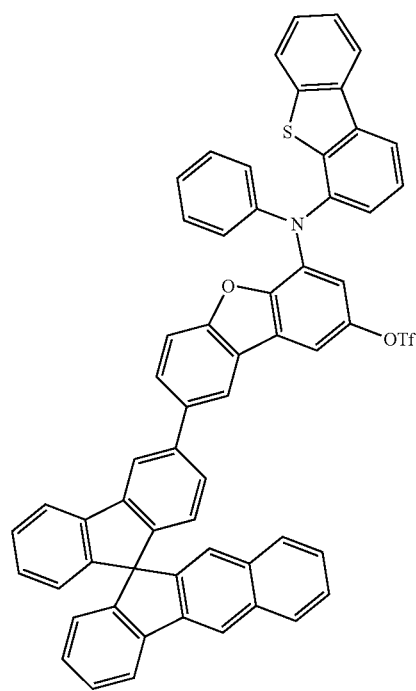
Sub 1-52
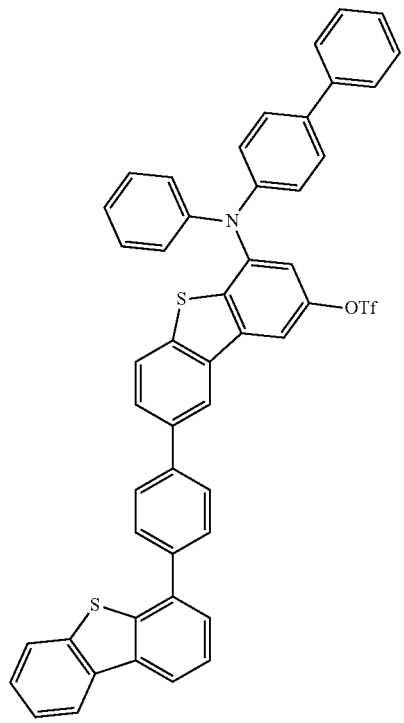

Sub 1-53
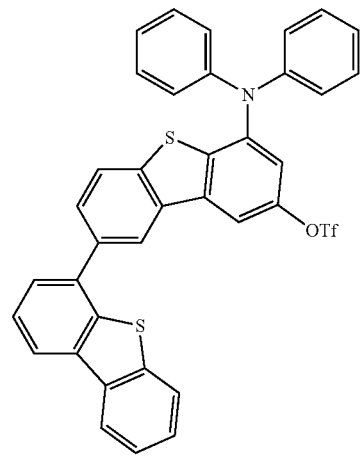
Sub 1-54
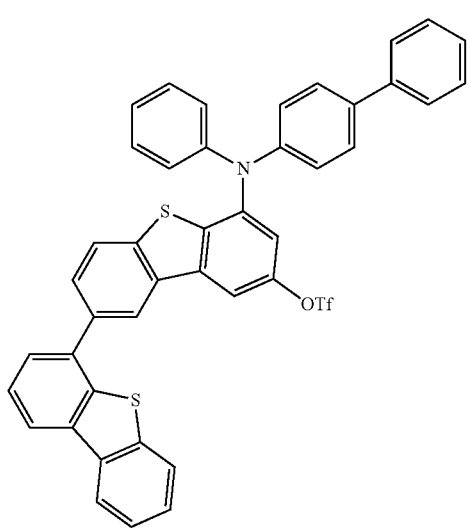
Sub 1-55
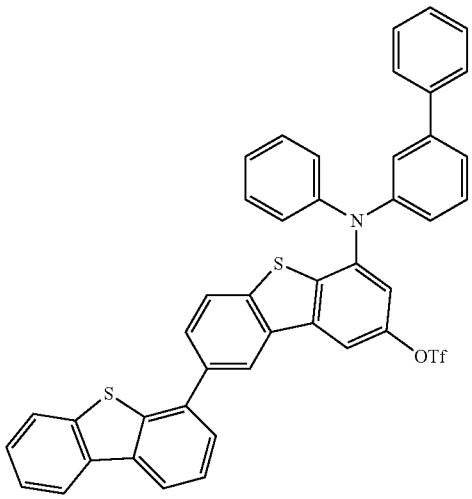
Sub 1-56
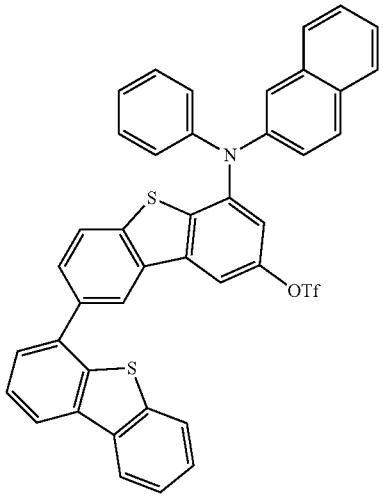
Sub 1-57
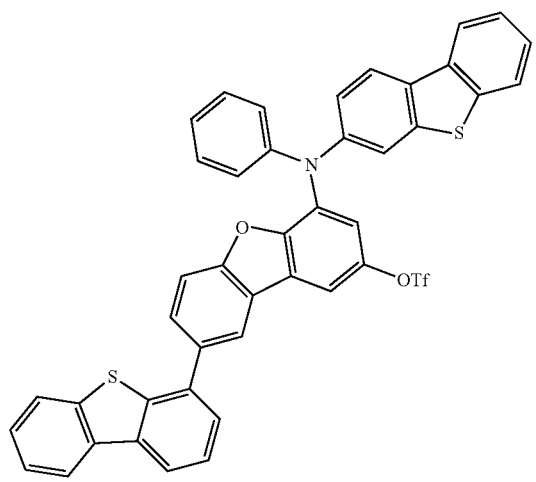
Sub 1-58
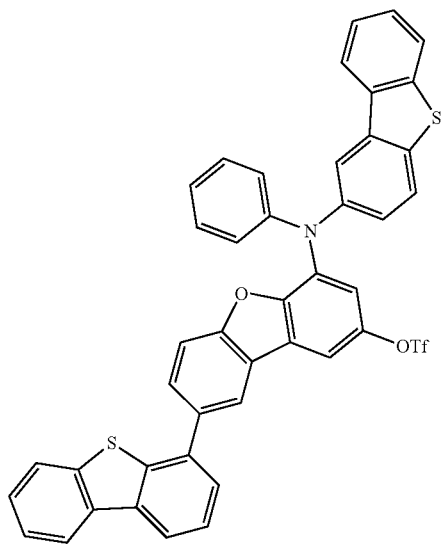

Sub 1-59
Sub 1-60
Sub 1-61
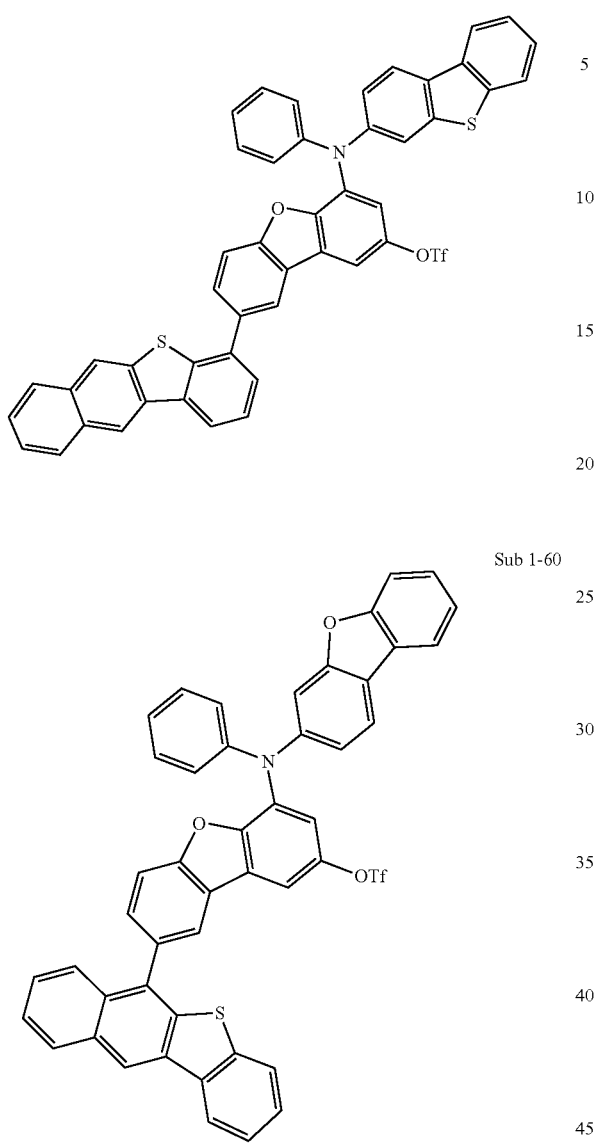
Sub 1-62
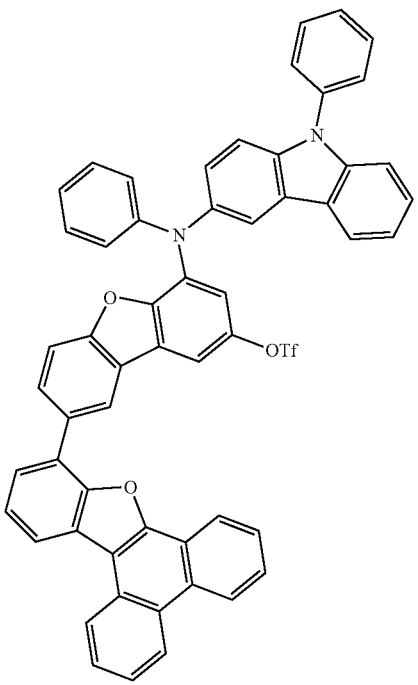
Sub 1-63
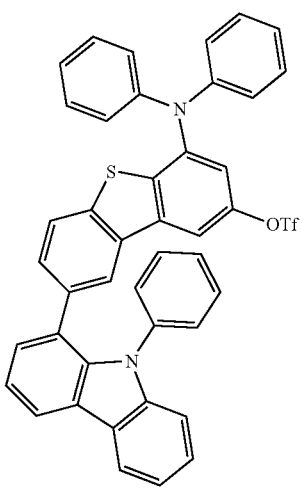

-continued
Sub 1-64
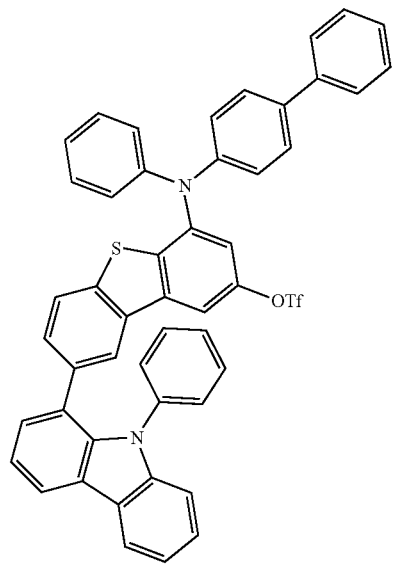
Sub 1-65
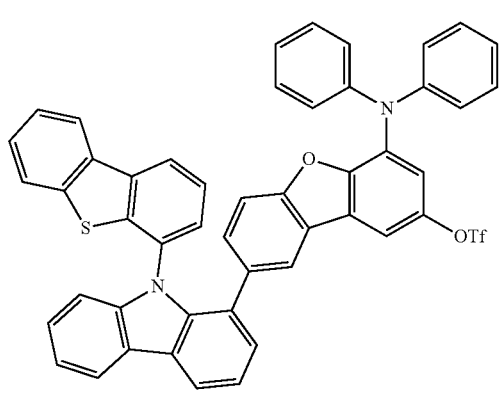
Sub 1-66
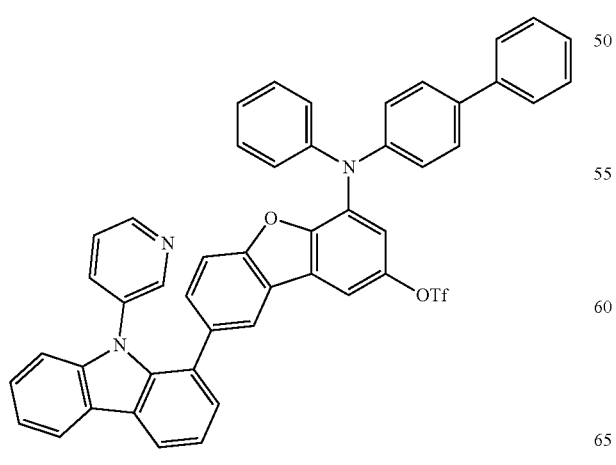
-continued
Sub 1-67
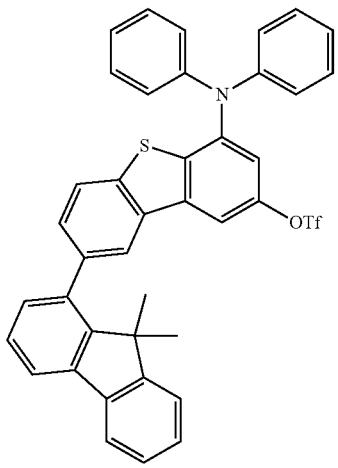
Sub 1-68
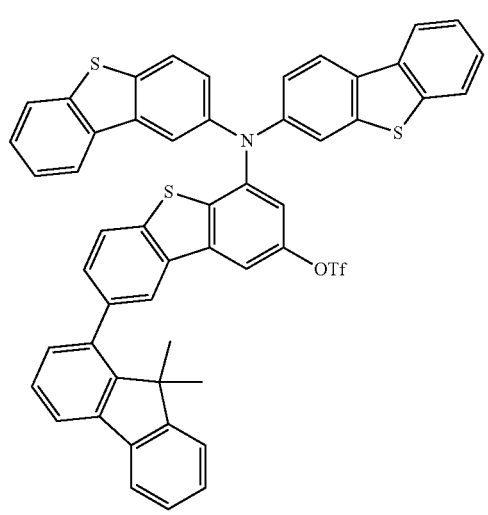
Sub 1-69
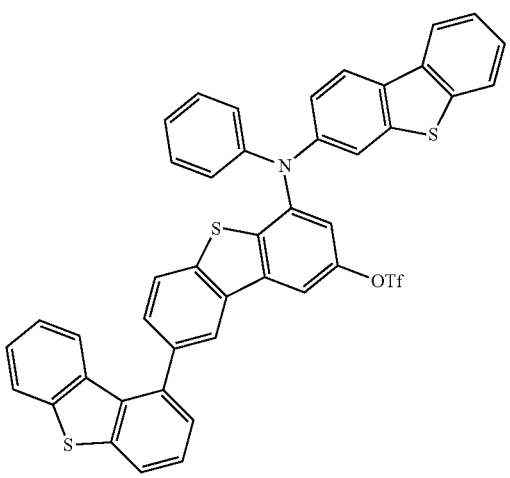

Sub 1-70
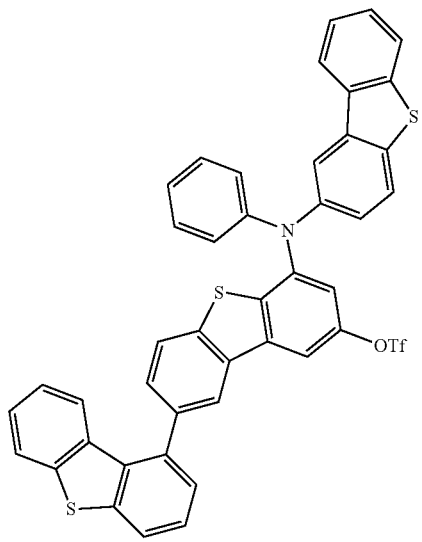
Sub 1-71
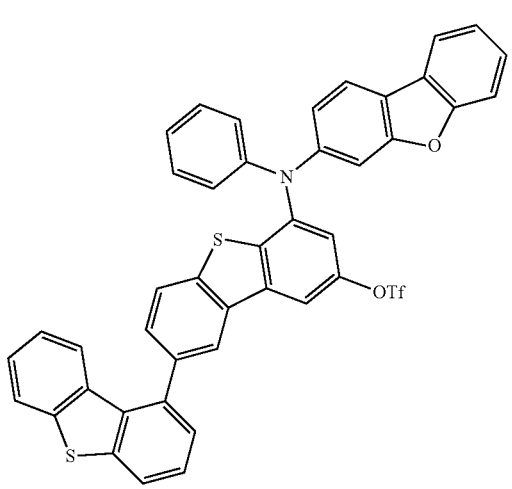
Sub 1-72
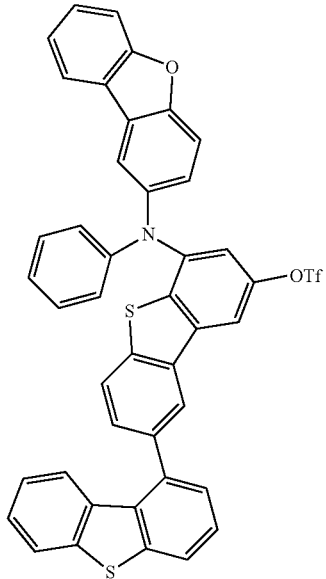
Sub 1-73
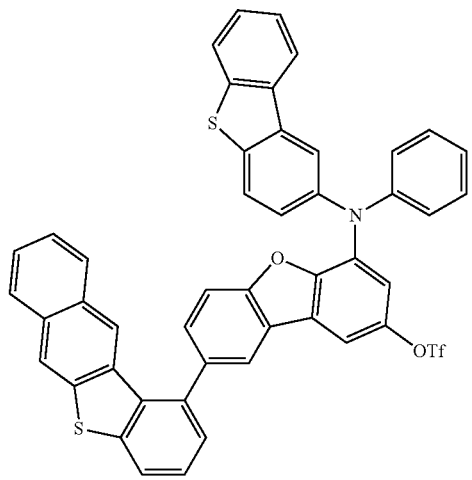
Sub 1-74
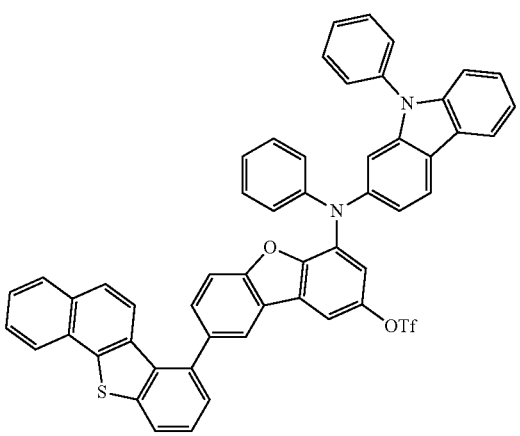
Sub 1-75
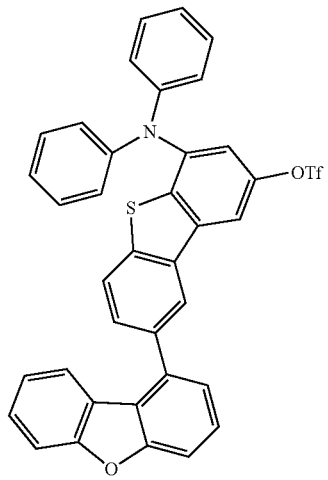

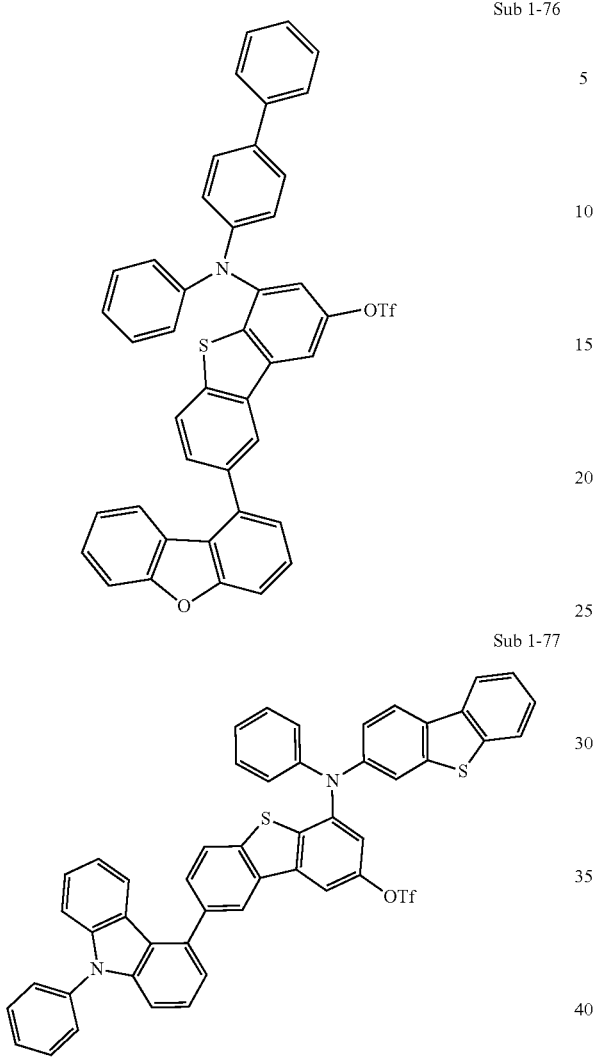

Sub 1-81

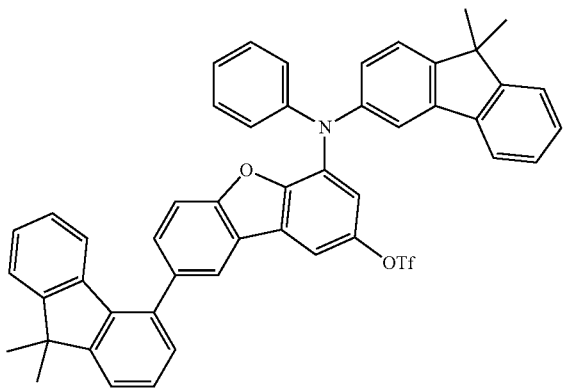

Sub 1-83

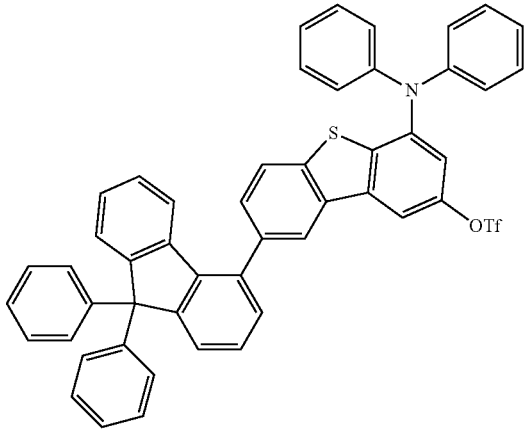

Sub 1-82

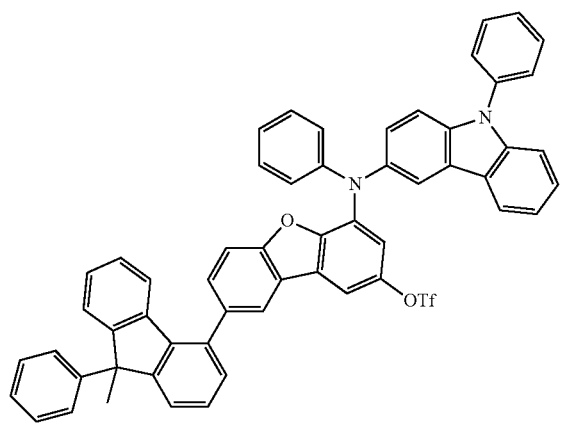

Sub 1-84

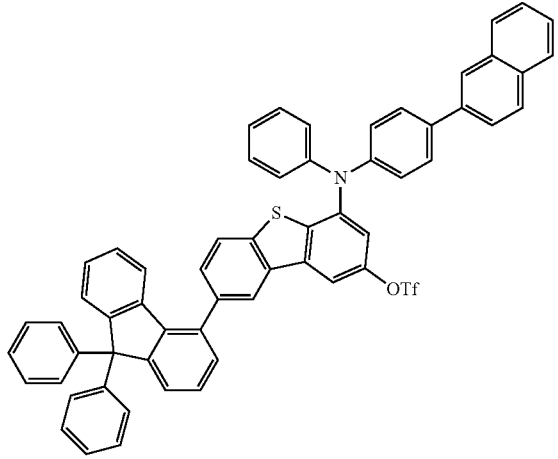

TABLE 1

| Compound | FD-MS | Compound | FD-MS |
| --- | --- | --- | --- |
| Sub 1-1 | m/z = 681.07 ($C_{37}H_{22}F_3NO_3S_3$ = 681.76) | Sub 1-2 | m/z = 757.10 ($C_{43}H_{26}F_3NO_3S_3$ = 757.86) |
| Sub 1-3 | m/z = 757.10 ($C_{43}H_{26}F_3NO_3S_3$ = 757.86) | Sub 1-4 | m/z = 731.09 ($C_{41}H_{24}F_3NO_3S_3$ = 731.82) |
| Sub 1-5 | m/z = 787.06 ($C_{43}H_{24}F_3NO_3S_4$ = 787.90) | Sub 1-6 | m/z = 787.06 ($C_{43}H_{24}F_3NO_3S_4$ = 787.90) |
| Sub 1-7 | m/z = 771.08 ($C_{43}H_{24}F_3NO_4S_3$ = 771.84) | Sub 1-8 | m/z = 771.08 ($C_{43}H_{24}F_3NO_4S_3$ = 771.84) |
| Sub 1-9 | m/z = 749.11 ($C_{48}H_{28}ClNS_3$ = 750.39) | Sub 1-10 | m/z = 925.17 ($C_{62}H_{36}ClNS_3$ = 926.61) |
| Sub 1-11 | m/z = 649.12 ($C_{37}H_{22}F_3NO_5S$ = 649.64) | Sub 1-12 | m/z = 765.13 ($C_{45}H_{26}F_3NO_4S_2$ = 765.82) |
| Sub 1-13 | m/z = 771.08 ($C_{43}H_{24}F_3NO_4S_3$ = 771.84) | Sub 1-14 | m/z = 771.08 ($C_{43}H_{24}F_3NO_4S_3$ = 771.84) |
| Sub 1-15 | m/z = 821.10 ($C_{47}H_{26}F_3NO_4S_3$ = 821.90) | Sub 1-16 | m/z = 805.12 ($C_{47}H_{26}F_3NO_5S_2$ = 805.84) |
| Sub 1-17 | m/z = 821.10 ($C_{47}H_{26}F_3NO_4S_3$ = 821.90) | Sub 1-18 | m/z = 880.17 ($C_{53}H_{31}F_3N_2O_{432}$ = 880.96) |
| Sub 1-19 | m/z = 665.09 ($C_{37}H_{22}F_3NO_4S_2$ = 665.70) | Sub 1-20 | m/z = 741.13 ($C_{43}H_{26}F_3NO_4S_2$ = 741.80) |
| Sub 1-21 | m/z = 771.08 ($C_{43}H_{24}F_3NO_4S_3$ = 771.84) | Sub 1-22 | m/z = 771.08 ($C_{43}H_{24}F_3NO_4S_3$ = 771.84) |
| Sub 1-23 | m/z = 871.11 ($C_{51}H_{28}F_3NO_4S_3$ = 871.96) | Sub 1-24 | m/z = 855.14 ($C_{51}H_{28}F_3NO_5S_2$ = 855.90) |
| Sub 1-25 | m/z = 961.12 ($C_{57}H_{30}F_3NO_5S_3$ = 962.04) | Sub 1-26 | m/z = 914.21 ($C_{57}H_{33}F_3N_2O_5S$ = 914.96) |
| Sub 1-27 | m/z = 740.14 ($C_{43}H_{27}F_3N_2O_3S_2$ = 740.82) | Sub 1-28 | m/z = 816.17 ($C_{49}H_{31}F_3N_2O_3S_2$ = 816.91) |
| Sub 1-29 | m/z = 846.13 ($C_{49}H_{29}F_3N_2O_3S_3$ = 846.96) | Sub 1-30 | m/z = 846.13 ($C_{49}H_{29}F_3N_2O_3S_3$ = 846.96) |
| Sub 1-31 | m/z = 1031.25 ($C_{65}H_{40}F_3N_3O_3S_2$ = 1032.17) | Sub 1-32 | m/z = 870.21 ($C_{53}H_{29}D_4F_3N_2O_3S_2$ = 871.00) |
| Sub 1-33 | m/z = 874.21 ($C_{55}H_{33}F_3N_2O_4S$ = 874.93) | Sub 1-34 | m/z = 930.18 ($C_{57}H_{33}F_3N_2O_4S_2$ = 931.02) |
| Sub 1-35 | m/z = 790.16 ($C_{47}H_{29}F_3N_2O_3S_2$ = 790.88) | Sub 1-36 | m/z = 916.20 ($C_{57}H_{35}F_3N_2O_3S_2$ = 917.03) |
| Sub 1-37 | m/z = 830.15 ($C_{49}H_{29}F_3N_2O_4S_2$ = 830.90) | Sub 1-38 | m/z = 801.19 ($C_{48}H_{30}F_3N_3O_4S$ = 801.84) |
| Sub 1-39 | m/z = 691.15 ($C_{40}H_{28}F_3NO_3S_2$ = 691.78) | Sub 1-40 | m/z = 903.12 ($C_{52}H_{32}F_3NO_3S_4$ = 904.07) |
| Sub 1-41 | m/z = 791.23 ($C_{49}H_{36}F_3NO_4S$ = 791.89) | Sub 1-42 | m/z = 902.24 ($C_{57}H_{37}F_3N_2O_4S$ = 902.99) |
| Sub 1-43 | m/z = 815.18 ($C_{50}H_{32}F_3NO_3S_2$ = 815.93) | Sub 1-44 | m/z = 941.22 ($C_{60}H_{38}F_3NO_3S_2$ = 942.08) |
| Sub 1-45 | m/z = 955.20 ($C_{60}H_{36}F_3NO_4S_2$ = 956.07) | Sub 1-46 | m/z = 965.28 ($C_{63}H_{42}F_3NO_4S$ = 966.09) |
| Sub 1-47 | m/z = 813.16 ($C_{50}H_{30}F_3NO_3S_2$ = 813.91) | Sub 1-48 | m/z = 919.15 ($C_{56}H_{32}F_3NO_3S_3$ = 920.05) |
| Sub 1-49 | m/z = 847.20 ($C_{54}H_{32}F_3NO_4S$ = 847.91) | Sub 1-50 | m/z = 953.19 ($C_{60}H_{34}F_3NO_4S_2$ = 954.05) |
| Sub 1-51 | m/z = 757.10 ($C_{43}H_{26}F_3NO_3S_3$ = 757.86) | Sub 1-52 | m/z = 833.13 ($C_{49}H_{30}F_3NO_3S_3$ = 833.96) |
| Sub 1-53 | m/z = 681.07 ($C_{37}H_{22}F_3NO_3S_3$ = 681.76) | Sub 1-54 | m/z = 757.10 ($C_{43}H_{26}F_3NO_3S_3$ = 757.86) |
| Sub 1-55 | m/z = 757.10 ($C_{43}H_{26}F_3NO_3S_3$ = 757.86) | Sub 1-56 | m/z = 731.09 ($C_{41}H_{24}F_3NO_3S_3$ = 731.82) |

TABLE 1-continued

| Compound | FD-MS | Compound | FD-MS |
|---|---|---|---|
| Sub 1-57 | m/z = 771.08 ($C_{43}H_{24}F_3NO_4S_3$ = 771.84) | Sub 1-58 | m/z = 771.08 ($C_{43}H_{24}F_3NO_4S_3$ = 771.84) |
| Sub 1-59 | m/z = 821.10 ($C_{47}H_{26}F_3NO_4S_3$ = 821.90) | Sub 1-60 | m/z = 805.12 ($C_{47}H_{26}F_3NO_5S_2$ = 805.84) |
| Sub 1-61 | m/z = 961.12 ($C_{57}H_{30}F_3NO_5S_3$ = 962.04) | Sub 1-62 | m/z = 914.21 ($C_{57}H_{33}F_3N_2O_5S$ = 914.96) |
| Sub 1-63 | m/z = 740.14 ($C_{43}H_{27}F_3N_2O_3S_2$ = 740.82) | Sub 1-64 | m/z = 816.17 ($C_{49}H_{31}F_3N_2O_3S_2$ = 816.91) |
| Sub 1-65 | m/z = 830.15 ($C_{49}H_{29}F_3N_2O_4S_2$ = 830.90) | Sub 1-66 | m/z = 801.19 ($C_{48}H_{30}F_3N_3O_4S$ = 801.84) |
| Sub 1-67 | m/z = 691.15 ($C_{40}H_{28}F_3NO_3S_2$ = 691.78) | Sub 1-68 | m/z = 903.12 ($C_{52}H_{32}F_3NO_3S_4$ = 904.07) |
| Sub 1-69 | m/z = 787.06 ($C_{43}H_{24}F_3NO_3S_4$ = 787.90) | Sub 1-70 | m/z = 787.06 ($C_{43}H_{24}F_3NO_3S_4$ = 787.90) |
| Sub 1-71 | m/z = 771.08 ($C_{43}H_{24}F_3NO_4S_3$ = 771.84) | Sub 1-72 | m/z = 771.08 ($C_{43}H_{24}F_3NO_4S_3$ = 771.84) |
| Sub 1-73 | m/z = 821.10 ($C_{47}H_{26}F_3NO_4S_3$ = 821.90) | Sub 1-74 | m/z = 880.17 ($C_{53}H_{31}F_3N_2O_{432}$ = 880.96) |
| Sub 1-75 | m/z = 665.09 ($C_{37}H_{22}F_3NO_4S_2$ = 665.70) | Sub 1-76 | m/z = 741.13 ($C_{43}H_{26}F_3NO_4S_2$ = 741.80) |
| Sub 1-77 | m/z = 846.13 ($C_{49}H_{29}F_3N_2O_3S_3$ = 846.96) | Sub 1-78 | m/z = 846.13 ($C_{49}H_{29}F_3N_2O_3S_3$ = 846.96) |
| Sub 1-79 | m/z = 1031.25 ($C_{65}H_{40}F_3N_3O_3S_2$ = 1032.17) | Sub 1-80 | m/z = 870.21 ($C_{53}H_{29}D_4F_3N_2O_3S_2$ = 871.00) |
| Sub 1-81 | m/z = 791.23 ($C_{49}H_{36}F_3NO_4S$ = 791.89) | Sub 1-82 | m/z = 902.24 ($C_{57}H_{37}F_3N_2O_4S$ = 902.99) |
| Sub 1-83 | m/z = 815.18 ($C_{50}H_{32}F_3NO_3S_2$ = 815.93) | Sub 1-84 | m/z = 941.22 ($C_{60}H_{38}F_3NO_3S_2$ = 942.08) |

II. Synthesis of Sub 2

Sub 2 of Reaction Scheme 1 above may be synthesized by a reaction pathway of Reaction Scheme 3, but is not limited thereto.

<Reaction Scheme 3>

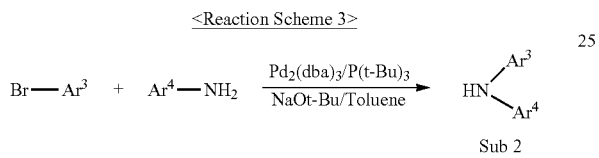

Synthetic Example of Sub 2-1

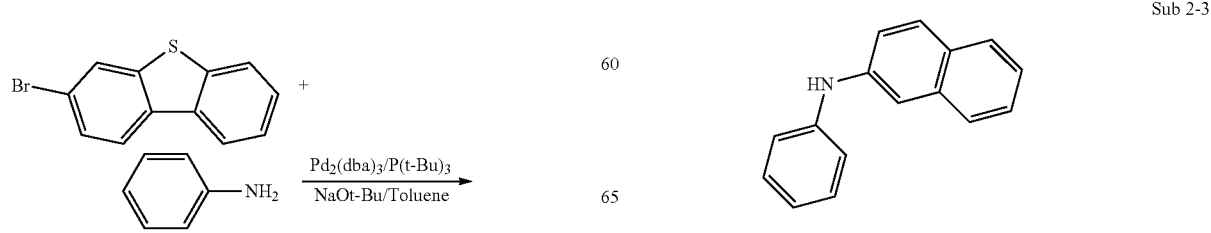

Bromobenzene (47.6 g, 170.14 mmol) and aniline (23.7 g, 255.21 mmol) were subjected to the synthesis method of Sub 1-II to give a product (42.0 g, yield: 73%).

Synthetic Example of Sub 2-14

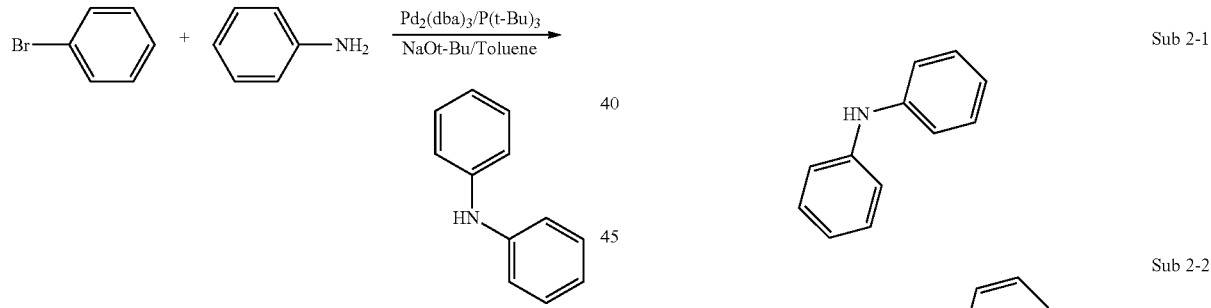

3-Bromodibenzothiophene (42.5 g, 161.50 mmol) and anilne (22.56 g, 242.26 mmol) were subjected to the synthessi method of Sub 1-II to give a product (34.6 g, yield: 78%).

Examples of Sub 2 are as follows, but are not limited thereto.

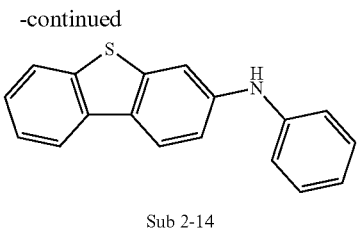

-continued
Sub 2-4
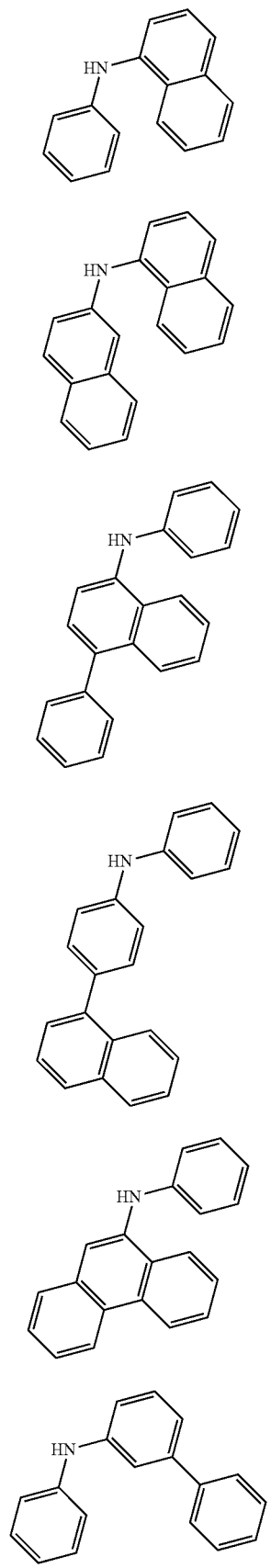
Sub 2-5
Sub 2-6
Sub 2-7
Sub 2-8
Sub 2-9
-continued
Sub 2-10
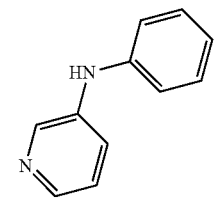
Sub 2-11
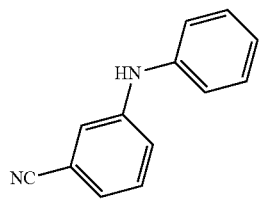
Sub 2-12
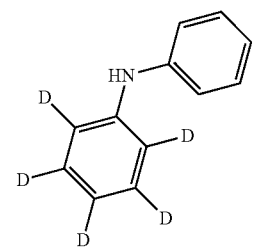
Sub 2-13
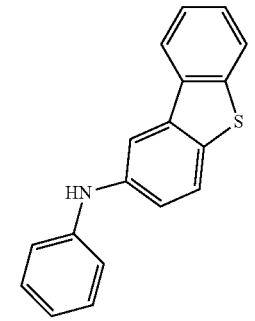
Sub 2-14
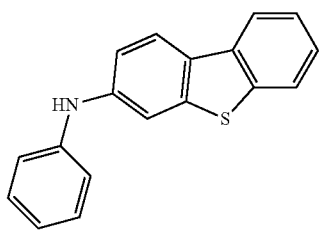
Sub 2-15
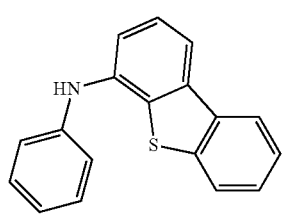

-continued

Sub 2-16

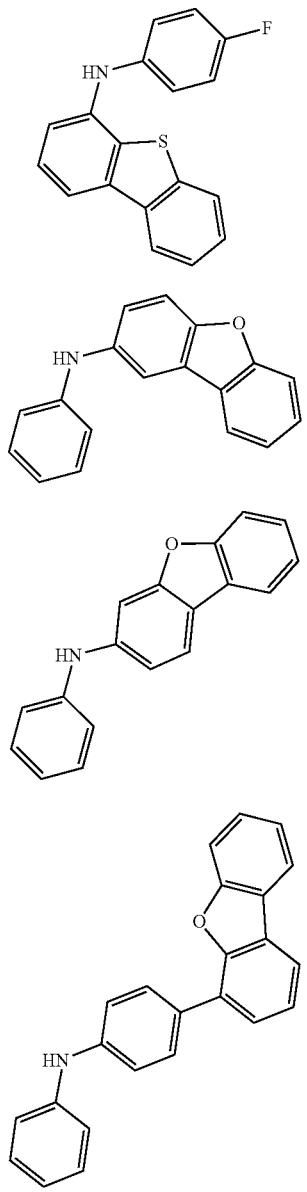

Sub 2-17

Sub 2-18

Sub 2-19

-continued

Sub 2-20

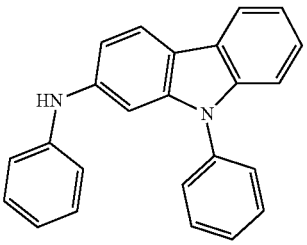

Sub 2-21

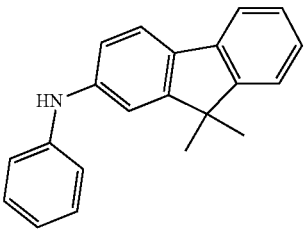

Sub 2-22

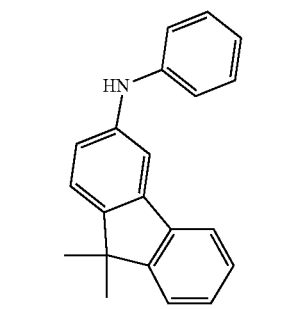

Sub 2-23

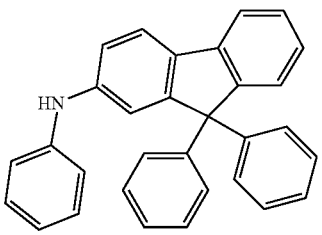

TABLE 2

| Compound | FD-MS | Compound | FD-MS |
| --- | --- | --- | --- |
| Sub 2-1 | m/z = 169.09 ($C_{12}H_{11}N$ = 169.22) | Sub 2-2 | m/z = 245.12 ($C_{18}H_{15}N$ = 245.32) |
| Sub 2-3 | m/z = 219.10 ($C_{16}H_{13}N$ = 219.29) | Sub 2-4 | m/z = 219.10 ($C_{16}H_{13}N$ = 219.29) |
| Sub 2-5 | m/z = 269.12 ($C_{20}H_{15}N$ = 269.35) | Sub 2-6 | m/z = 295.14 ($C_{22}H_{17}N$ = 295.38) |
| Sub 2-7 | m/z = 295.14 ($C_{22}H_{17}N$ = 295.38) | Sub 2-8 | m/z = 269.12 ($C_{20}H_{15}N$ = 269.35) |
| Sub 2-9 | m/z = 245.12 ($C_{18}H_{15}N$ = 245.32) | Sub 2-10 | m/z = 170.08 ($C_{11}H_{10}N_2$ = 170.22) |
| Sub 2-11 | m/z = 194.08 ($C_{13}H_{10}N_2$ = 194.24) | Sub 2-12 | m/z = 174.12($C_{12}H_6D_5N$ = 174.25) |
| Sub 2-13 | m/z = 275.08($C_{18}H_{13}NS$ = 275.37) | Sub 2-14 | m/z = 275.08($C_{18}H_{13}NS$ = 275.37) |
| Sub 2-15 | m/z = 275.08($C_{18}H_{13}NS$ = 275.37) | Sub 2-16 | m/z = 293.07 ($C_{18}H_{12}FNS$ = 293.36) |
| Sub 2-17 | m/z = 259.10 ($C_{18}H_{13}NO$ = 259.31) | Sub 2-18 | m/z = 259.10 ($C_{18}H_{13}NO$ = 259.31) |
| Sub 2-19 | m/z = 335.13($C_{24}H_{17}NO$ = 335.40) | Sub 2-20 | m/z = 334.15($C_{24}H_{18}N_2$ = 334.41) |
| Sub 2-21 | m/z = 285.15 ($C_{21}H_{29}N$ = 285.39) | Sub 2-22 | m/z = 285.15 ($C_{21}H_{29}N$ = 285.39) |
| Sub 2-23 | m/z = 409.18($C_{31}H_{23}N$ = 409.52) | | |

91
Synthetic Example of Final Product
Synthetic Example of P-1
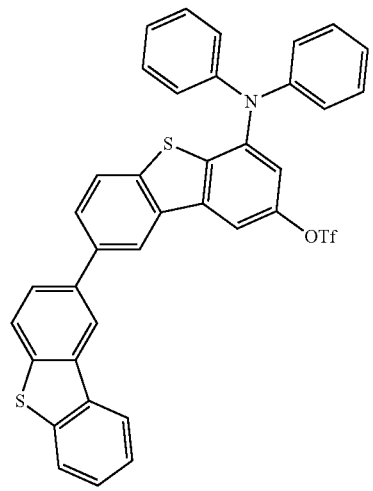
Sub 1-1
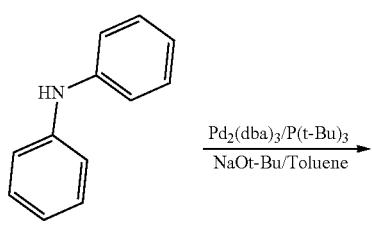
Sub 2-1
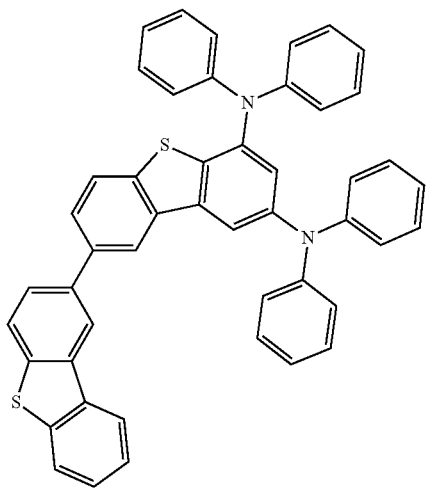
P-1
Sub 1-1 (8.6 g, 12.61 mmol) and Sub 2-1 (2.13 g, 12.61 mmol) were subjected to the synthesis method of Sub 1-1 to give a product (6.8 g, yield: 77%).
92
Synthetic Example of P-9
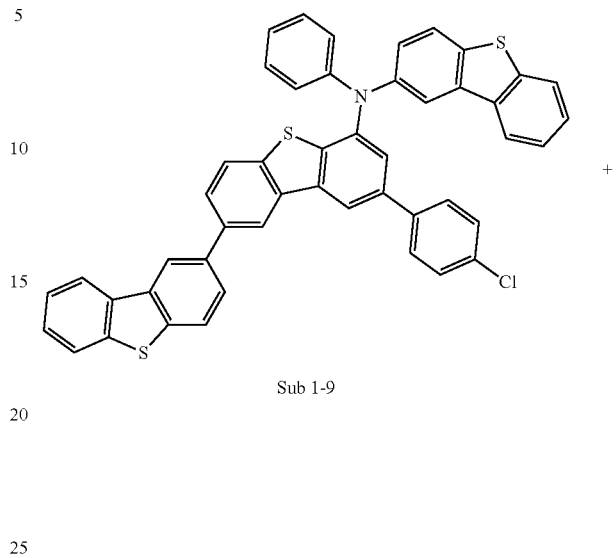
Sub 1-9
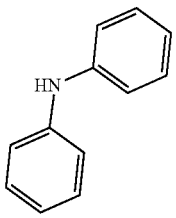
Sub 2-1
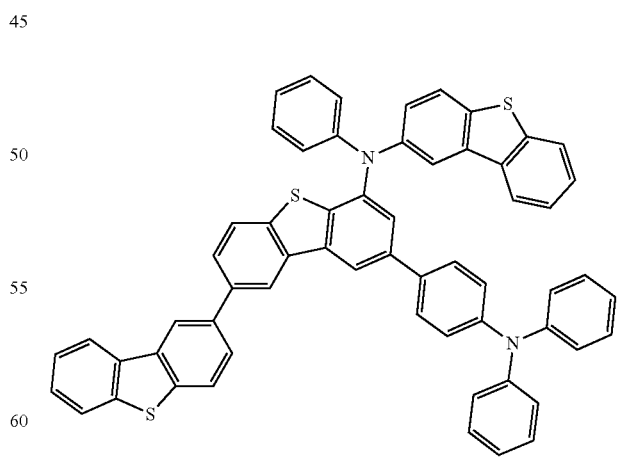
P-9
Sub 1-9 (9.6 g, 12.79 mmol) and Sub 2-1 (2.17 g, 12.79 mmol) were subjected to the synthesis method of Sub 1-1 to give a product (8.8 g, yield: 78%).

Synthetic Example of P-34
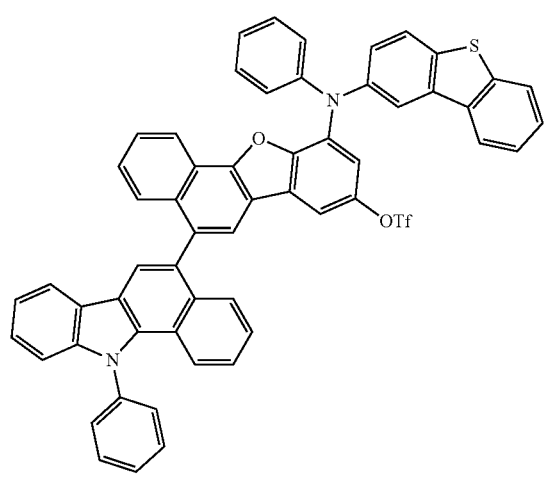
Sub 1-34
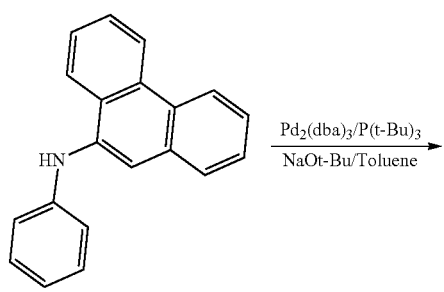
Sub 2-8
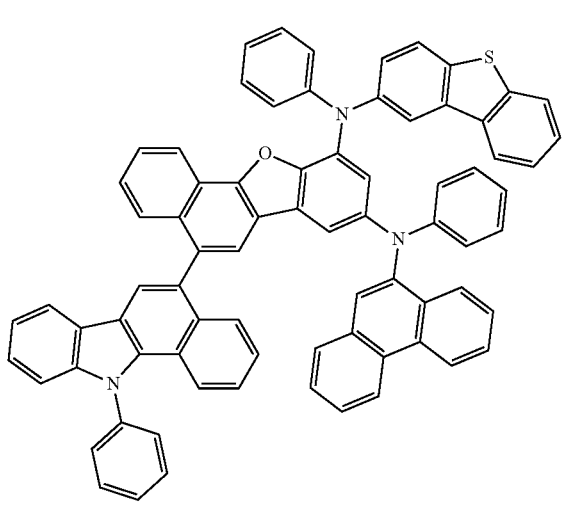
P-34
Sub 1-34 (10.5 g, 11.28 mmol) and Sub 2-8 (3.04 g, 11.28 mmol) were subjected to the synthesis method of Sub 1-1 to give a product (8.9 g, yield: 75%).
Synthetic example of P-84
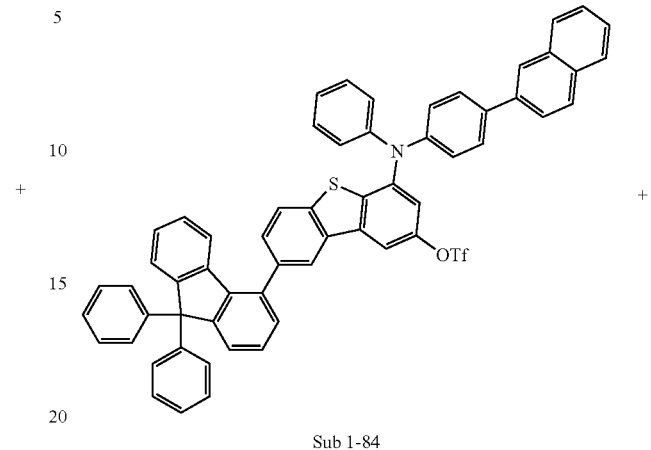
Sub 1-84
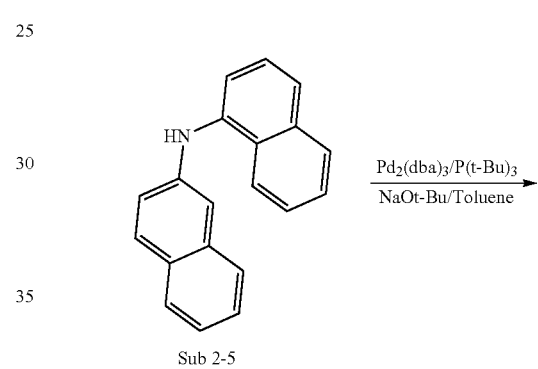
Sub 2-5
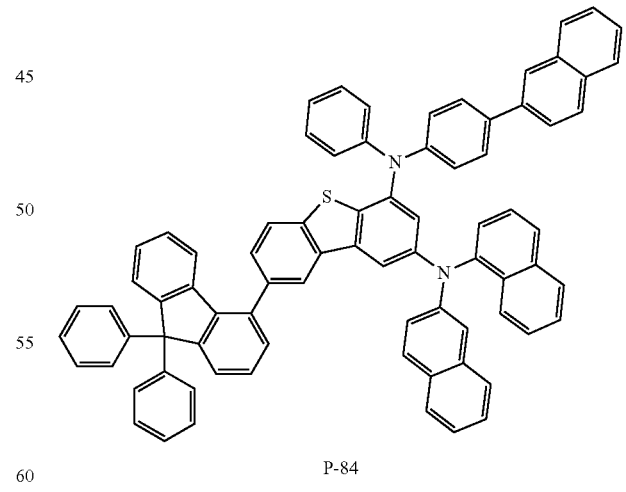
P-84
Sub 1-84 (7.5 g, 7.96 mmol) and Sub 2-5 (2.14 g, 7.96 mmol) were subjected to the synthesis method of Sub 1-1 to give a product (7.5 g, yield: 88%).
FD-MS values of Compounds P-1 to P-84 prepared by the above synthetic examples are shown in Table 3 below.

TABLE 3

| Compound | FD-MS | Compound | FD-MS |
|---|---|---|---|
| P-1 | m/z = 700.20 ($C_{48}H_{32}N_2S_2$ = 700.92) | P-2 | m/z = 852.26 ($C_{60}H_{40}N_2S_2$ = 853.11) |
| P-3 | m/z = 852.26 ($C_{60}H_{40}N_2S_2$ = 853.11) | P-4 | m/z = 800.23 ($C_{56}H_{36}N_2S_2$ = 801.04) |
| P-5 | m/z = 912.18 ($C_{60}H_{36}N_2S_4$ = 913.20) | P-6 | m/z = 912.18 ($C_{60}H_{36}N_2S_4$ = 913.20) |
| P-7 | m/z = 880.22 ($C_{60}H_{36}N_2O_2S_2$ = 881.08) | P-8 | m/z = 880.22 ($C_{60}H_{36}N_2O_2S_2$ = 881.08) |
| P-9 | m/z = 882.22 ($C_{60}H_{38}N_2S_3$ = 883.16) | P-10 | m/z = 1108.30 ($C_{78}H_{48}N_2S_3$ = 1109.44) |
| P-11 | m/z = 668.25 ($C_{48}H_{32}N_2O_2$ = 668.80) | P-12 | m/z = 834.27 ($C_{60}H_{38}N_2OS$ = 835.04) |
| P-13 | m/z = 896.20 ($C_{60}H_{36}N_2OS_3$ = 897.14) | P-14 | m/z = 896.20 ($C_{60}H_{36}N_2OS_3$ = 897.14) |
| P-15 | m/z = 841.22 ($C_{57}H_{35}N_3OS_2$ = 842.05) | P-16 | m/z = 849.24 ($C_{59}H_{35}N_3O_2S$ = 850.01) |
| P-17 | m/z = 946.21 ($C_{64}H_{38}N_2OS_3$ = 947.20) | P-18 | m/z = 1064.35 ($C_{76}H_{48}N_4OS$ = 1065.31) |
| P-19 | m/z = 684.22 ($C_{48}H_{32}N_2OS$ = 684.86) | P-20 | m/z = 836.29 ($C_{60}H_{40}N_2OS$ = 837.05) |
| P-21 | m/z = 896.20 ($C_{60}H_{36}N_2OS_3$ = 897.14) | P-22 | m/z = 896.20 ($C_{60}H_{36}N_2OS_3$ = 897.14) |
| P-23 | m/z = 940.26 ($C_{66}H_{40}N_2OS_2$ = 941.18) | P-24 | m/z = 990.33 ($C_{71}H_{46}N_2O_2S$ = 991.22) |
| P-25 | m/z = 980.25 ($C_{68}H_{40}N_2O_2S_2$ = 981.20) | P-26 | m/z = 1098.39 ($C_{80}H_{50}N_4O_2$ = 1099.31) |
| P-27 | m/z = 759.27 ($C_{54}H_{37}N_3S$ = 759.97) | P-28 | m/z = 961.35 ($C_{70}H_{47}N_3S$ = 962.23) |
| P-29 | m/z = 915.27 ($C_{64}H_{41}N_3S_2$ = 916.17) | P-30 | m/z = 971.25 ($C_{66}H_{41}N_3S_3$ = 972.26) |
| P-31 | m/z = 1050.38 ($C_{76}H_{50}N_4S$ = 1051.32) | P-32 | m/z = 894.37 ($C_{64}H_{34}D_9N_3S$ = 895.18) |
| P-33 | m/z = 943.36 ($C_{70}H_{45}N_3O$ = 944.15) | P-34 | m/z = 1049.34 ($C_{76}H_{47}N_3OS$ = 1050.29) |
| P-35 | m/z = 809.29 ($C_{58}H_{39}N_3S$ = 810.03) | P-36 | m/z = 1011.36 ($C_{74}H_{49}N_3S$ = 1012.19) |
| P-37 | m/z = 849.28 ($C_{60}H_{39}N_3OS$ = 850.05) | P-38 | m/z = 896.35 ($C_{65}H_{44}N_4O$ = 897.09) |
| P-39 | m/z = 710.28 ($C_{51}H_{38}N_2S$ = 710.94) | P-40 | m/z = 988.28 ($C_{69}H_{46}N_2S_3$ = 999.32) |
| P-41 | m/z = 926.42 ($C_{69}H_{54}N_2O$ = 927.20) | P-42 | m/z = 946.37 ($C_{69}H_{46}N_4O$ = 947.15) |
| P-43 | m/z = 834.41 ($C_{61}H_{42}N_2S$ = 835.08) | P-44 | m/z = 1069.39 ($C_{79}H_{52}N_2S$ = 1061.36) |
| P-45 | m/z = 1064.34 ($C_{77}H_{48}N_2O_2S$ = 1065.30) | P-46 | m/z = 1224.50 ($C_{93}H_{64}N_2O$ = 1225.55) |
| P-47 | m/z = 832.29 ($C_{61}H_{48}N_2O_2S$ = 1065.30) | P-48 | m/z = 1014.31 ($C_{73}H_{46}N_2S_2$ = 1015.31) |
| P-49 | m/z = 866.33 ($C_{65}H_{42}N_2O$ = 866.33) | P-50 | m/z = 1078.31 ($C_{77}H_{46}N_2OS_2$ = 1079.35) |
| P-51 | m/z = 852.26 ($C_{60}H_{40}N_2S_2$ = 853.11) | P-52 | m/z = 852.26 ($C_{60}H_{40}N_2S_2$ = 853.11) |
| P-53 | m/z = 700.20 ($C_{48}H_{32}N_2S_2$ = 700.92) | P-54 | m/z = 852.26 ($C_{60}H_{40}N_2S_2$ = 853.11) |
| P-55 | m/z = 852.26 ($C_{60}H_{40}N_2S_2$ = 853.11) | P-56 | m/z = 800.23 ($C_{56}H_{36}N_2S_2$ = 801.04) |
| P-57 | m/z = 896.20 ($C_{60}H_{36}N_2OS_3$ = 897.14) | P-58 | m/z = 896.20 ($C_{60}H_{36}N_2OS_3$ = 897.14) |
| P-59 | m/z = 841.22 ($C_{57}H_{35}N_3OS_2$ = 842.05) | P-60 | m/z = 849.24 ($C_{59}H_{35}N_3O_2S$ = 850.01) |
| P-61 | m/z = 980.25 ($C_{68}H_{40}N_2O_2S_2$ = 981.20) | P-62 | m/z = 1098.39 ($C_{80}H_{50}N_4O_2$ = 1099.31) |
| P-63 | m/z = 759.27 ($C_{54}H_{37}N_3S$ = 759.97) | P-64 | m/z = 961.35 ($C_{70}H_{47}N_3S$ = 962.23) |
| P-65 | m/z = 849.28 ($C_{60}H_{39}N_3OS$ = 850.05) | P-66 | m/z = 896.35 ($C_{65}H_{44}N_4O$ = 897.09) |
| P-67 | m/z = 710.28 ($C_{51}H_{38}N_2S$ = 710.94) | P-68 | m/z = 988.28 ($C_{69}H_{46}N_2S_3$ = 999.32) |
| P-69 | m/z = 912.18 ($C_{60}H_{36}N_2S_4$ = 913.20) | P-70 | m/z = 912.18 ($C_{60}H_{36}N_2S_4$ = 913.20) |
| P-71 | m/z = 880.22 ($C_{60}H_{36}N_2O_2S_2$ = 881.08) | P-72 | m/z = 880.22 ($C_{60}H_{36}N_2O_2S_2$ = 881.08) |
| P-73 | m/z = 946.21 ($C_{64}H_{38}N_2OS_3$ = 947.20) | P-74 | m/z = 1064.35 ($C_{76}H_{48}N_4OS$ = 1065.31) |
| P-75 | m/z = 684.22 ($C_{48}H_{32}N_2OS$ = 684.86) | P-76 | m/z = 836.29 ($C_{60}H_{40}N_2OS$ = 837.05) |
| P-77 | m/z = 915.27 ($C_{64}H_{41}N_3S_2$ = 916.17) | P-78 | m/z = 971.25 ($C_{66}H_{41}N_3S_3$ = 972.26) |
| P-79 | m/z = 1050.38 ($C_{76}H_{50}N_4S$ = 1051.32) | P-80 | m/z = 894.37 ($C_{64}H_{34}D_9N_3S$ = 895.18) |
| P-81 | m/z = 926.42 ($C_{69}H_{54}N_2O$ = 927.20) | P-82 | m/z = 946.37 ($C_{69}H_{46}N_4O$ = 947.15) |
| P-83 | m/z = 834.41 ($C_{61}H_{42}N_2S$ = 835.08) | P-84 | m/z = 1069.39 ($C_{79}H_{52}N_2S$ = 1061.36) |

Although the exemplary synthesis examples of the present disclosure represented by Formula (1) have been described above, the synthesis examples are on the basis of Buchwald-Hartwig cross coupling, N-alkylation (*J. Heterocyclic Chem* 2014, 51, 683; *Macromolecules* 2006, 39, 6951), H-mont-mediated etherification (*Tetrahedron* 2014, 70, 1975; *Org. Lett.* 2011, 13, 584), Miyaura boration, Suzuki cross-coupling, Intramolecular acid-induced cyclization (*J. mater. Chem.* 1999, 9, 2095.), Pd(II)-catalyzed oxidative cyclization (*Org. Lett.* 2011, 13, 5504), Grignard reaction, Cyclic Dehydration, and $PPh_3$-mediated reductive cyclization (*J. Org. Chem.* 2005, 70, 5014). A person skilled in the art could easily understand that the above reactions proceed even though, besides the substituents specified in the specific synthetic examples, other substituents defined in Formulas (1) and (2) are bound.

Manufacturing and Evaluation of Organic Electric Elements

[Example 1] Manufacturing and Test of Red Organic Light Emitting Diode

First, a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, abbreviated as "2-TNATA") as a hole injection layer was formed with a thickness of 60 nm through vacuum deposition on an ITO layer (anode) formed on a galas substrate. Then, N,N'-Bis(1-naphthalenyl)-N,N'-bis-phenyl-(1,1'-biphenyl)-4,4'-diamine (hereinafter, abbreviated as "NPB") was vacuum-deposited with a thickness of 60 nm to form a hole transport layer. Subsequently, the present inventive compound represented by Formula (1) as a material for an auxiliary light emitting layer was vacuum-deposited with a thickness of 20 nm to form an auxiliary light emitting layer. After the auxiliary light emitting layer was formed, a light emitting layer with a thickness of 30 nm was deposited on the auxiliary light emitting layer by doping an upper portion of the auxiliary light emitting layer with 4,4'-N,N'-dicarbazole-biphenyl (CBP) as a host and bis-(1-phenylisoquinolyl) iridium(□) acetylacetonate (($piq)_2Ir$ (acac)) as a dopant at a weight ratio of 95:5. Then, (1,1'-bisphenyl)-4-olato)bis(2-methyl-8-quinolinolato)aluminum (hereinafter abbreviated as "BAlq") was vacuum-deposited with a thickness of 10 nm for a hole blocking layer, and tris(8-quinolinol) aluminum (hereinafter abbreviated as "$Alq_3$") was formed with a thickness of 40 nm for an electron injection layer. Thereafter, LiF, the halogenated alkali metal, was deposited with a thickness of 0.2 nm for an electron injection layer, and subsequently Al was deposited with a thickness of 150 nm and used as a negative electrode. In this way, an organic electric light emitting diode was manufactured.

A forward bias DC voltage was applied to each of organic light emitting diodes manufactured in examples and comparative examples to measure electro-luminescent (EL) characteristics thereof by PR-650 (Photoresearch). Also, the T95 lifespan was measured by a lifespan measurement equipment (fabricated by Mcscience) at reference brightness of 2500 cd/m². The element manufacturing and evaluation results are shown in the table below.

Comparative Example 1

Organic light emitting diodes were manufactured by the same method as in Example 1 except that the auxiliary light emitting layer is not used.

Comparative Examples 2 to 5

Organic light emitting diodes were manufactured by the same method as in Example 1 except that Comparative compounds A to D below were used as materials for the auxiliary light emitting layer.

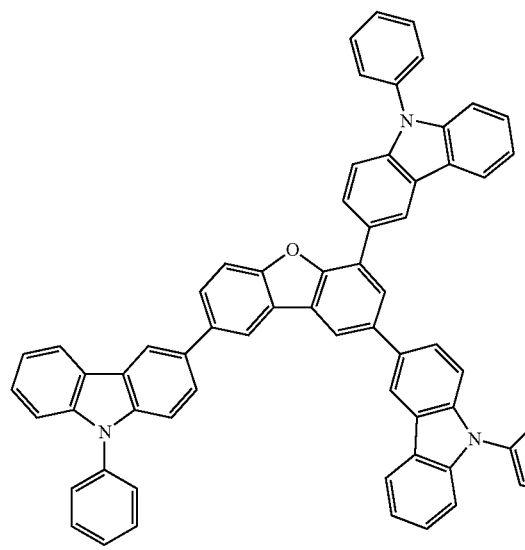

Comparative Compound A

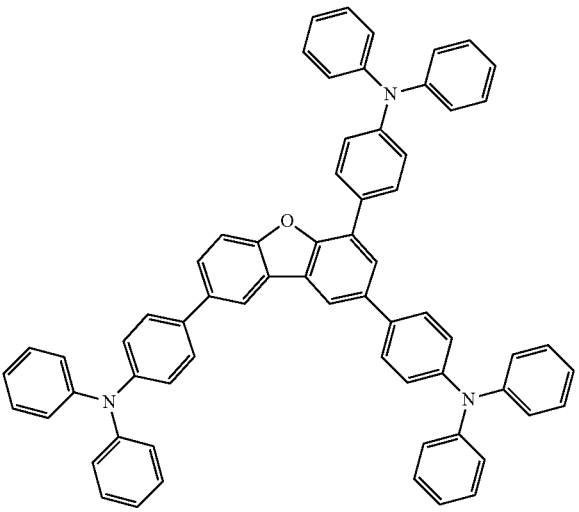

Comparative Compound B

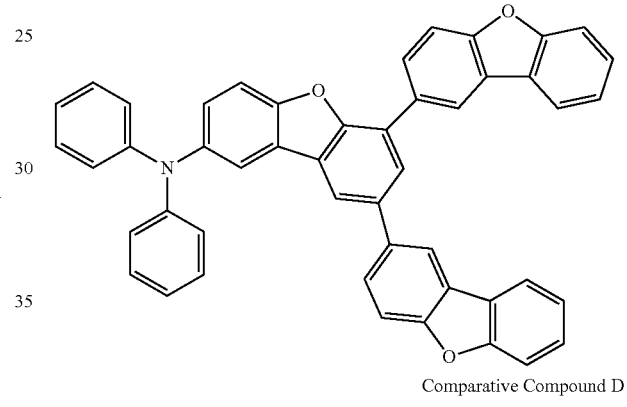

Comparative Compound C

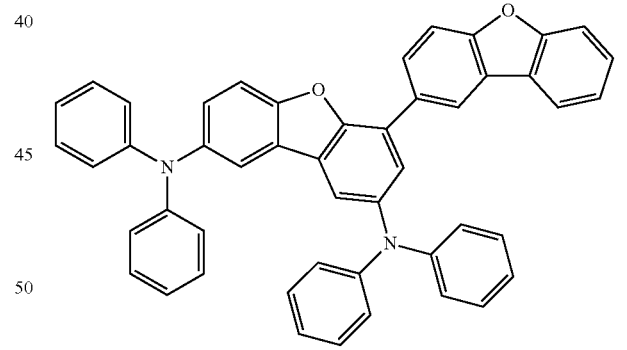

Comparative Compound D

TABLE 4

|  | Compound | Voltage | Current Density | Brightness (cd/m2) | Efficiency | Lifetime T(95) | CIE (x, y) |
|---|---|---|---|---|---|---|---|
| Comparative Example (1) | — | 6.0 | 32.9 | 2500.0 | 7.6 | 61.8 | (0.66, 0.32) |
| Comparative Example (2) | Comparative Compound A | 6.2 | 30.1 | 2500.0 | 8.3 | 80.3 | (0.67, 0.32) |
| Comparative Example (3) | Comparative Compound B | 5.8 | 24.5 | 2500.0 | 10.2 | 100.9 | (0.66, 0.35) |
| Comparative Example (4) | Comparative Compound C | 6.1 | 26.6 | 2500.0 | 9.4 | 94.2 | (0.66, 0.35) |

TABLE 4-continued

| | Compound | Voltage | Current Density | Brightness (cd/m2) | Efficiency | Lifetime T(95) | CIE (x, y) |
|---|---|---|---|---|---|---|---|
| Comparative Example (5) | Comparative Compound D | 6.0 | 27.8 | 2500.0 | 9.0 | 98.5 | (0.67, 0.32) |
| Example (1) | Compound (P-1) | 4.3 | 7.9 | 2500.0 | 31.7 | 125.9 | (0.66, 0.32) |
| Example (2) | Compound (P-2) | 4.1 | 8.1 | 2500.0 | 30.7 | 125.1 | (0.66, 0.35) |
| Example (3) | Compound (P-3) | 4.2 | 8.2 | 2500.0 | 30.5 | 126.1 | (0.66, 0.35) |
| Example (4) | Compound (P-4) | 4.2 | 7.9 | 2500.0 | 31.7 | 125.3 | (0.65, 0.35) |
| Example (5) | Compound (P-5) | 4.3 | 7.9 | 2500.0 | 31.8 | 126.8 | (0.65, 0.35) |
| Example (6) | Compound (P-6) | 4.0 | 8.2 | 2500.0 | 30.6 | 126.5 | (0.66, 0.35) |
| Example (7) | Compound (P-7) | 4.0 | 8.1 | 2500.0 | 30.9 | 126.0 | (0.66, 0.35) |
| Example (8) | Compound (P-8) | 4.1 | 8.1 | 2500.0 | 30.8 | 125.2 | (0.66, 0.35) |
| Example (9) | Compound (P-9) | 4.1 | 7.8 | 2500.0 | 31.9 | 125.5 | (0.66, 0.35) |
| Example (10) | Compound (P-10) | 4.2 | 7.9 | 2500.0 | 31.8 | 125.9 | (0.66, 0.35) |
| Example (11) | Compound (P-11) | 4.9 | 11.3 | 2500.0 | 22.1 | 116.2 | (0.66, 0.35) |
| Example (12) | Compound (P-12) | 4.6 | 8.9 | 2500.0 | 28.0 | 121.4 | (0.66, 0.35) |
| Example (13) | Compound (P-13) | 4.5 | 9.1 | 2500.0 | 27.4 | 121.2 | (0.66, 0.35) |
| Example (14) | Compound (P-14) | 4.6 | 9.0 | 2500.0 | 27.7 | 120.0 | (0.66, 0.35) |
| Example (15) | Compound (P-15) | 4.5 | 8.8 | 2500.0 | 28.4 | 122.9 | (0.66, 0.35) |
| Example (16) | Compound (P-16) | 4.5 | 8.7 | 2500.0 | 28.8 | 122.9 | (0.66, 0.35) |
| Example (17) | Compound (P-17) | 4.5 | 8.9 | 2500.0 | 28.0 | 121.9 | (0.66, 0.35) |
| Example (18) | Compound (P-18) | 4.5 | 9.1 | 2500.0 | 27.6 | 120.1 | (0.66, 0.32) |
| Example (19) | Compound (P-19) | 4.3 | 8.8 | 2500.0 | 28.5 | 122.5 | (0.66, 0.35) |
| Example (20) | Compound (P-20) | 4.2 | 8.9 | 2500.0 | 28.2 | 120.2 | (0.66, 0.35) |
| Example (21) | Compound (P-21) | 4.1 | 8.6 | 2500.0 | 29.0 | 121.7 | (0.65, 0.35) |
| Example (22) | Compound (P-22) | 4.2 | 9.1 | 2500.0 | 27.6 | 121.5 | (0.65, 0.35) |
| Example (23) | Compound (P-23) | 4.1 | 8.6 | 2500.0 | 28.9 | 120.5 | (0.65, 0.35) |
| Example (24) | Compound (P-24) | 4.0 | 9.2 | 2500.0 | 27.1 | 121.6 | (0.66, 0.32) |
| Example (25) | Compound (P-25) | 4.9 | 11.9 | 2500.0 | 21.0 | 115.6 | (0.66, 0.35) |
| Example (26) | Compound (P-26) | 5.0 | 11.4 | 2500.0 | 21.9 | 115.3 | (0.66, 0.35) |
| Example (27) | Compound (P-27) | 4.6 | 10.2 | 2500.0 | 24.4 | 118.9 | (0.65, 0.35) |
| Example (28) | Compound (P-28) | 4.7 | 10.3 | 2500.0 | 24.2 | 118.7 | (0.65, 0.35) |
| Example (29) | Compound (P-29) | 4.6 | 10.2 | 2500.0 | 24.4 | 118.4 | (0.66, 0.35) |
| Example (30) | Compound (P-30) | 4.8 | 10.4 | 2500.0 | 23.9 | 117.6 | (0.66, 0.35) |
| Example (31) | Compound (P-31) | 4.7 | 10.3 | 2500.0 | 24.2 | 118.2 | (0.66, 0.35) |
| Example (32) | Compound (P-32) | 4.7 | 10.1 | 2500.0 | 24.7 | 118.5 | (0.66, 0.35) |
| Example (33) | Compound (P-33) | 4.7 | 10.5 | 2500.0 | 23.9 | 117.7 | (0.66, 0.35) |
| Example (34) | Compound (P-34) | 4.7 | 10.4 | 2500.0 | 24.0 | 117.2 | (0.66, 0.35) |
| Example (35) | Compound (P-35) | 4.6 | 10.3 | 2500.0 | 24.4 | 119.0 | (0.66, 0.35) |
| Example (36) | Compound (P-36) | 4.7 | 10.3 | 2500.0 | 24.2 | 118.6 | (0.66, 0.35) |
| Example (37) | Compound (P-37) | 4.6 | 10.1 | 2500.0 | 24.6 | 118.9 | (0.66, 0.35) |

TABLE 4-continued

| | Compound | Voltage | Current Density | Brightness (cd/m2) | Efficiency | Lifetime T(95) | CIE (x, y) |
|---|---|---|---|---|---|---|---|
| Example (38) | Compound (P-38) | 4.7 | 10.5 | 2500.0 | 23.8 | 117.5 | (0.66, 0.35) |
| Example (39) | Compound (P-39) | 5.2 | 13.1 | 2500.0 | 19.0 | 113.5 | (0.66, 0.35) |
| Example (40) | Compound (P-40) | 5.2 | 13.4 | 2500.0 | 18.7 | 114.5 | (0.66, 0.35) |
| Example (41) | Compound (P-41) | 5.1 | 13.4 | 2500.0 | 18.6 | 114.4 | (0.66, 0.32) |
| Example (42) | Compound (P-42) | 5.1 | 13.3 | 2500.0 | 18.8 | 113.3 | (0.66, 0.35) |
| Example (43) | Compound (P-43) | 5.0 | 13.1 | 2500.0 | 19.1 | 114.3 | (0.66, 0.35) |
| Example (44) | Compound (P-44) | 5.1 | 12.7 | 2500.0 | 19.7 | 113.5 | (0.65, 0.35) |
| Example (45) | Compound (P-45) | 5.2 | 13.4 | 2500.0 | 18.7 | 113.0 | (0.65, 0.35) |
| Example (46) | Compound (P-46) | 5.1 | 13.8 | 2500.0 | 18.1 | 114.8 | (0.65, 0.35) |
| Example (47) | Compound (P-47) | 5.1 | 12.6 | 2500.0 | 19.9 | 114.1 | (0.66, 0.32) |
| Example (48) | Compound (P-48) | 5.1 | 12.8 | 2500.0 | 19.6 | 113.4 | (0.66, 0.35) |
| Example (49) | Compound (P-49) | 5.0 | 13.6 | 2500.0 | 18.3 | 113.5 | (0.66, 0.35) |
| Example (50) | Compound (P-50) | 5.1 | 12.7 | 2500.0 | 19.6 | 113.9 | (0.65, 0.35) |
| Example (51) | Compound (P-51) | 4.0 | 8.4 | 2500.0 | 29.7 | 123.8 | (0.65, 0.35) |
| Example (52) | Compound (P-52) | 4.2 | 8.4 | 2500.0 | 29.9 | 122.4 | (0.66, 0.35) |
| Example (53) | Compound (P-53) | 4.3 | 8.0 | 2500.0 | 31.1 | 126.1 | (0.66, 0.35) |
| Example (54) | Compound (P-54) | 4.3 | 8.0 | 2500.0 | 31.4 | 125.5 | (0.66, 0.35) |
| Example (55) | Compound (P-55) | 4.1 | 8.1 | 2500.0 | 30.9 | 126.9 | (0.66, 0.35) |
| Example (56) | Compound (P-56) | 4.3 | 8.3 | 2500.0 | 30.1 | 125.2 | (0.66, 0.35) |
| Example (57) | Compound (P-57) | 4.6 | 9.1 | 2500.0 | 27.5 | 120.6 | (0.66, 0.35) |
| Example (58) | Compound (P-58) | 4.5 | 8.7 | 2500.0 | 28.7 | 122.1 | (0.66, 0.35) |
| Example (59) | Compound (P-59) | 4.5 | 8.8 | 2500.0 | 28.3 | 121.3 | (0.66, 0.35) |
| Example (60) | Compound (P-60) | 4.4 | 8.8 | 2500.0 | 28.5 | 122.8 | (0.66, 0.35) |
| Example (61) | Compound (P-61) | 4.8 | 11.1 | 2500.0 | 22.5 | 115.7 | (0.66, 0.35) |
| Example (62) | Compound (P-62) | 5.0 | 11.5 | 2500.0 | 21.7 | 115.7 | (0.66, 0.35) |
| Example (63) | Compound (P-63) | 4.7 | 10.7 | 2500.0 | 23.4 | 118.3 | (0.66, 0.35) |
| Example (64) | Compound (P-64) | 4.7 | 10.7 | 2500.0 | 23.4 | 118.2 | (0.66, 0.32) |
| Example (65) | Compound (P-65) | 4.8 | 10.1 | 2500.0 | 24.8 | 118.6 | (0.66, 0.35) |
| Example (66) | Compound (P-66) | 4.7 | 10.1 | 2500.0 | 24.8 | 118.1 | (0.66, 0.35) |
| Example (67) | Compound (P-67) | 5.1 | 13.6 | 2500.0 | 18.4 | 114.6 | (0.65, 0.35) |
| Example (68) | Compound (P-68) | 5.1 | 13.3 | 2500.0 | 18.7 | 113.6 | (0.65, 0.35) |
| Example (69) | Compound (P-69) | 4.7 | 7.9 | 2500.0 | 31.7 | 125.0 | (0.65, 0.35) |
| Example (70) | Compound (P-70) | 4.7 | 8.2 | 2500.0 | 30.5 | 125.1 | (0.66, 0.32) |
| Example (71) | Compound (P-71) | 4.7 | 8.0 | 2500.0 | 31.1 | 126.6 | (0.66, 0.35) |
| Example (72) | Compound (P-72) | 4.6 | 8.0 | 2500.0 | 31.1 | 127.0 | (0.66, 0.35) |
| Example (73) | Compound (P-73) | 4.7 | 8.9 | 2500.0 | 28.1 | 122.8 | (0.65, 0.35) |
| Example (74) | Compound (P-74) | 4.7 | 9.1 | 2500.0 | 27.5 | 122.1 | (0.65, 0.35) |
| Example (75) | Compound (P-75) | 4.6 | 9.1 | 2500.0 | 27.5 | 121.5 | (0.66, 0.35) |

TABLE 4-continued

| | Compound | Voltage | Current Density | Brightness (cd/m2) | Efficiency | Lifetime T(95) | CIE (x, y) |
|---|---|---|---|---|---|---|---|
| Example (76) | Compound (P-76) | 4.8 | 9.1 | 2500.0 | 27.4 | 121.3 | (0.66, 0.35) |
| Example (77) | Compound (P-77) | 4.7 | 10.4 | 2500.0 | 24.0 | 118.0 | (0.66, 0.35) |
| Example (78) | Compound (P-78) | 4.8 | 10.2 | 2500.0 | 24.5 | 118.7 | (0.66, 0.35) |
| Example (79) | Compound (P-79) | 4.7 | 10.2 | 2500.0 | 24.6 | 117.5 | (0.66, 0.35) |
| Example (80) | Compound (P-80) | 4.7 | 10.7 | 2500.0 | 23.4 | 117.2 | (0.66, 0.35) |
| Example (81) | Compound (P-81) | 5.0 | 13.0 | 2500.0 | 19.2 | 113.7 | (0.66, 0.35) |
| Example (82) | Compound (P-82) | 5.0 | 13.0 | 2500.0 | 19.3 | 113.3 | (0.66, 0.35) |
| Example (83) | Compound (P-83) | 5.0 | 12.7 | 2500.0 | 19.6 | 114.8 | (0.66, 0.35) |
| Example (84) | Compound (P-84) | 5.0 | 12.8 | 2500.0 | 19.5 | 114.6 | (0.66, 0.35) |

As can be seen from the results of Table 4, when a red organic light emitting device was manufactured using the material for an organic light emitting device of the present disclosure as a material for the light emitting auxiliary layer, the driving voltage of the organic light emitting device can be lowered and the luminous efficiency and lifespan can be remarkably improved as compared with the comparative examples in which an auxiliary light emitting auxiliary layer was not used or Comparative Compounds A to D were used.

In other words, it is shown that the results of Comparative Examples 2 to 5 using Comparative Compounds A to D were superior to those of Comparative Example 1 using no auxiliary light emitting layer, and the results of Examples 1 to 84 of the present inventive compounds were superior to those of the comparative examples using comparative compounds.

In Comparative Compounds A to D, Comparative Compound A in which all heteroaryl groups (carbazole) were substituted at the same substitution positions as in the present inventive compounds in Dibenzofuran showed a slower driving voltage by about 0.2 eV but improved results in efficiency and lifespan, as compared with Comparative Example 1 in which an auxiliary light emitting layer was not used. Comparative Compounds C and D, which were different from the present inventive compounds in light of the kind and substitution position of substituent, showed an equivalent or slightly increased driving voltage but improved results in efficiency and lifespan.

It can be confirmed that Comparative Compound D and the present inventive compounds were similar in the kind of substituent but different in the substitution position of the substituent, but the elements results thereof were significantly different. It is indicated that although the compounds had similar cores, the physical properties of the compounds, such as hole characteristics, luminous efficiency characteristics, energy levels (LUMO level, HOMO level, $T_1$ level), hole injection and mobility characteristics, and electron blocking characteristics may vary according to the kind of substituent or the substitution position of the substituent, so that totally different device results could be derived.

In addition, the characteristics of elements have been described in view of an auxiliary light emitting layer with reference to the foregoing evaluation results of the manufacture of elements, but the materials used for the auxiliary light emitting layer may be ordinarily used alone or in a mixture with other materials, for the foregoing electron transport layer, electron injection layer, hole injection layer, hole transport layer, light emitting layer, and auxiliary electron transport layer. Therefore, for the foregoing reasons, the compounds of the present disclosure may be used alone or in a mixture with other materials, for the other layers for the organic material layer, excluding the auxiliary light emitting layer, for example, an electron transport layer, an electron injection layer, a hole injection layer, a hole transport layer, a light emitting layer, and an auxiliary electron transport layer.

Although exemplary embodiments of the present disclosure have been described for illustrative purposes, a person skilled in the art will appreciate that various modifications, additions, and substitutions are possible, without departing from the scope and spirit of the disclosure as disclosed in the accompanying claims. Therefore, the embodiment disclosed in the present disclosure is intended to illustrate the scope of the technical idea of the present disclosure, and the scope of the present disclosure is not limited by the embodiment. The scope of the present disclosure shall be construed on the basis of the accompanying claims, and it shall be construed that all of the technical ideas included within the scope equivalent to the claims belong to the present disclosure.

The invention claimed is:

1. A compound represented by Formula (1):

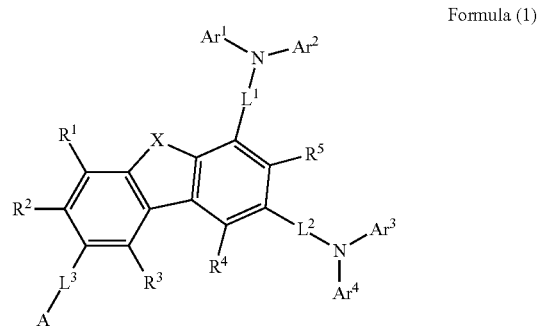

Formula (1)

wherein in Formula (1),
1) A is one of

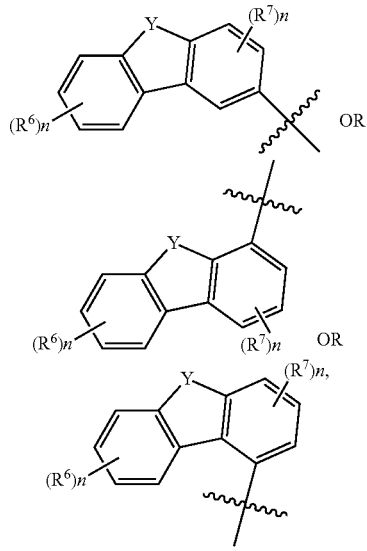

2) X is O or S,
3) $R^1$, $R^2$, $R^3$, $R^4$, $R^5$, $R^6$, and $R^7$ are independently selected from the group consisting of hydrogen; deuterium; halogen; a $C_6$-$C_{60}$ aryl group; a fluorenyl group; a $C_2$-$C_{60}$ heterocyclic group containing at least one heteroatom of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and —L'—N($R_a$)($R_b$) (wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group, and wherein $R_a$ and $R_b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one heteroatom of O, N, S, Si, and P),
4) $L^1$, $L^2$ and $L^3$ are independently selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group containing at least one heteroatom of O, N, S, Si, and P,
5) $Ar^1$, $Ar^2$, $Ar^3$, $Ar^4$, $Ar^5$, and $Ar^6$ are independently selected from the group consisting of a $C_6$-$C_{60}$ aryl group; a fluorenyl group; a $C_2$-$C_{60}$ heterocyclic group containing at least one heteroatom of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and —L'—N($R_a$)($R_b$),
6) Y is selected from the group consisting of O, S, and CR'R", wherein R' and R" are hydrogen; a $C_6$-$C_{60}$ aryl group; a fluorenyl group; a $C_3$-$C_{60}$ heterocyclic group; a $C_1$-$C_{50}$ alkyl group; a $C_2$-$C_{60}$ alkenyl group; and a $C_6$-$C_{60}$ aryloxy group, wherein R' and R" may be linked to each other to form a spiro ring, and 7) n is an integer of 0 to 4 and m is an integer of 0 to 3, wherein the aryl group, fluorenyl group, heterocyclic group, fused ring group, alkyl group, alkenyl group, alkynyl group, alkoxy group, aryloxy group, alkylene group, arylene group, fluorenylene group, carbonyl group, arylalkyl group, alkenyloxy group, ether group, alkenylaryl group, cycloalkyl group, silane group, siloxane group, arylalkoxy group, arylalkenyl group, and alkoxycarbonyl group may independently be further substituted with at least one substituent selected from the group consisting of deuterium, halogen, a silane group, a siloxane group, a boron group, a germanium group, a cyano group, a nitro group, —$L^b$—N($R^e$)($R^f$) (here, $L^b$, $R^e$, $R^f$ being the same as $L^a$, $R^c$ and $R^d$ each defined above, respectively), a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, a $C_8$-$C_{20}$ arylalkenyl group, a carbonyl group, an ether group, a $C_2$-$C_{20}$ alkoxycarbonyl group, $C_6$-$C_{30}$ aryloxy group, —O—Si($R^g$)$_3$, and $R^h$O—Si($R^g$)$_2$— (here, $R^g$ being the same as $R^a$ defined above and $R^h$ being the same as $R^b$ defined above).

2. The compound of claim 1, wherein adjacent $R^1$ and $R^2$, a plurality of $R^6$'s, or a plurality of $R^7$'s may be linked to each other to form an aromatic or heteroaromatic ring.

3. The compound of claim 1, wherein the compound represented by Formula (1) above is represented by one of Formulas (2) to (4) below:

Formula (2)

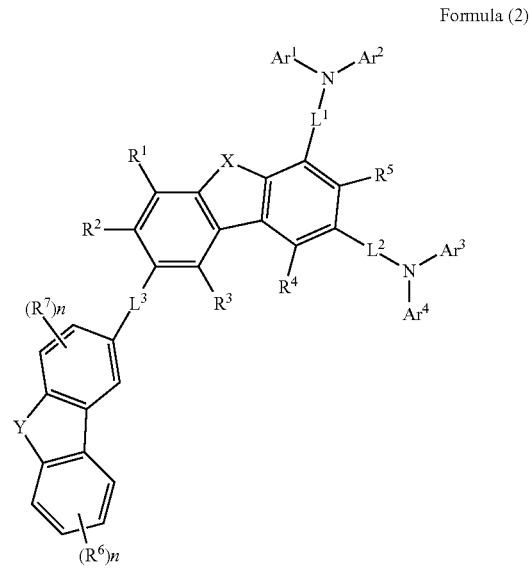

Formula (3)
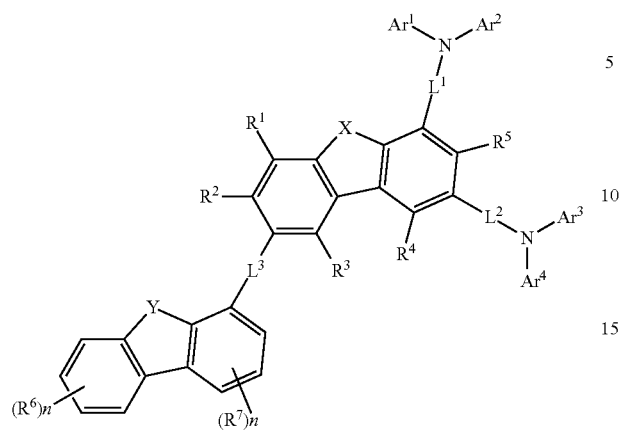
Formula (4)
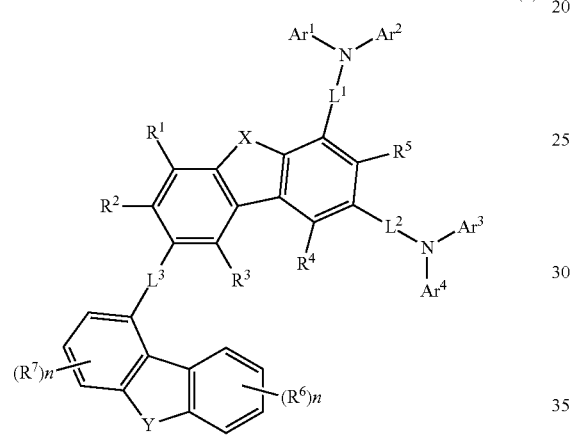
wherein in Formulas (2) to (4),
R$^1$, R$^2$, R$^3$, R$^4$, R$^5$, R$^6$, R$^7$, m, n, L$^1$, L$^2$, Ar$^1$, Ar$^2$, Ar$^3$, Ar$^4$, X, and Y are the same as R$^1$, R$^2$, R$^3$, R$^4$, R$^5$, R$^6$, R$^7$, m, n, L$^1$, L$^2$, L$^3$, Ar$^1$, Ar$^2$, Ar$^3$, Ar$^4$, X, and Y defined in Formula (1) above, respectively.
4. The compound of claim 1, wherein the compound represented by Formula (1) is one of the compounds below:
P-1
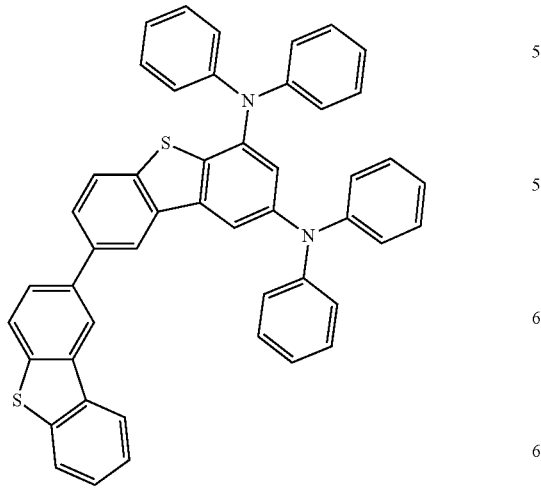
P-2
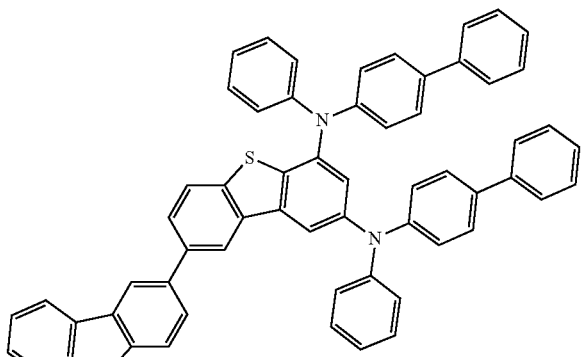
P-3
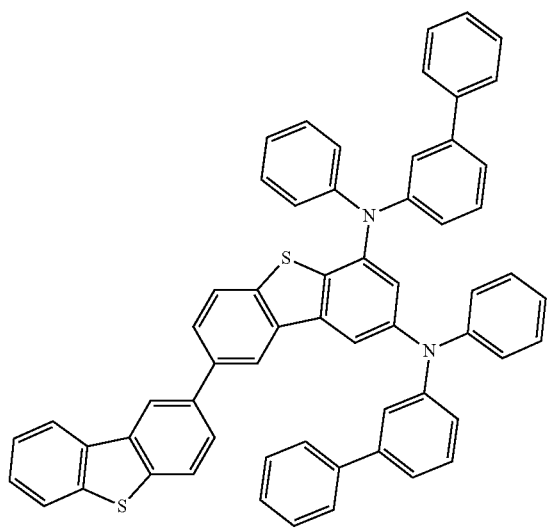
P-4
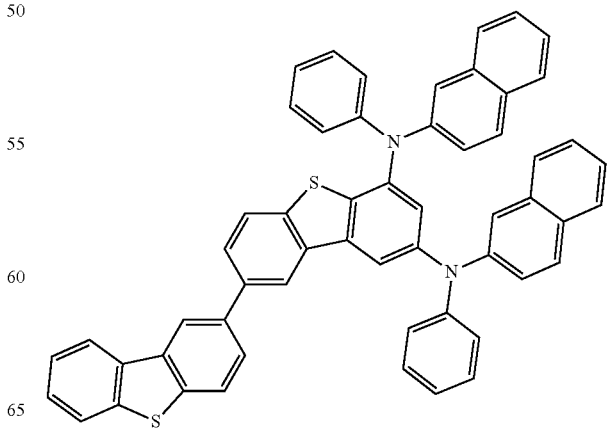

-continued
P-5
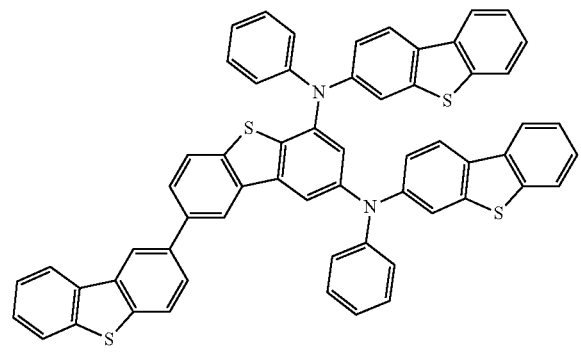
P-6
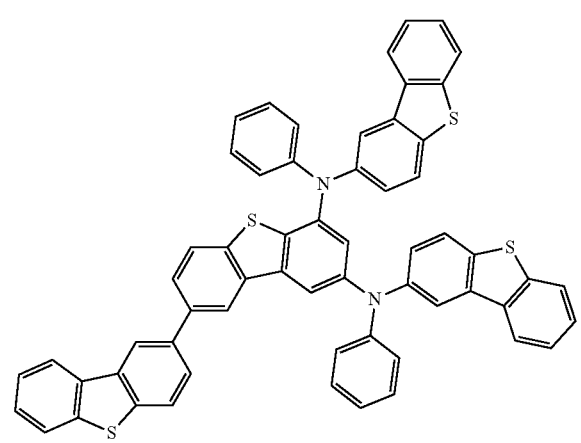
P-7
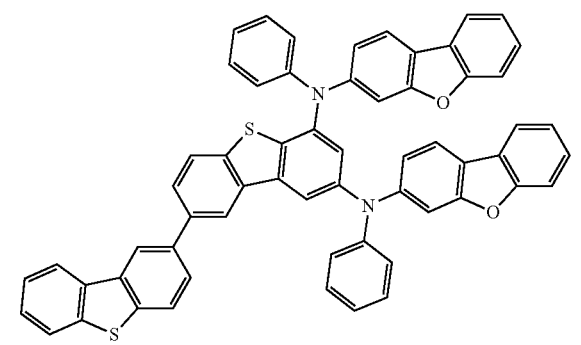
P-8
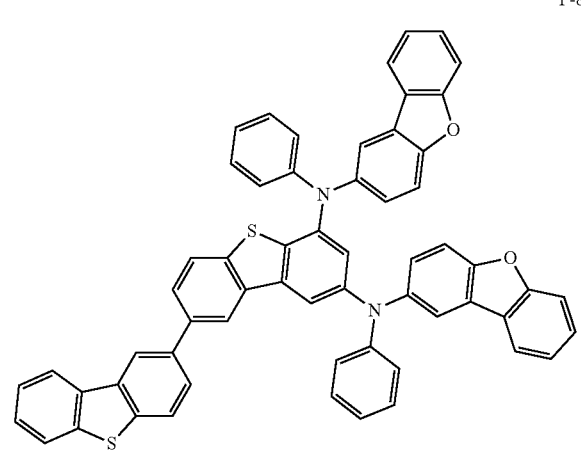
P-9
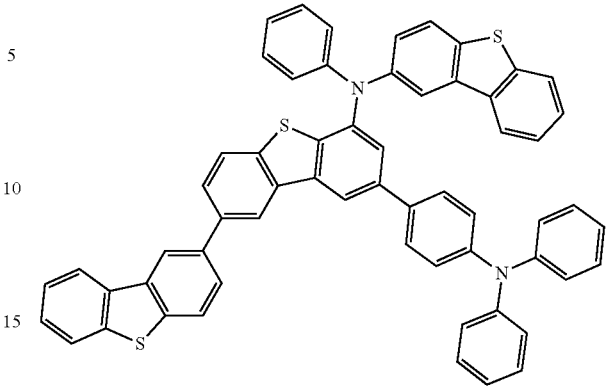
P-10
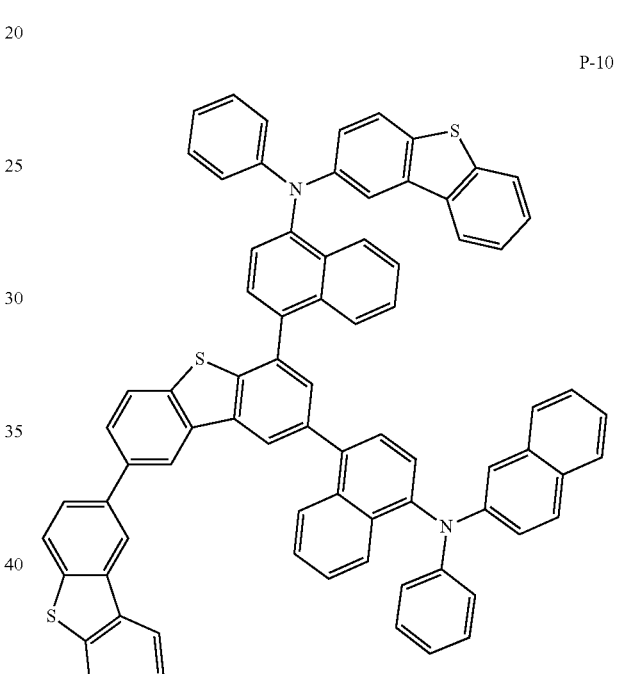
P-11
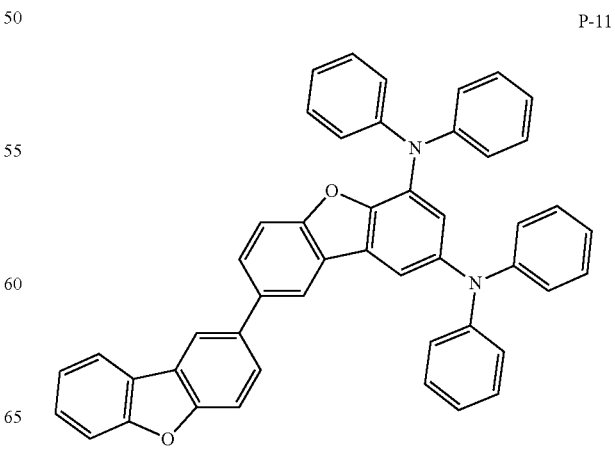

P-12
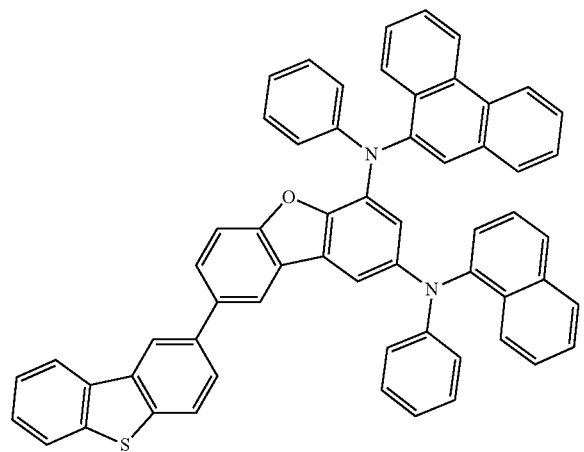
P-13
P-14
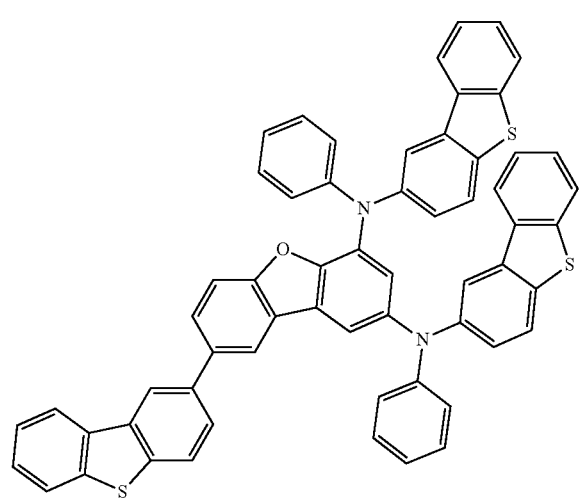
P-15
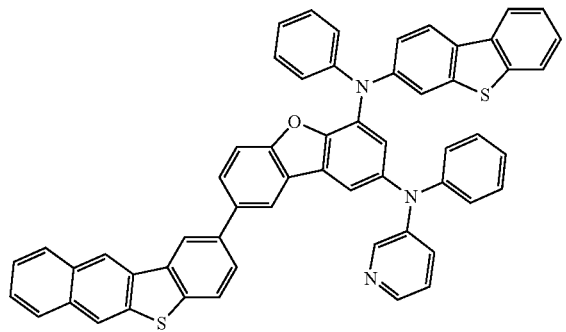
P-16
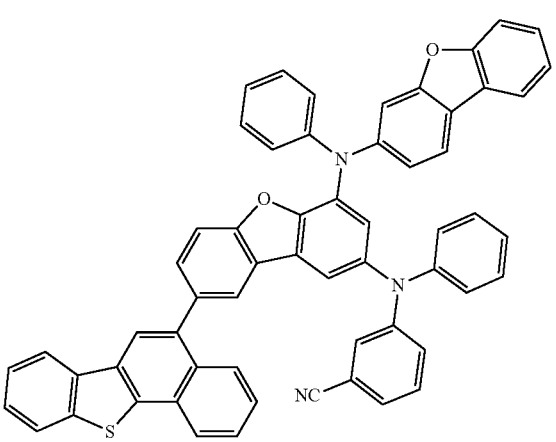
P-17
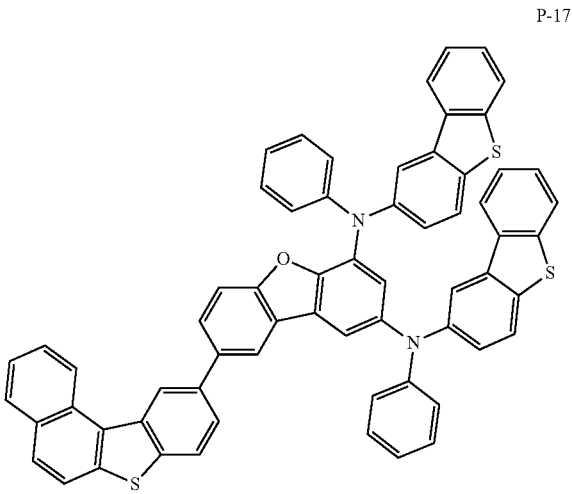

P-18
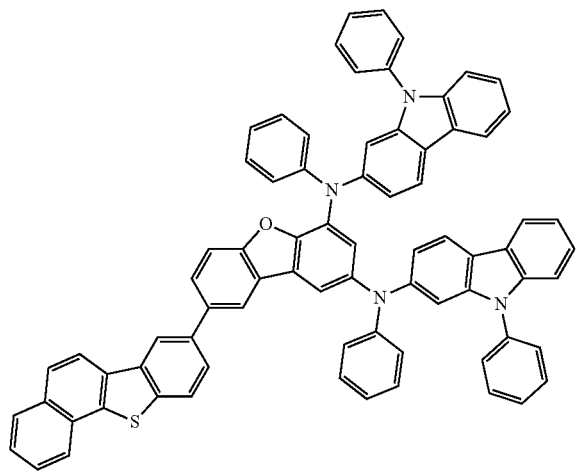
P-19
P-20
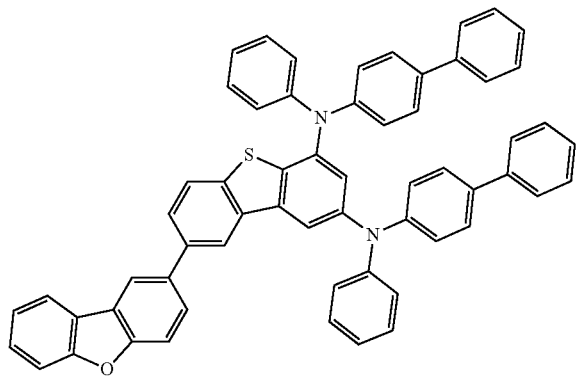
P-21
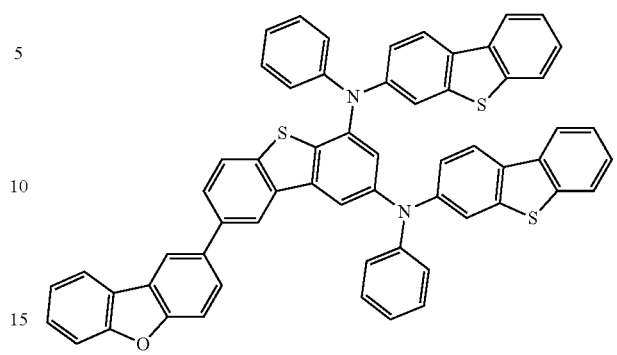
P-22
P-23
P-24
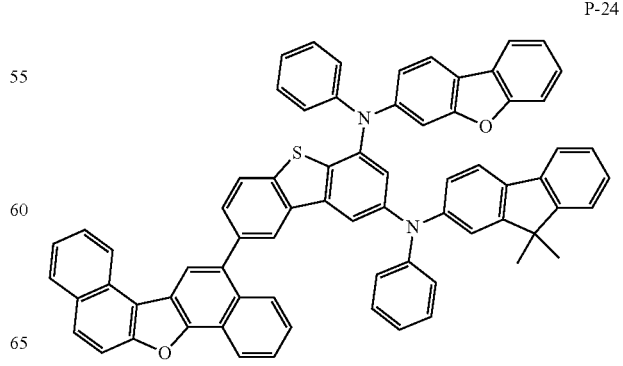

P-25
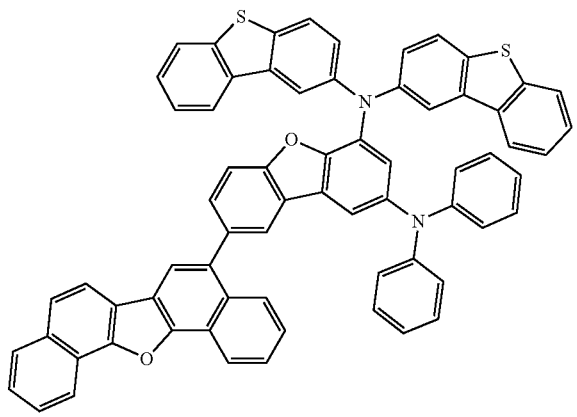
P-40
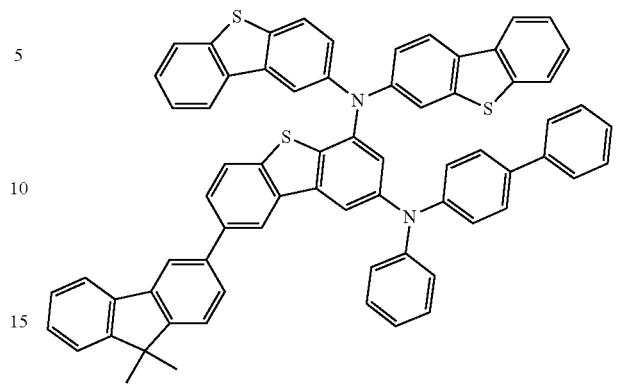
P-26
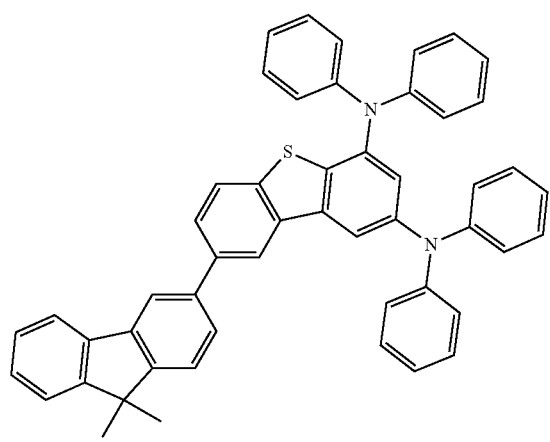
P-41
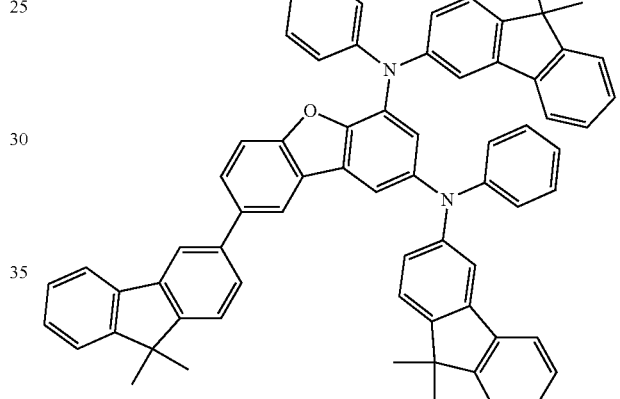
P-39
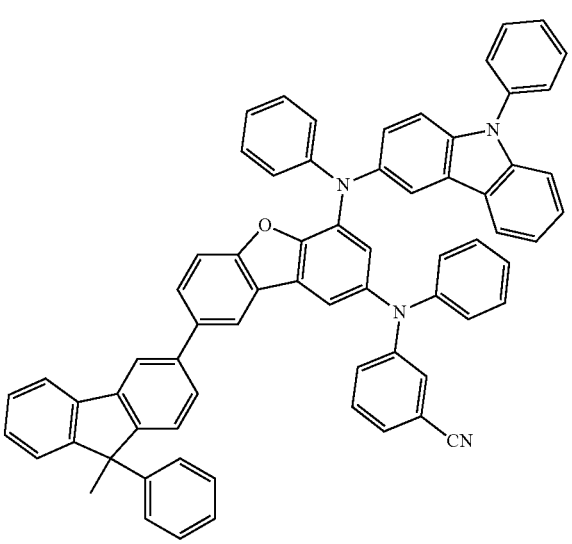
P-42

-continued
P-43
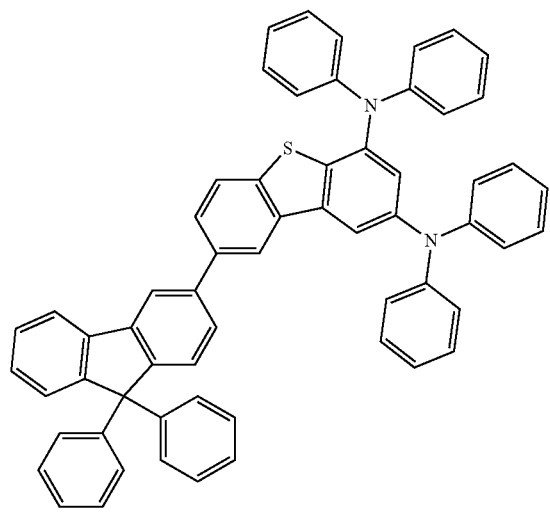
P-44
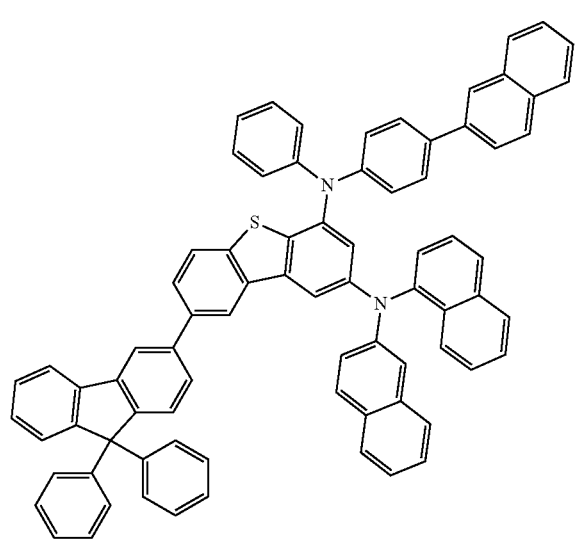
P-45
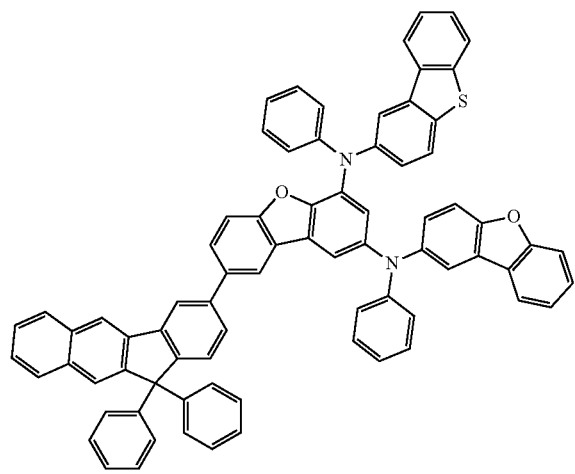
-continued
P-46
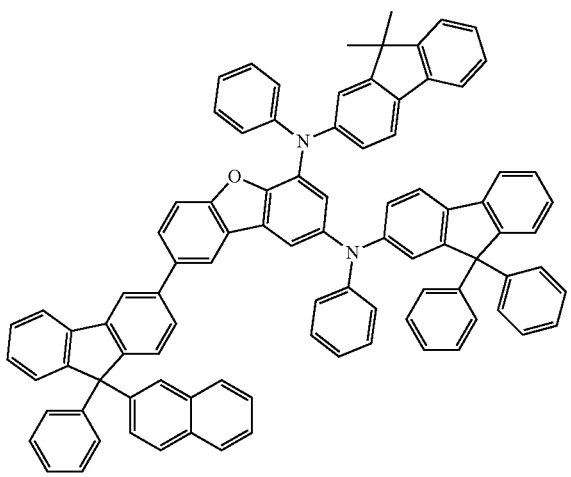
P-47
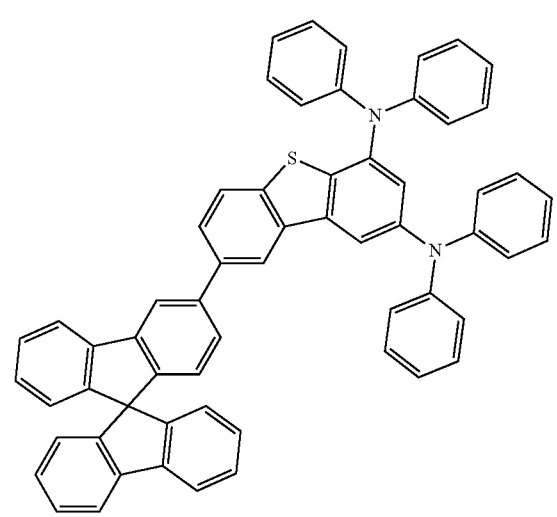
P-48
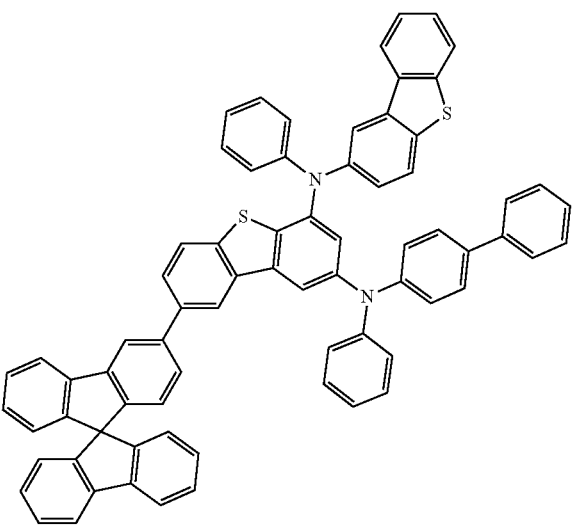

P-49
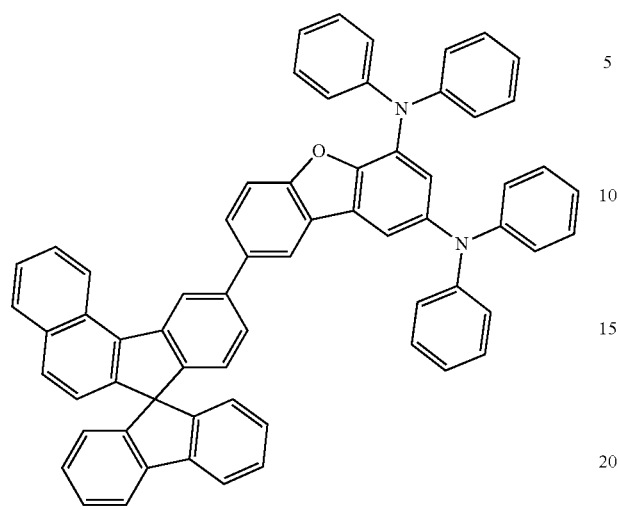
P-50
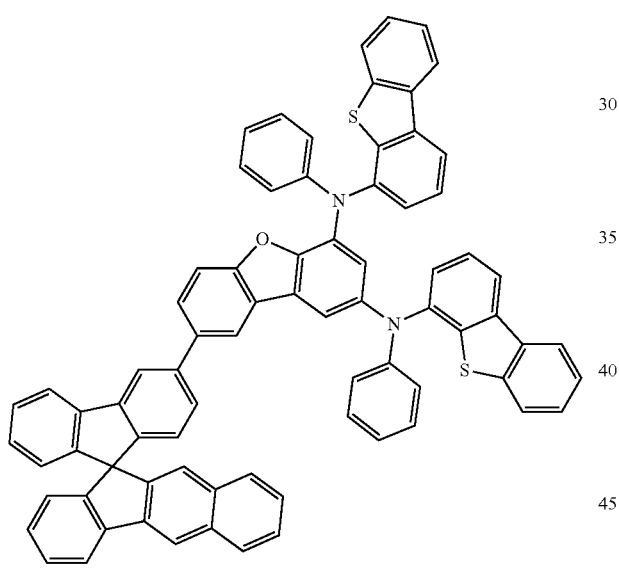
P-51
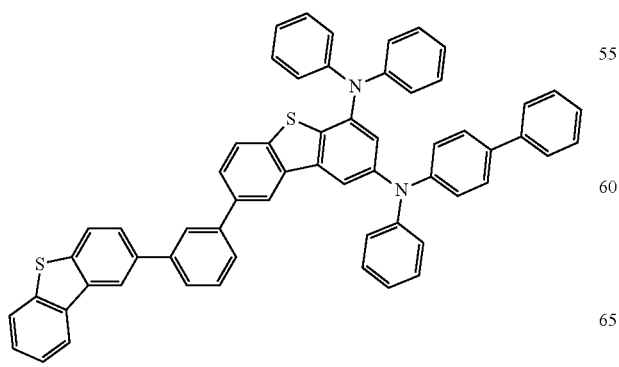
P-52
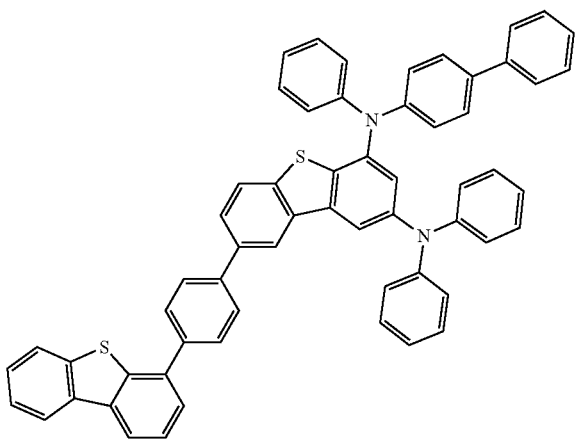
P-53
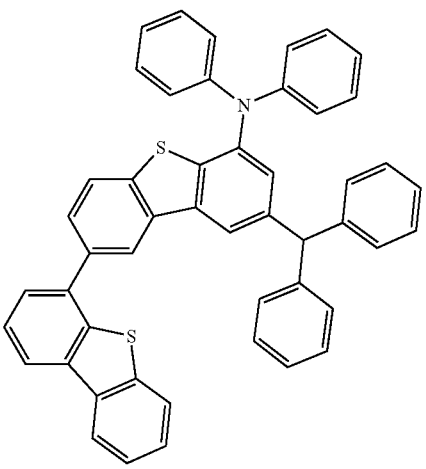
P-54
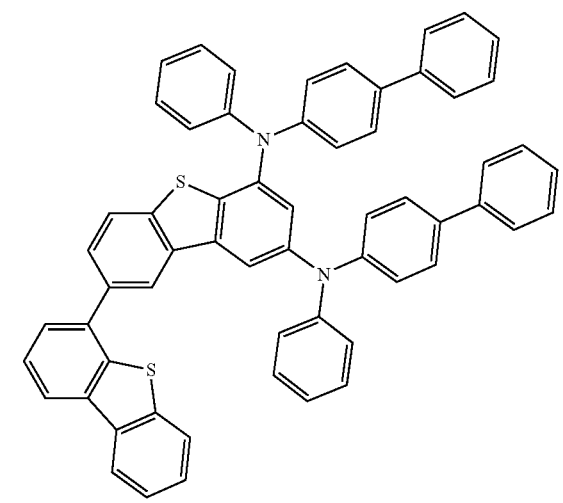

-continued

P-55

P-56

P-57

P-58

P-59

P-60

P-61
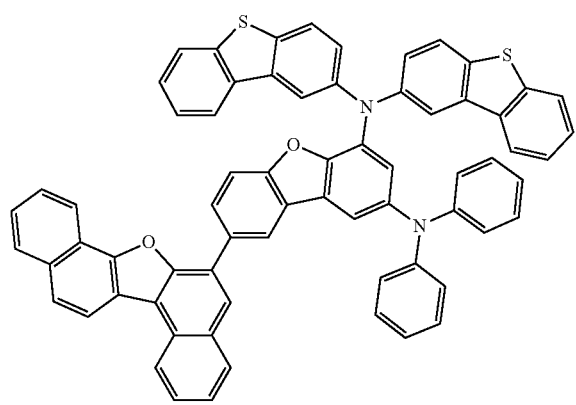
P-68
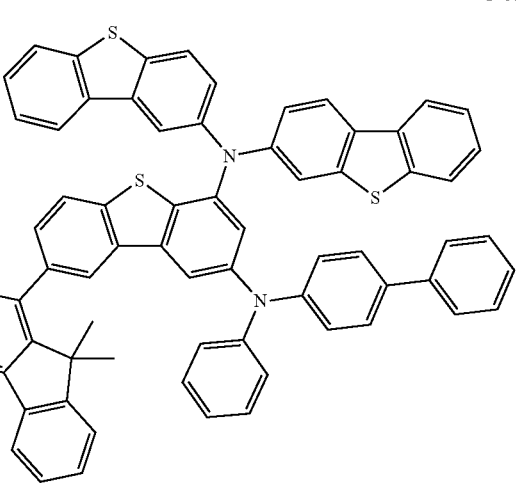
P-62
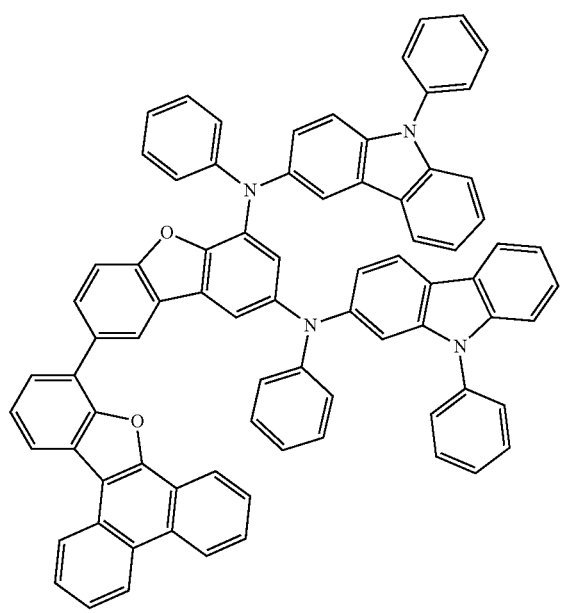
P-69
P-67
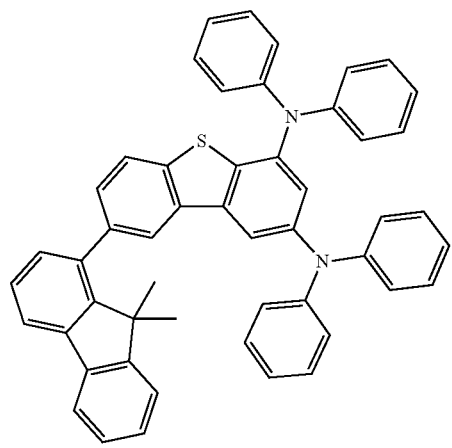
P-70
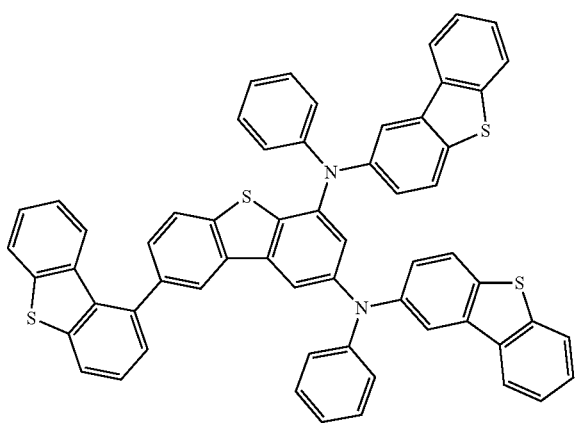

-continued
P-71
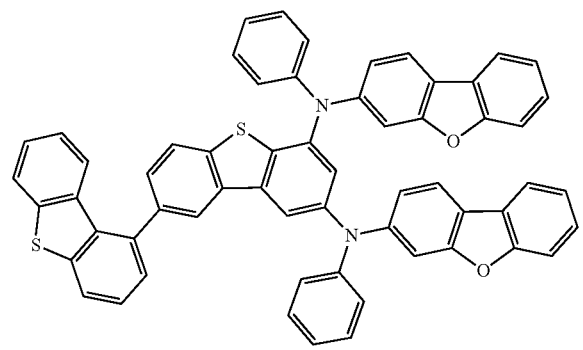
P-72
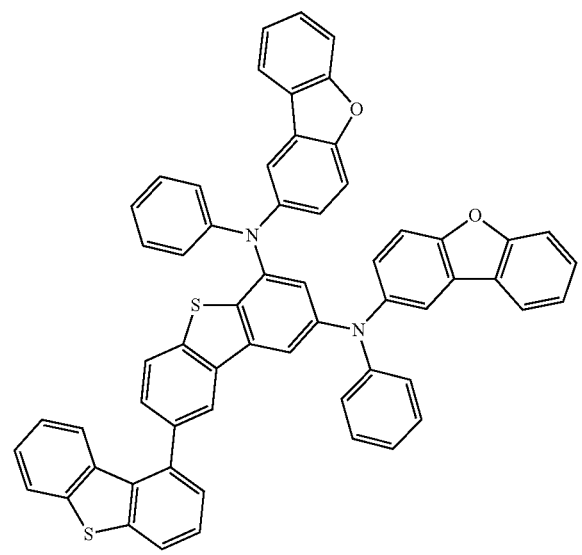
P-73
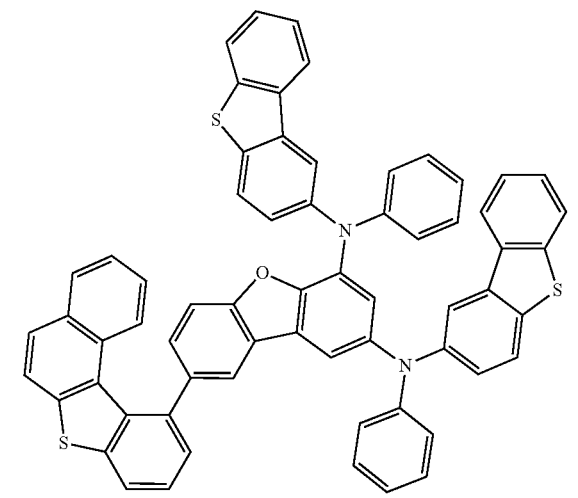
-continued
P-74
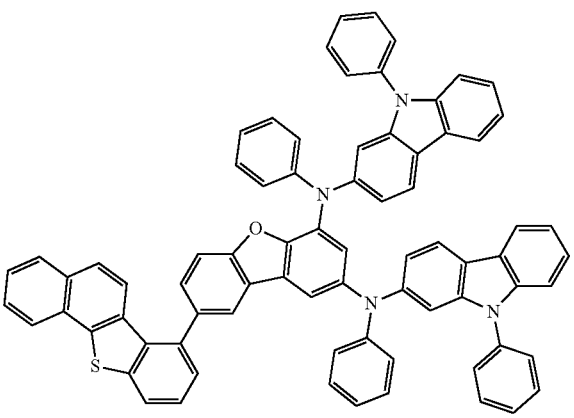
P-75
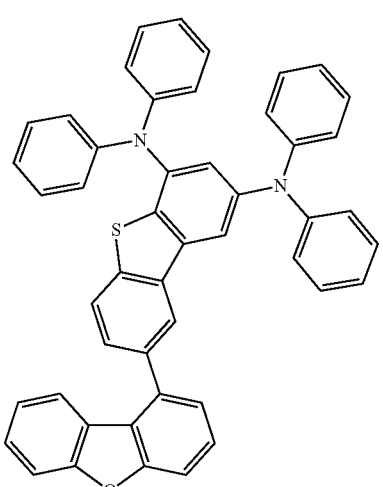
P-76
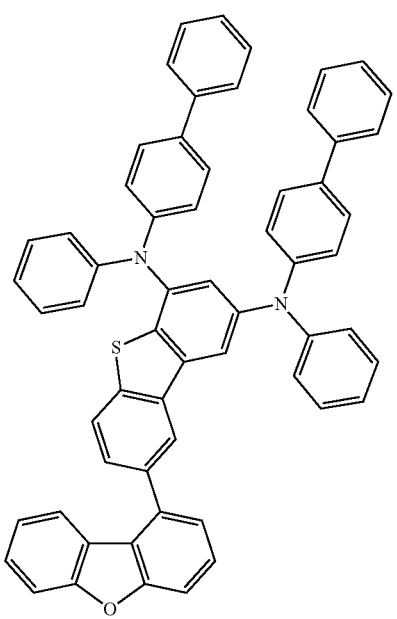

P-81

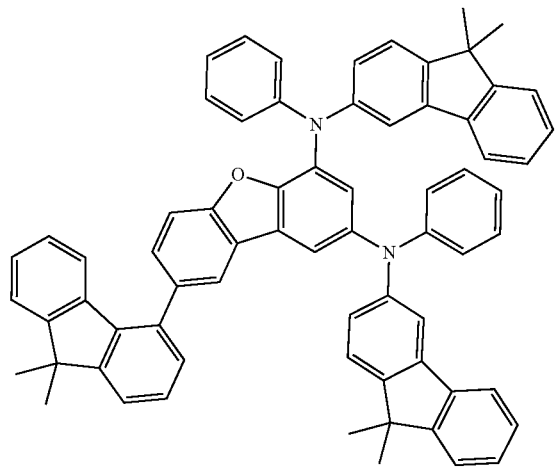

P-82

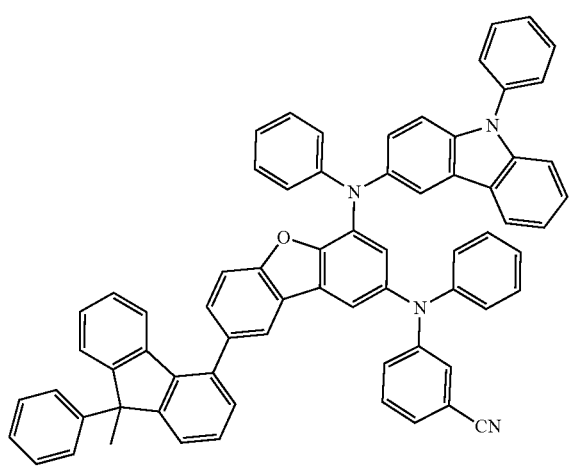

P-83

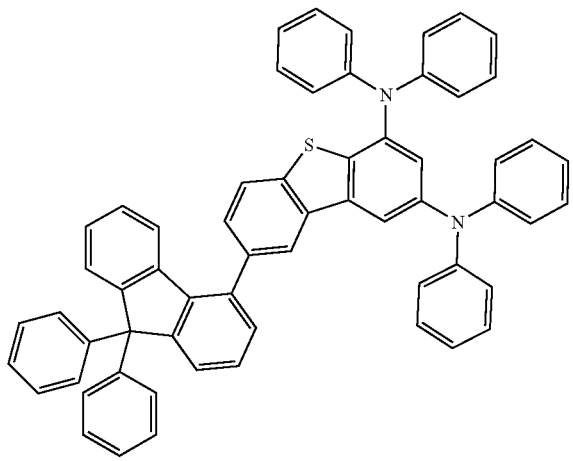

P-84

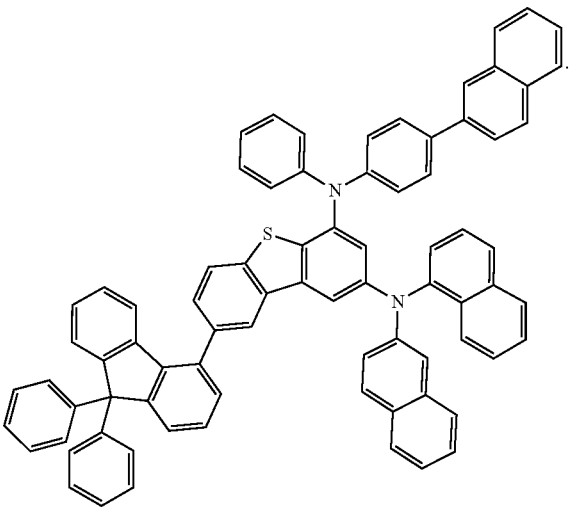

5. An organic electric element comprising:

a first electrode;

a second electrode; and an organic material layer positioned between the first electrode and the second electrode, wherein the organic material layer contains the compound of claim 1.

6. The organic electric element of claim 5, wherein the compound is contained such that a single kind of compound alone or a mixture of two or more kinds of compounds is contained.

7. The organic electric element of claim 5, wherein among a red auxiliary light emitting layer, a green auxiliary light emitting layer, and a blue auxiliary light emitting layer of the organic material layer, the compound is contained in the red auxiliary light emitting layer.

8. The organic electric element of claim 5, wherein the organic material layer is formed by at least of a spin coating process, a nozzle printing process, an inkjet printing process, a slot coating process, a dip coating process, or a roll-to-roll process.

9. An electronic device comprising:

a display device comprising the organic electric element of claim 5; and a controller for driving the display device.

10. The electronic device of claim 9, wherein the organic electric element is one of an organic light emitting diode, an organic solar cell, an organic photo conductor, an organic transistor, and an element for a monochromatic or white illumination.

11. A compound selected from:
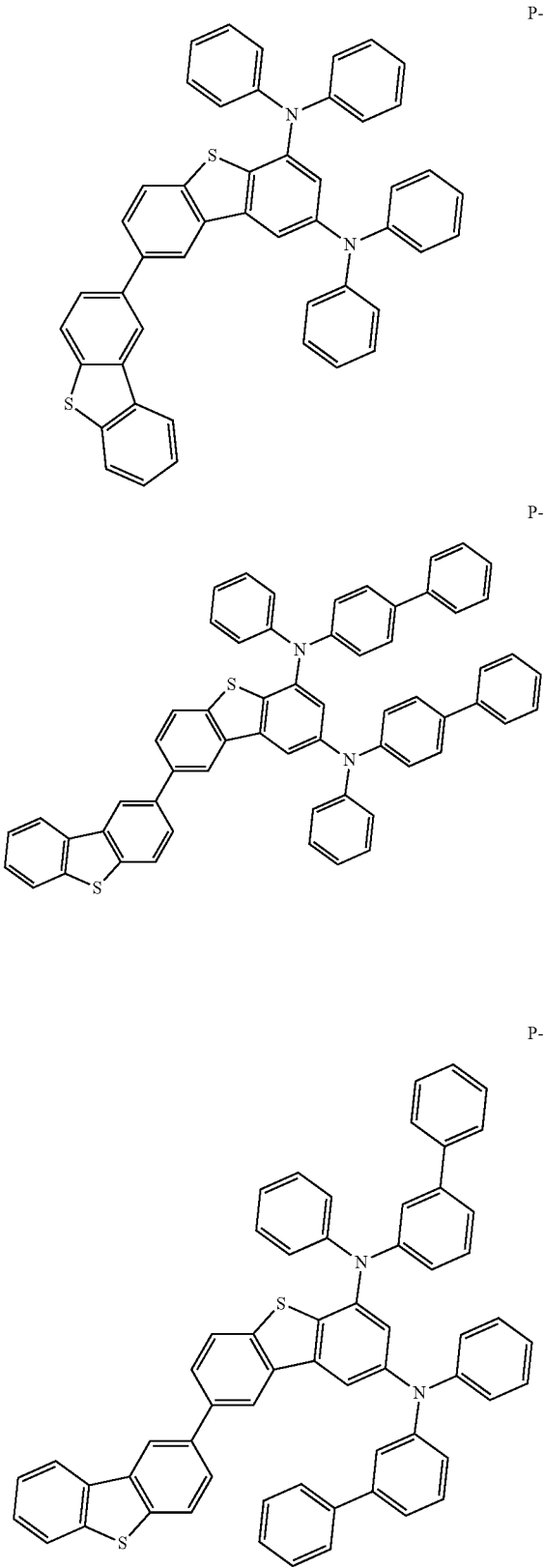
P-1
P-2
P-3
-continued
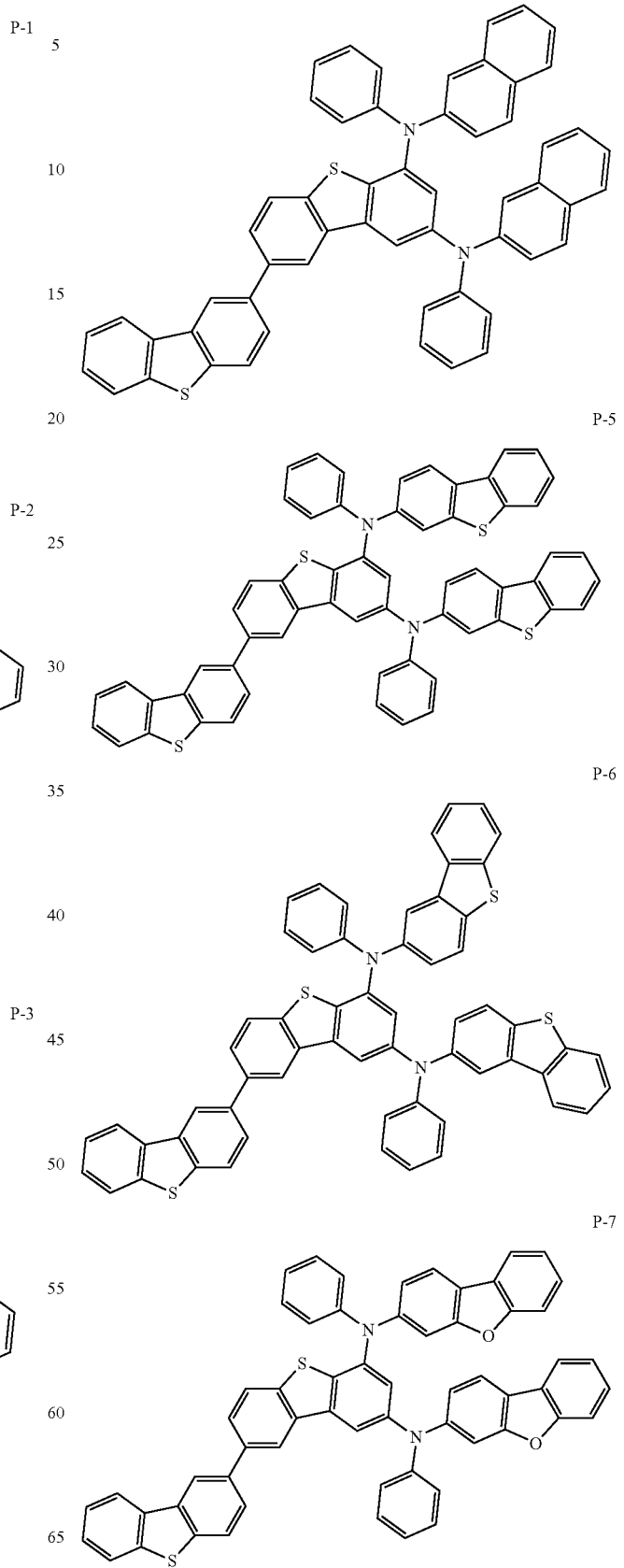
P-4
P-5
P-6
P-7

P-8
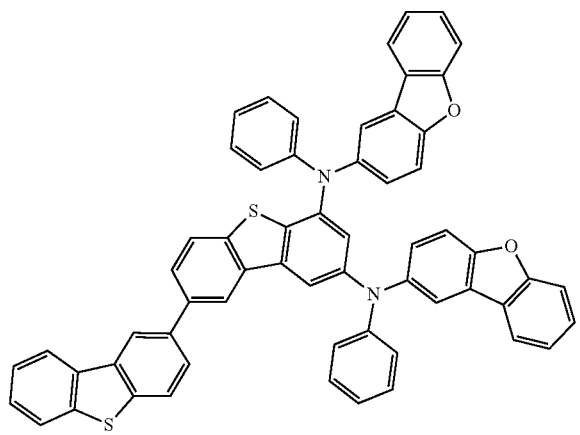
P-9
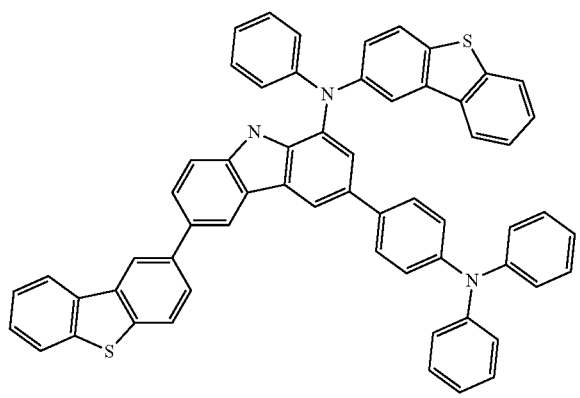
P-10
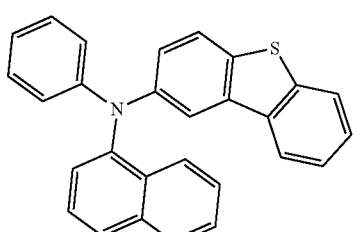
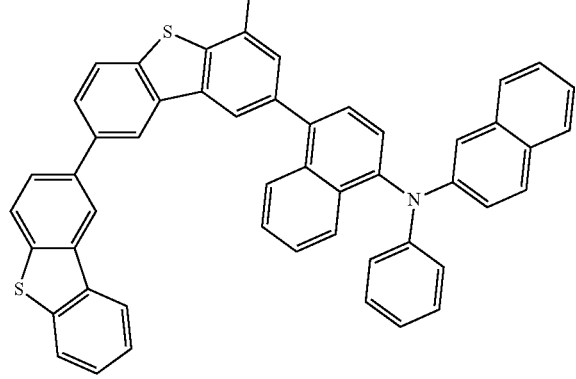
P-11
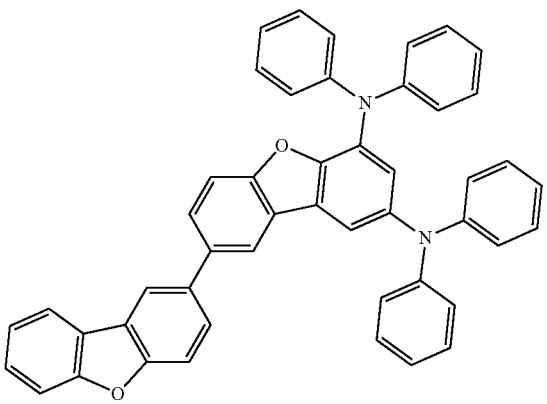
P-12
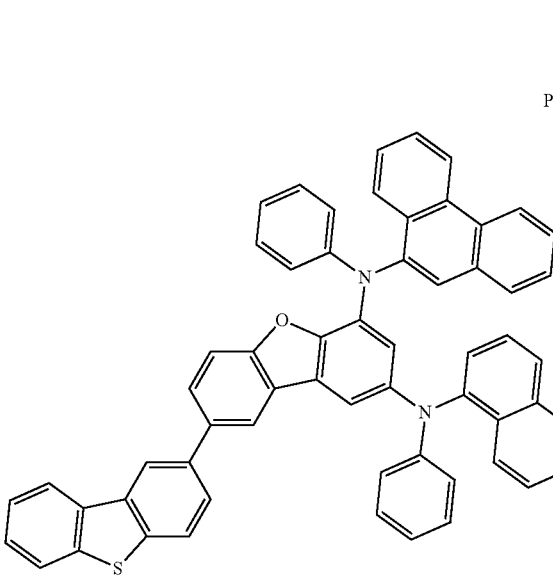
P-13
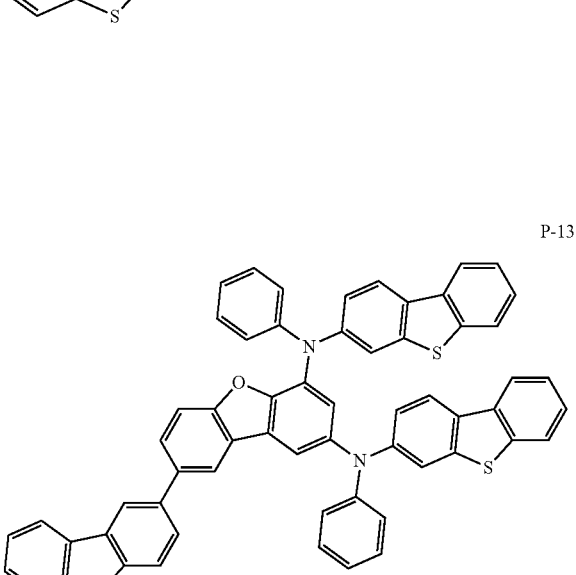

-continued
P-14
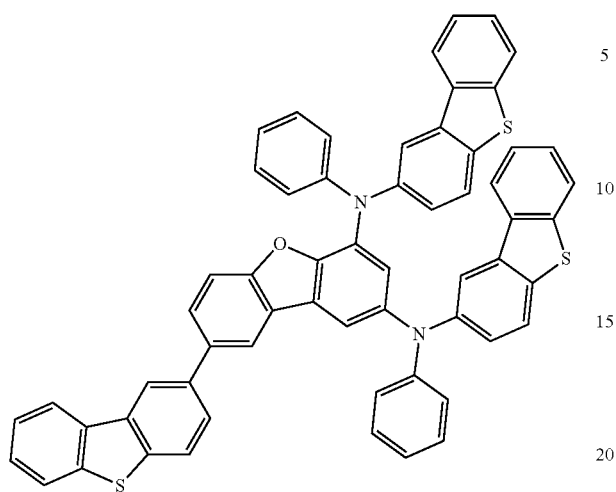
P-15
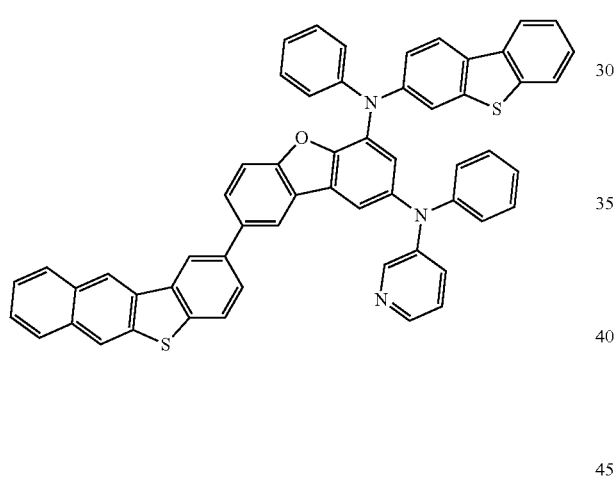
P-16
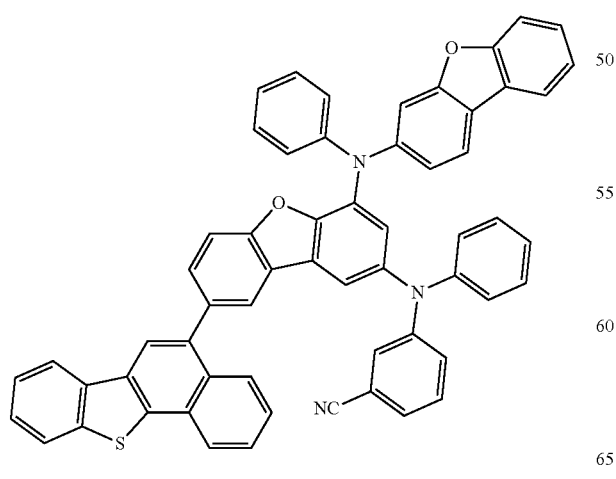
P-17
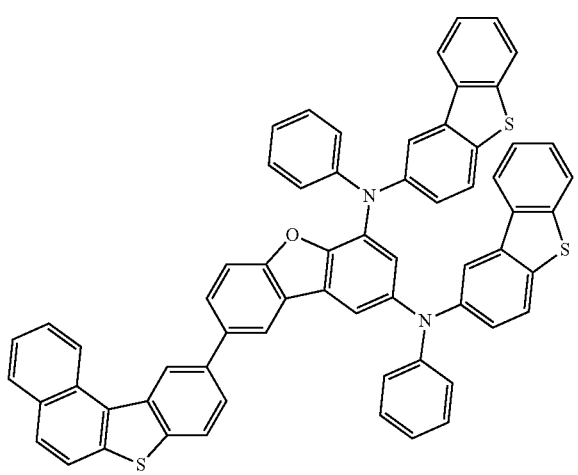
P-18
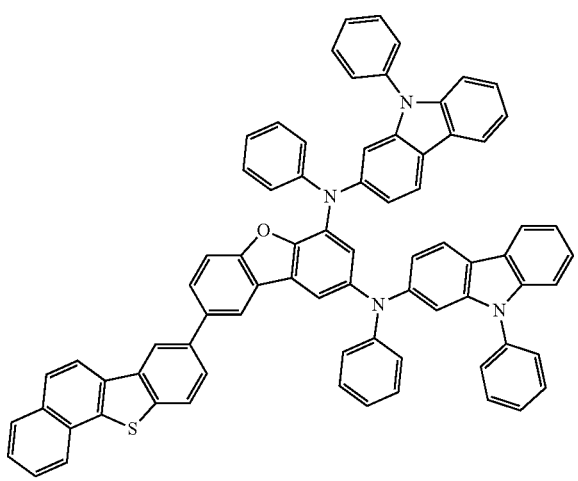
P-19
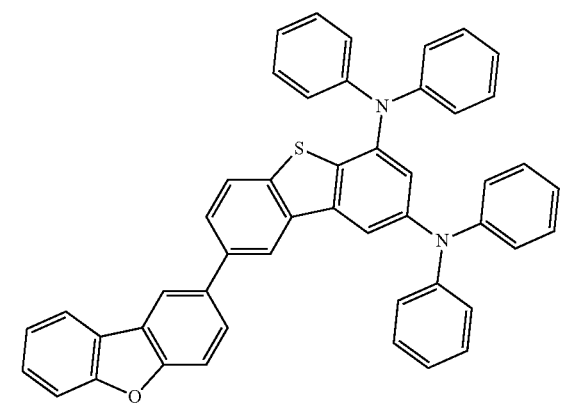

P-20
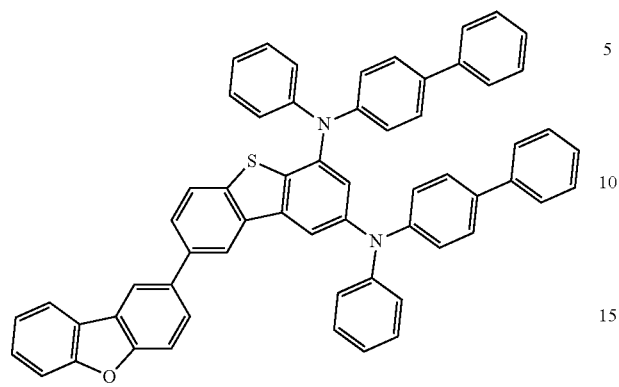
P-21
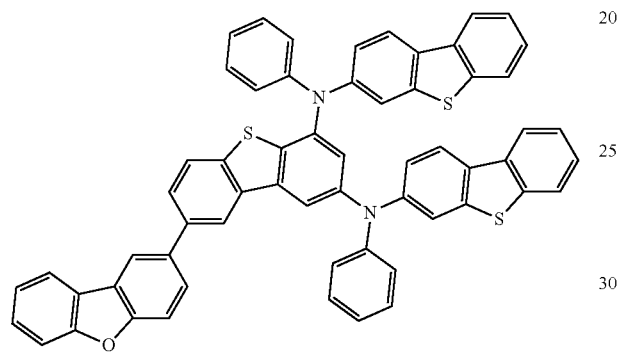
P-22
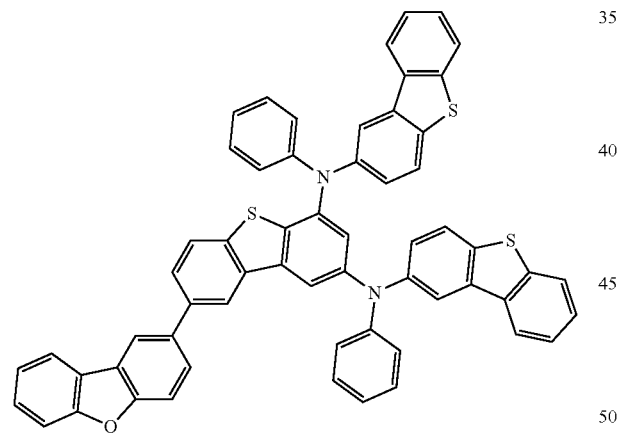
P-23
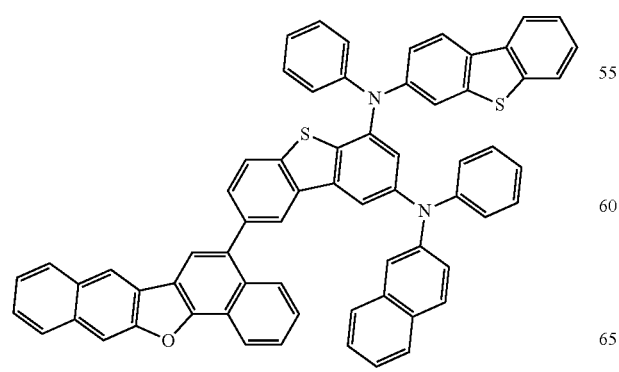
P-24
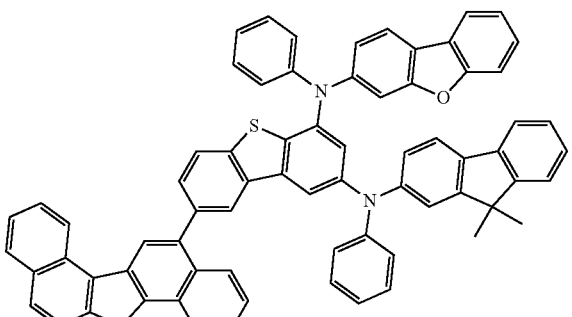
P-25
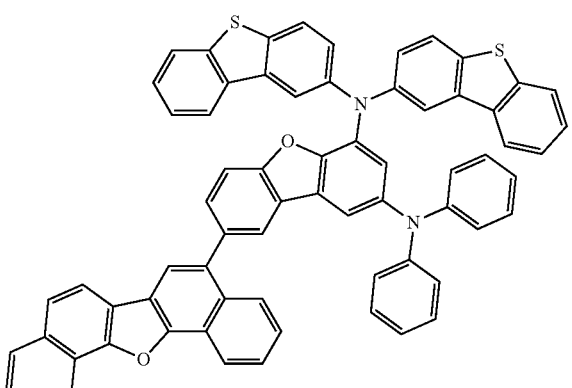
P-26
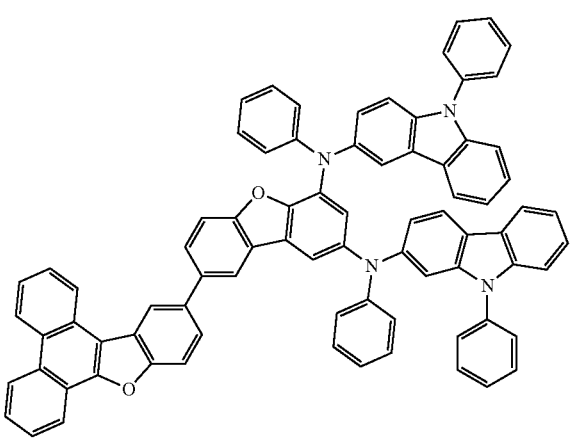

-continued
P-39
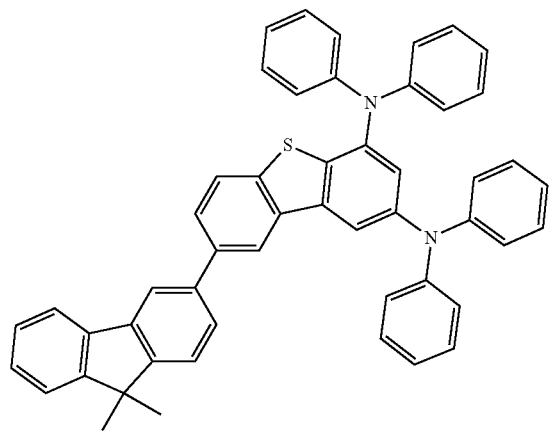
P-40
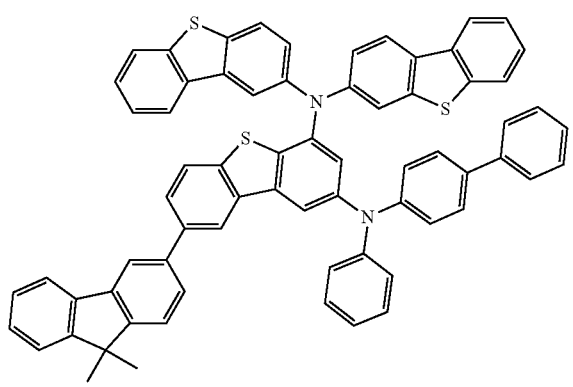
P-41
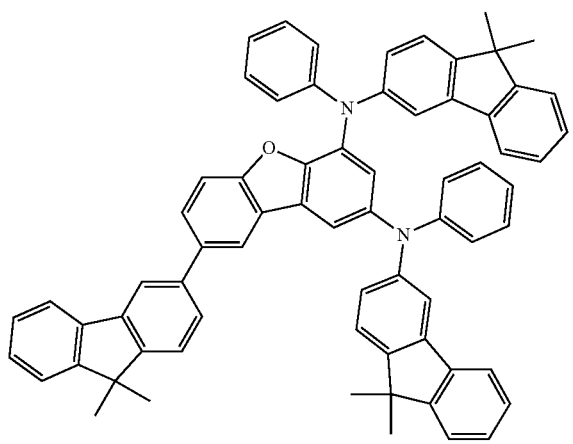
-continued
P-42
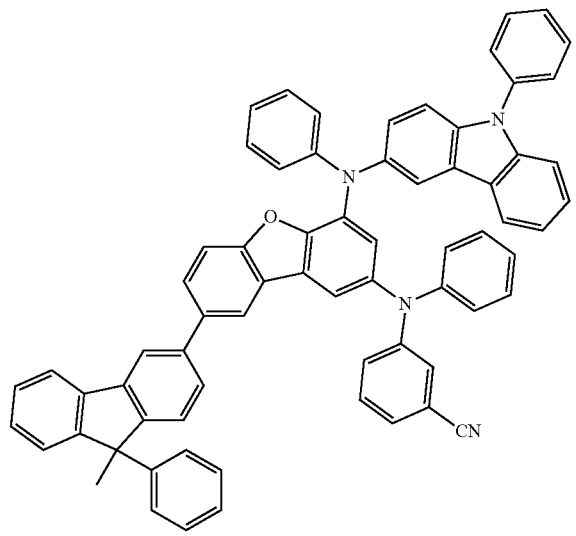
P-43
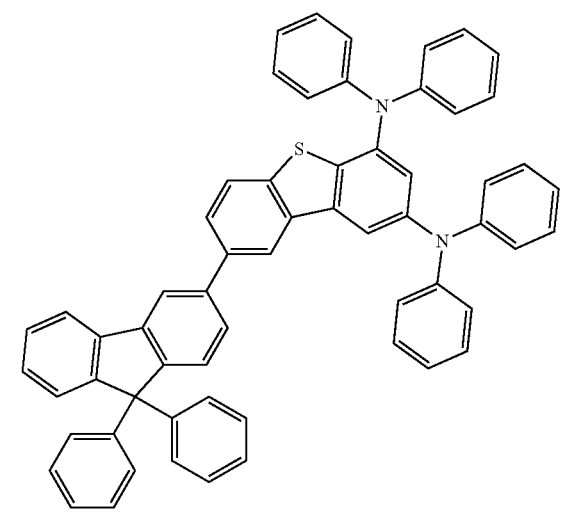
P-44
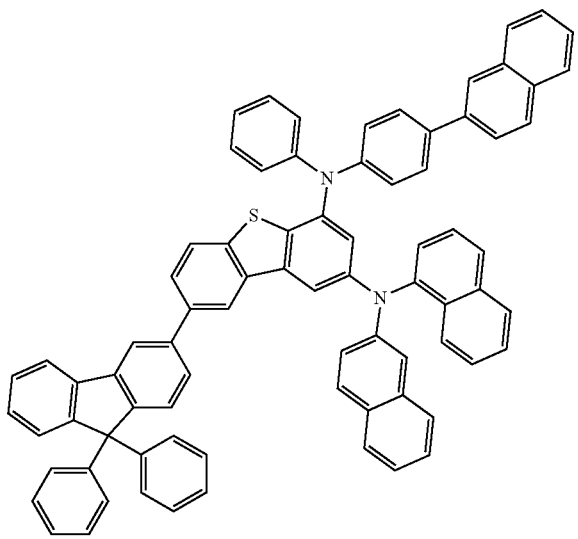

P-45
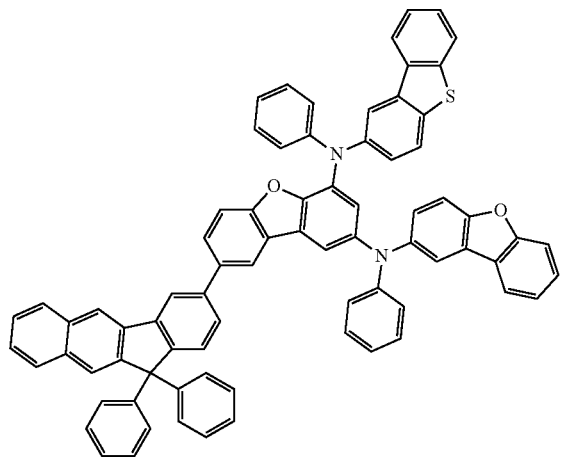
P-46
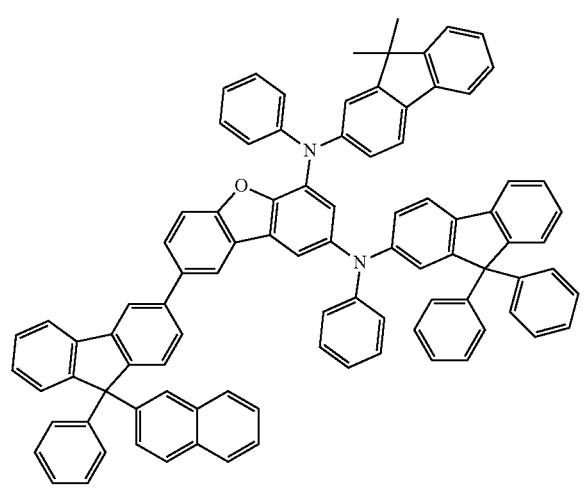
P-47
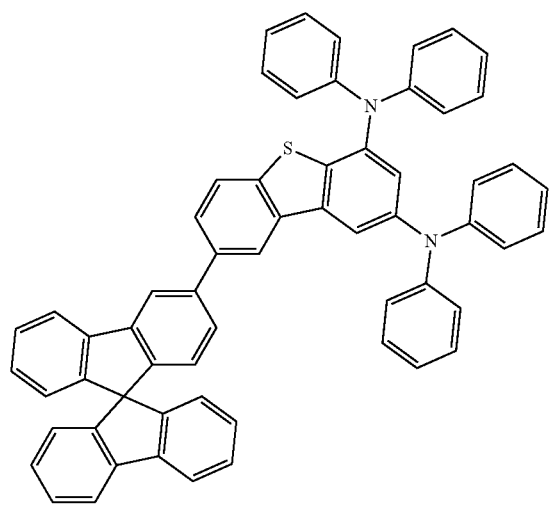
P-48
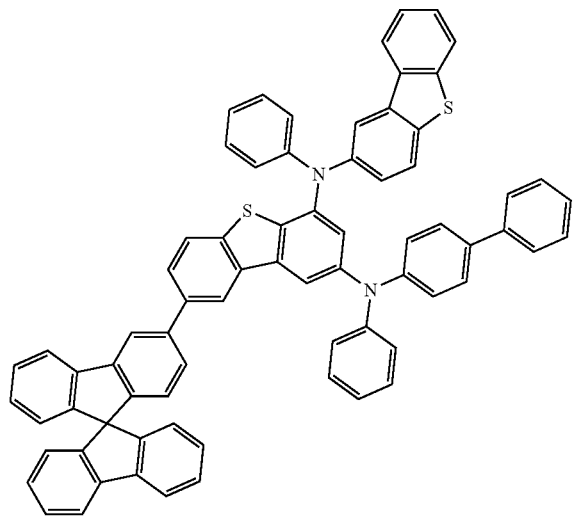
P-49
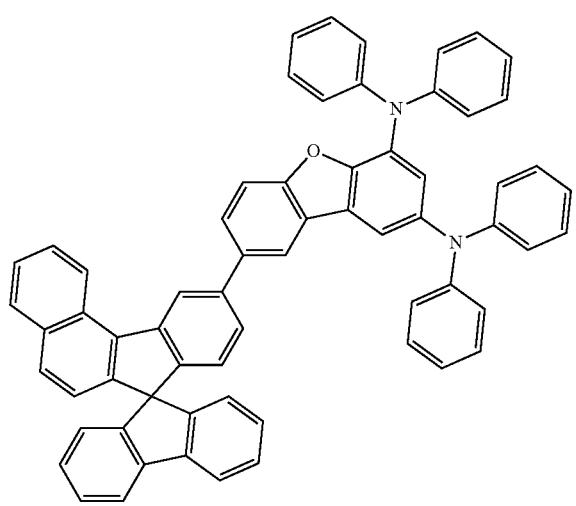
P-50
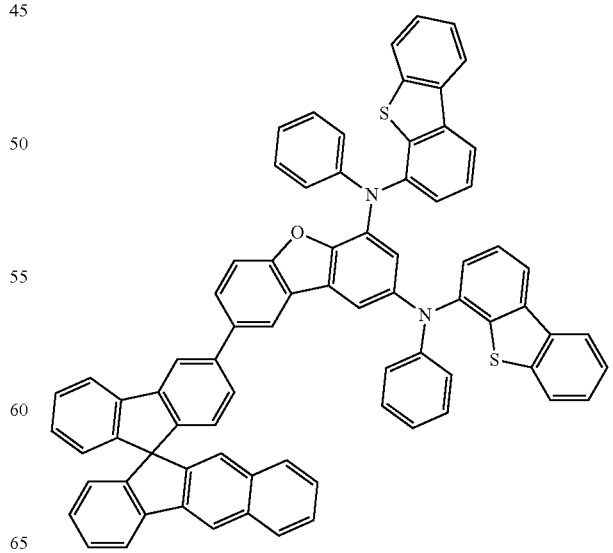

P-51
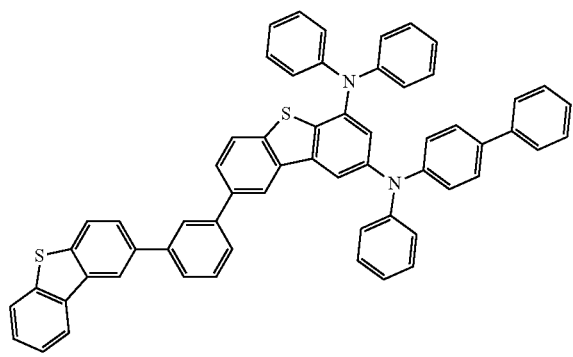
P-54
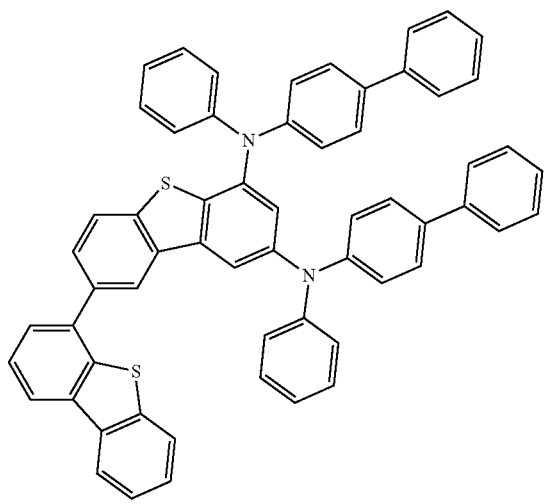
P-52
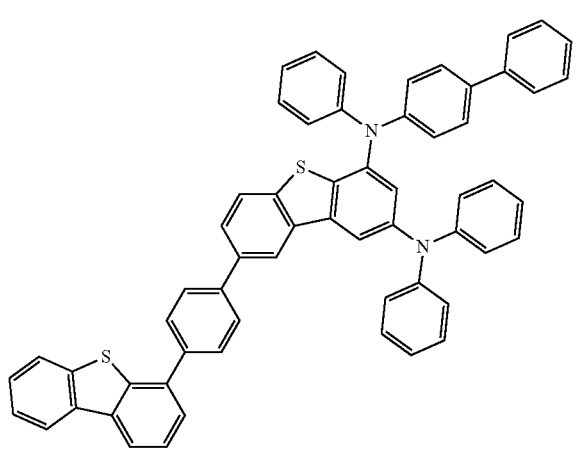
P-55
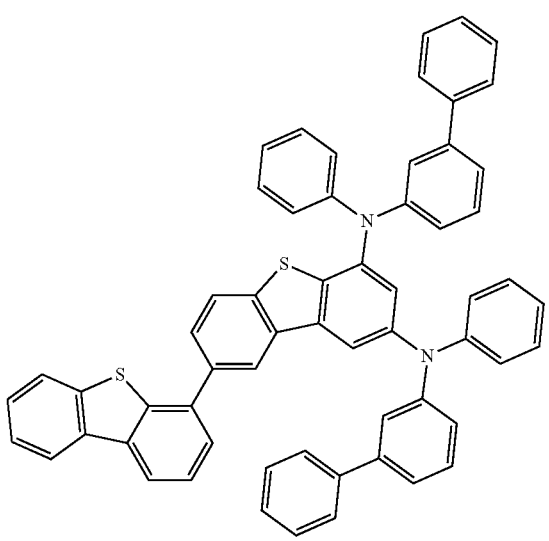
P-53
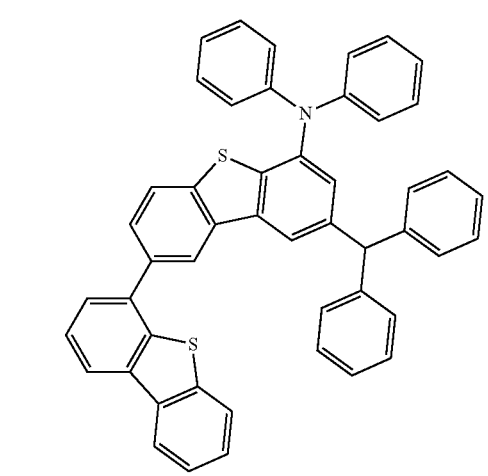
P-56
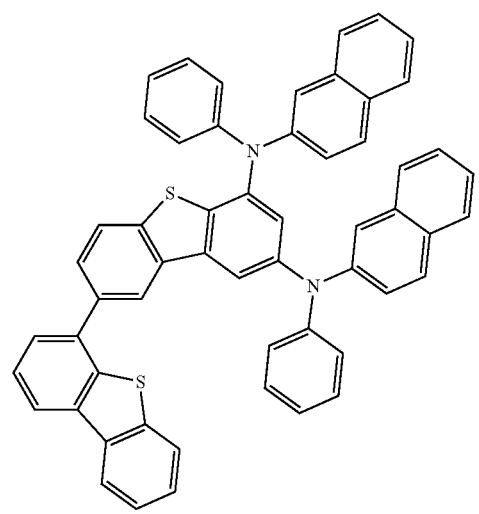

P-57
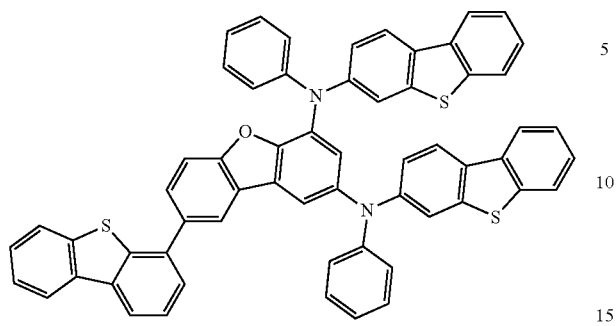
P-58
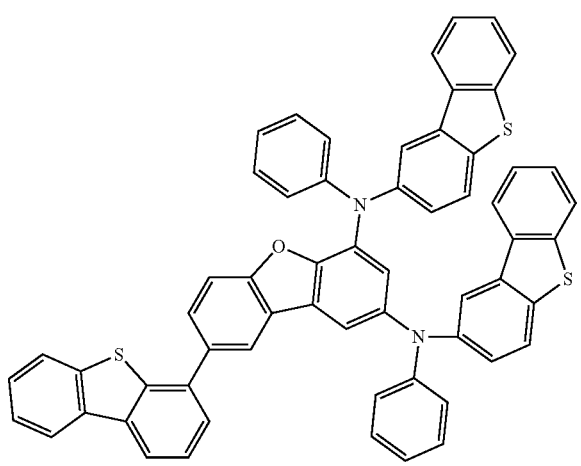
P-59
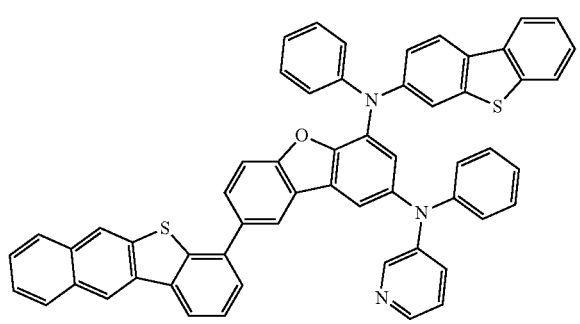
P-60
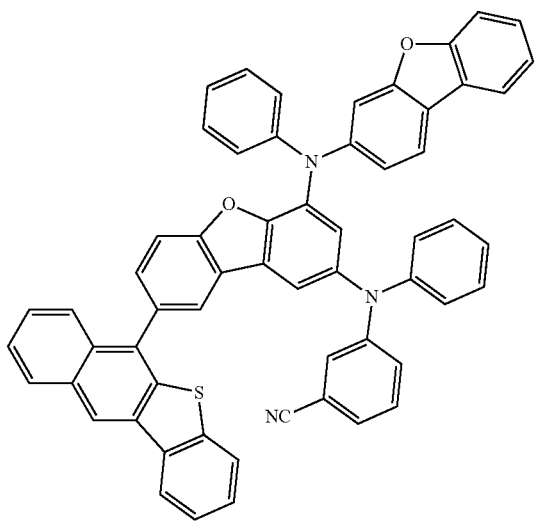
P-61
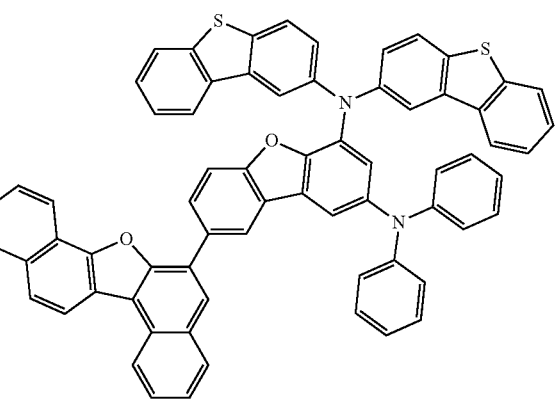
P-62
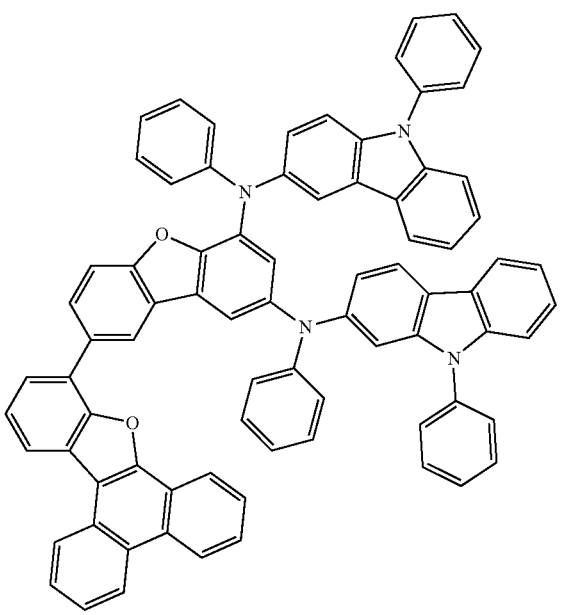

-continued
P-67
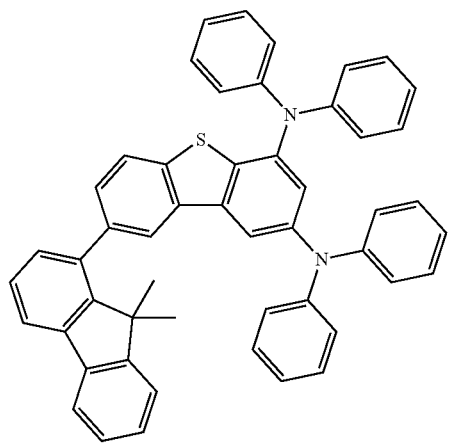
P-68
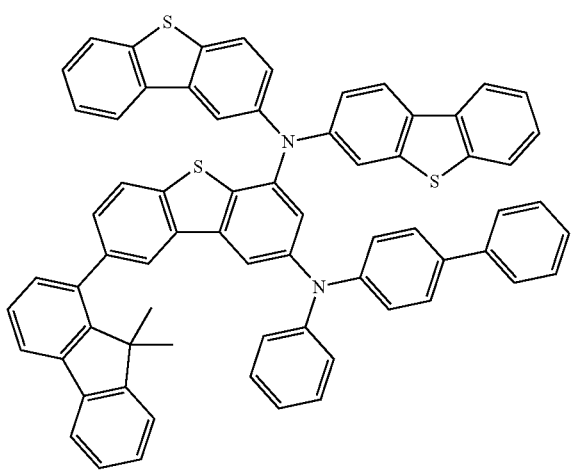
P-69
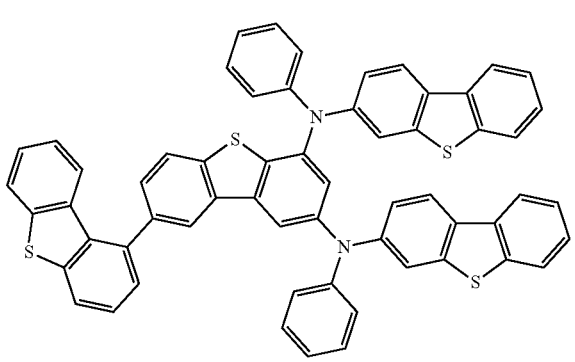
-continued
P-70
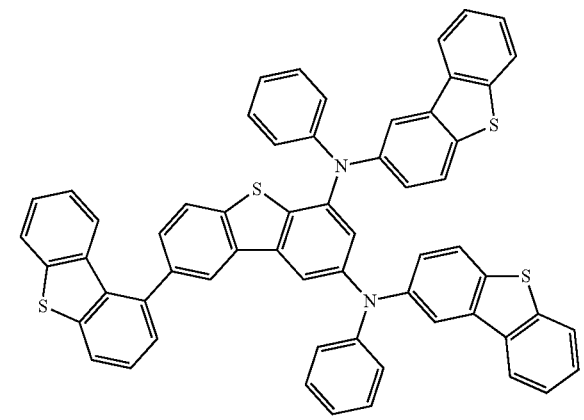
P-71
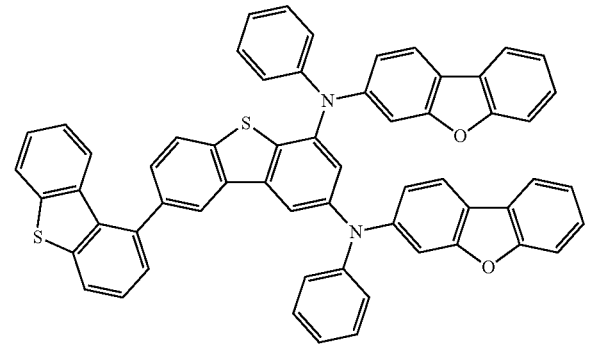
P-72
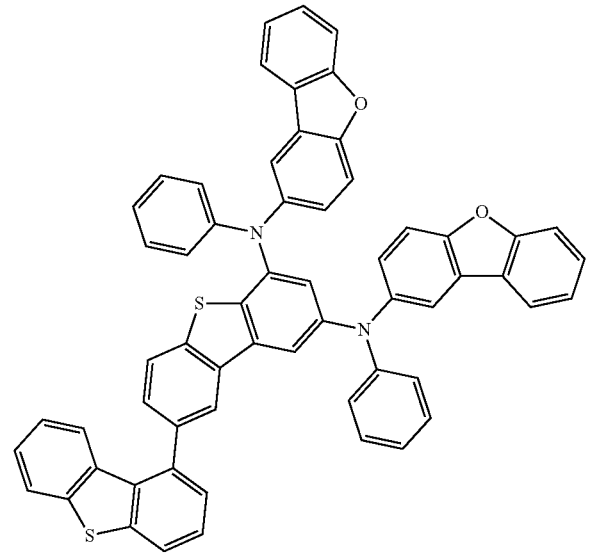

P-73
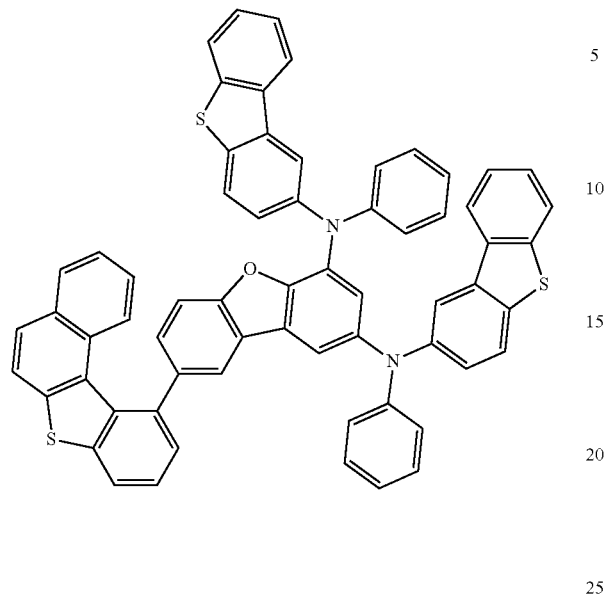
P-74
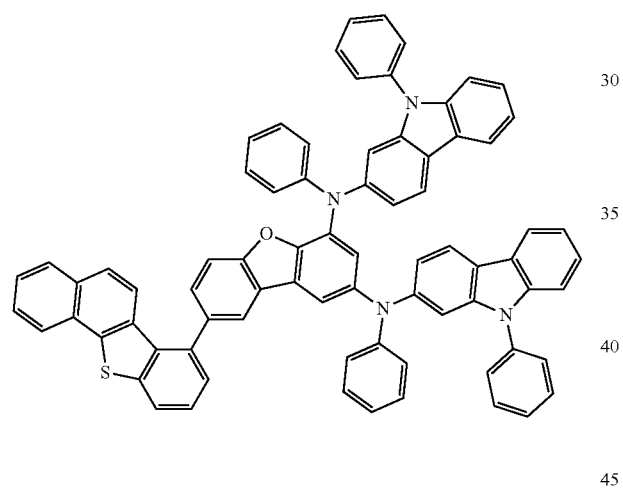
P-75
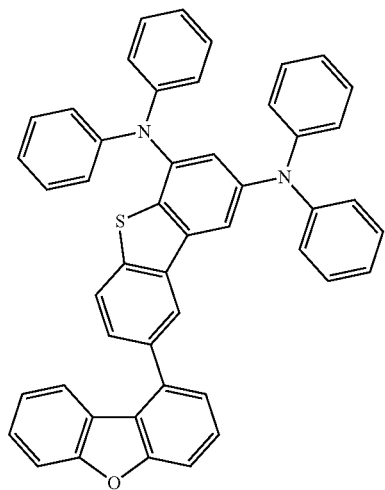
P-76
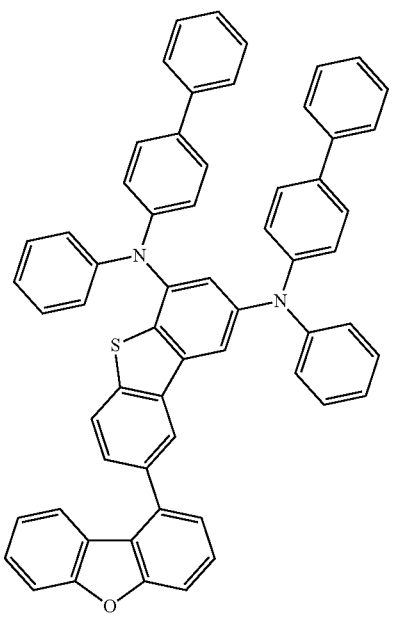
P-81
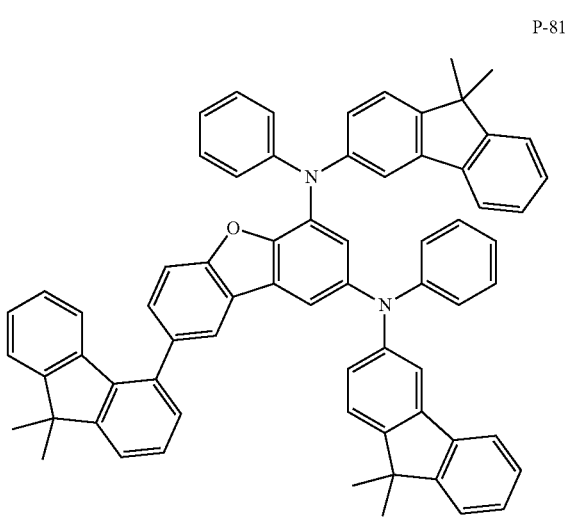
P-82
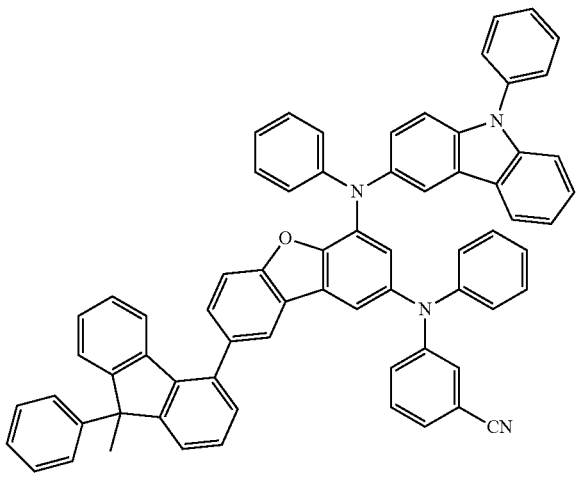

-continued
P-83
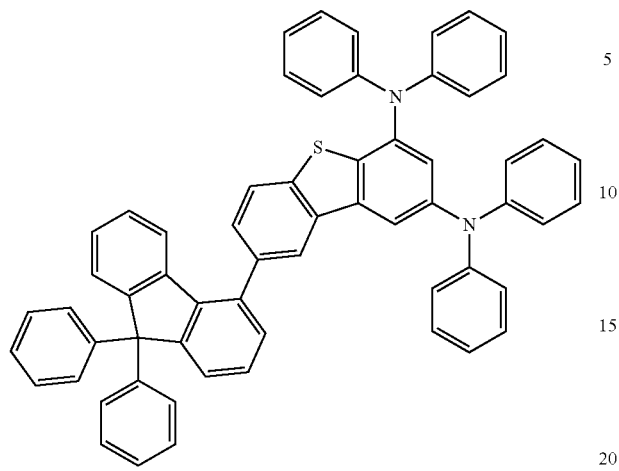
P-84
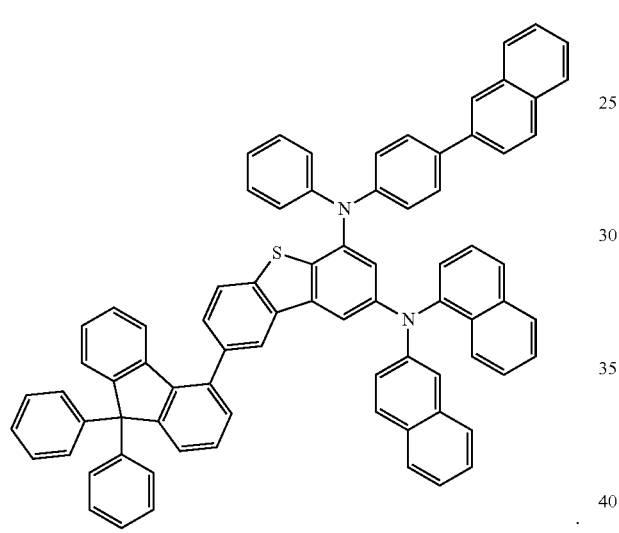
* * * * *